United States Patent
Marino et al.

(10) Patent No.: US 12,011,312 B2
(45) Date of Patent: Jun. 18, 2024

(54) IMAGE BASED POSITIONING AND GUIDANCE SYSTEM AND METHODS OF USE

(71) Applicant: Trinity Orthopedics, LLC, San Diego, CA (US)

(72) Inventors: James F. Marino, La Jolla, CA (US); Jamil Elbanna, San Diego, CA (US)

(73) Assignee: Trinity Orthopedics, LLC, San Diego, CA (US)

( * ) Notice: Subject to any disclaimer, the term of this patent is extended or adjusted under 35 U.S.C. 154(b) by 1085 days.

(21) Appl. No.: 16/757,357

(22) PCT Filed: Oct. 18, 2018

(86) PCT No.: PCT/US2018/056431
§ 371 (c)(1),
(2) Date: Apr. 17, 2020

(87) PCT Pub. No.: WO2019/079543
PCT Pub. Date: Apr. 25, 2019

(65) Prior Publication Data
US 2020/0237336 A1 Jul. 30, 2020

Related U.S. Application Data

(60) Provisional application No. 62/575,113, filed on Oct. 20, 2017.

(51) Int. Cl.
| | |
|---|---|
| *A61B 6/00* | (2006.01) |
| *A61B 34/20* | (2016.01) |
| *A61B 6/46* | (2024.01) |
| *A61B 17/00* | (2006.01) |
| *A61B 90/00* | (2016.01) |

(52) U.S. Cl.
CPC ............ *A61B 6/547* (2013.01); *A61B 6/4405* (2013.01); *A61B 6/56* (2013.01); *A61B 34/20* (2016.02); *A61B 6/465* (2013.01); *A61B 6/467* (2013.01); *A61B 2017/00477* (2013.01); *A61B 2017/0092* (2013.01); *A61B 2090/376* (2016.02); *A61B 2090/3764* (2016.02)

(58) Field of Classification Search
CPC ......... A61B 6/547; A61B 6/4405; A61B 6/56; A61B 6/465; A61B 6/467; A61B 6/548; A61B 6/04; A61B 6/4441; A61B 34/20; A61B 2017/00477; A61B 2017/0092; A61B 2090/376; A61B 2090/3764

See application file for complete search history.

(56) References Cited

U.S. PATENT DOCUMENTS

| | | |
|---|---|---|
| 5,283,808 A | 2/1994 | Cramer et al. |
| 6,267,502 B1 | 7/2001 | McNeirney et al. |

(Continued)

FOREIGN PATENT DOCUMENTS

| | | |
|---|---|---|
| CN | 206526110 U | 9/2017 |

*Primary Examiner* — Peter Luong
(74) *Attorney, Agent, or Firm* — Mintz Levin Cohn Ferris Glovsky and Popeo, P.C.

(57) ABSTRACT

Systems, devices, and methods to accurately and precisely align a visualized axis with one or more objects in an image field during a procedure using an imager based positioner system attached to an electronic positioning device are described. Specific methods of implanting guide pins into a first pedicle and a second pedicle of a vertebrae of a patient through a lumen of a trocar to a target of interest are also described.

7 Claims, 47 Drawing Sheets

(56) References Cited

U.S. PATENT DOCUMENTS

| | | |
|---|---|---|
| 7,600,915 B2 | 10/2009 | Marino |
| 7,690,844 B2 | 4/2010 | Marino |
| 2004/0133278 A1 | 7/2004 | Marino et al. |
| 2008/0015698 A1 | 1/2008 | Marino et al. |
| 2008/0077147 A1 | 3/2008 | Marino |
| 2008/0091081 A1 | 4/2008 | Marino |
| 2008/0234759 A1 | 9/2008 | Marino |
| 2009/0036895 A1 | 2/2009 | Marino |
| 2009/0062852 A1 | 3/2009 | Marino |
| 2009/0062914 A1 | 3/2009 | Marino |
| 2009/0157120 A1 | 6/2009 | Marino et al. |
| 2009/0275953 A1 | 11/2009 | Marino et al. |
| 2009/0299412 A1 | 12/2009 | Marino |
| 2009/0312764 A1 | 12/2009 | Marino |
| 2010/0111267 A1 | 5/2010 | Marino |
| 2010/0137875 A1 | 6/2010 | Marino et al. |
| 2010/0145348 A1 | 6/2010 | Marino |
| 2010/0241231 A1 | 9/2010 | Marino et al. |
| 2010/0290598 A1 | 11/2010 | Marino |
| 2010/0298890 A1 | 11/2010 | Marino |
| 2011/0004308 A1 | 1/2011 | Marino et al. |
| 2011/0009869 A1 | 1/2011 | Marino et al. |
| 2011/0028791 A1 | 2/2011 | Marino et al. |
| 2011/0245838 A1 | 10/2011 | Marino |
| 2012/0004688 A1 | 1/2012 | Marino et al. |
| 2012/0302839 A1 | 11/2012 | Marino |
| 2014/0012155 A1 | 1/2014 | Flaherty et al. |
| 2014/0018922 A1 | 1/2014 | Marino et al. |
| 2014/0141100 A1 | 5/2014 | Marino et al. |
| 2015/0148908 A1 | 5/2015 | Marino et al. |
| 2015/0216523 A1 | 8/2015 | Marino et al. |
| 2015/0238233 A1 | 8/2015 | Marino et al. |
| 2016/0270826 A1 | 9/2016 | Marino et al. |
| 2016/0302777 A1 | 10/2016 | Marino et al. |
| 2016/0310188 A1 | 10/2016 | Marino et al. |
| 2016/0345954 A1 | 12/2016 | Marino et al. |
| 2016/0367267 A1 | 12/2016 | Marino et al. |
| 2017/0215785 A1 | 8/2017 | Marino |

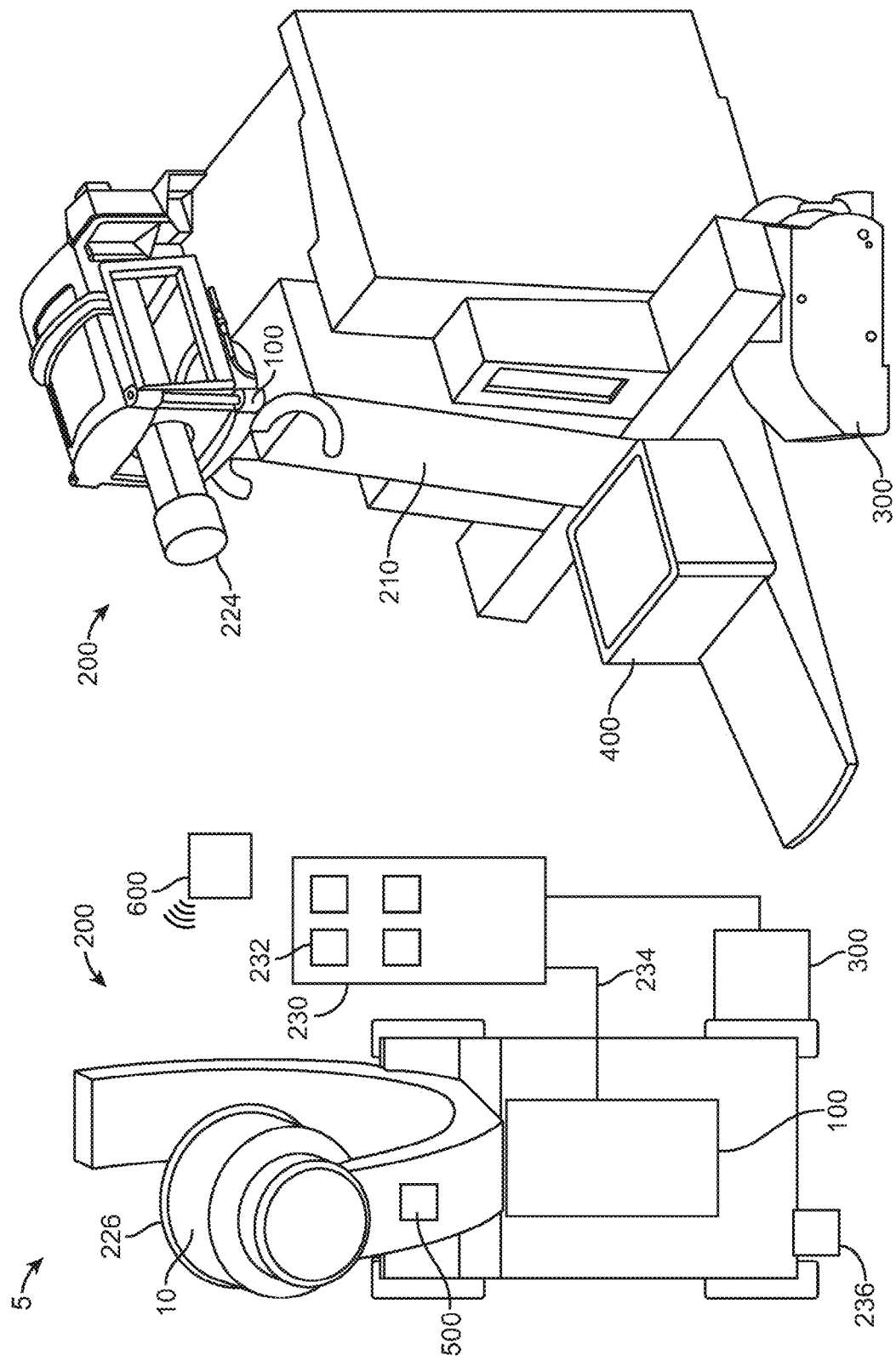

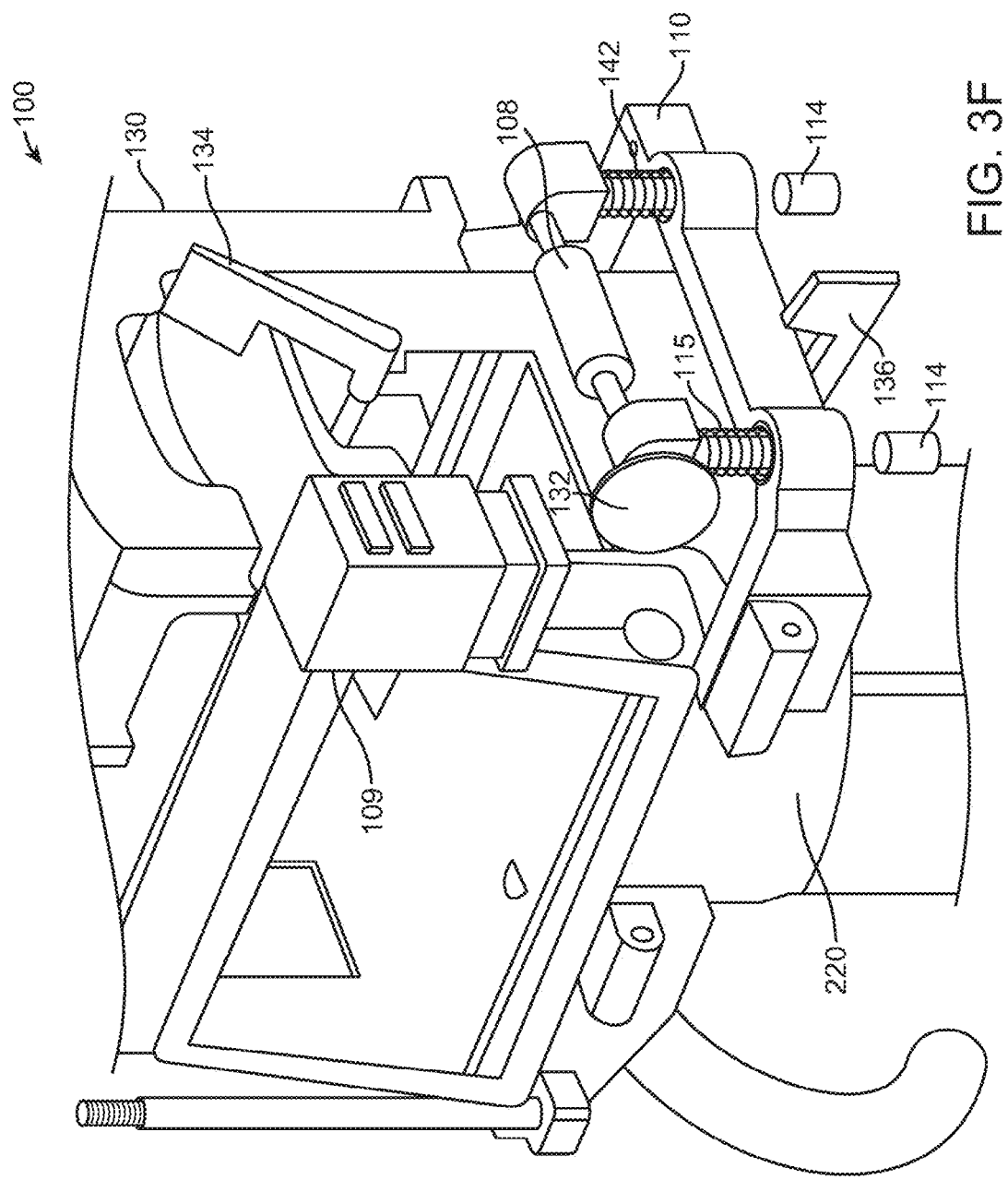

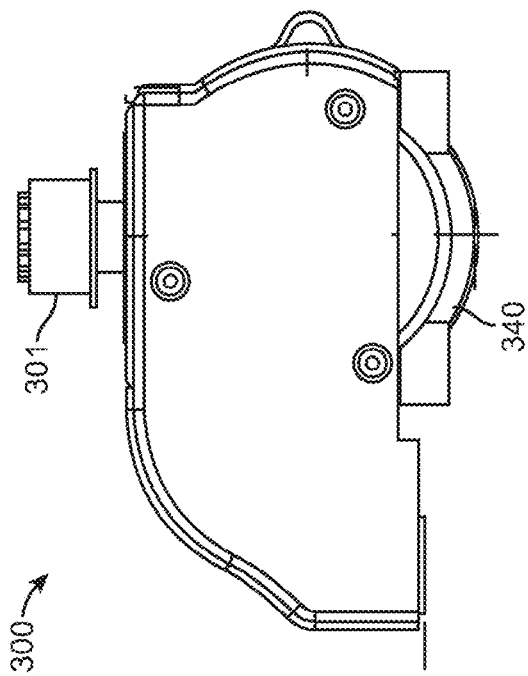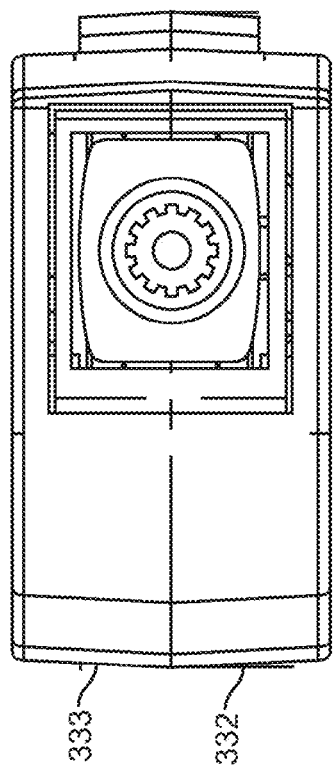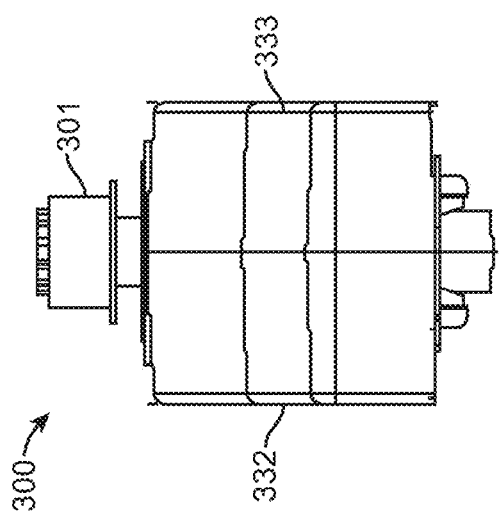

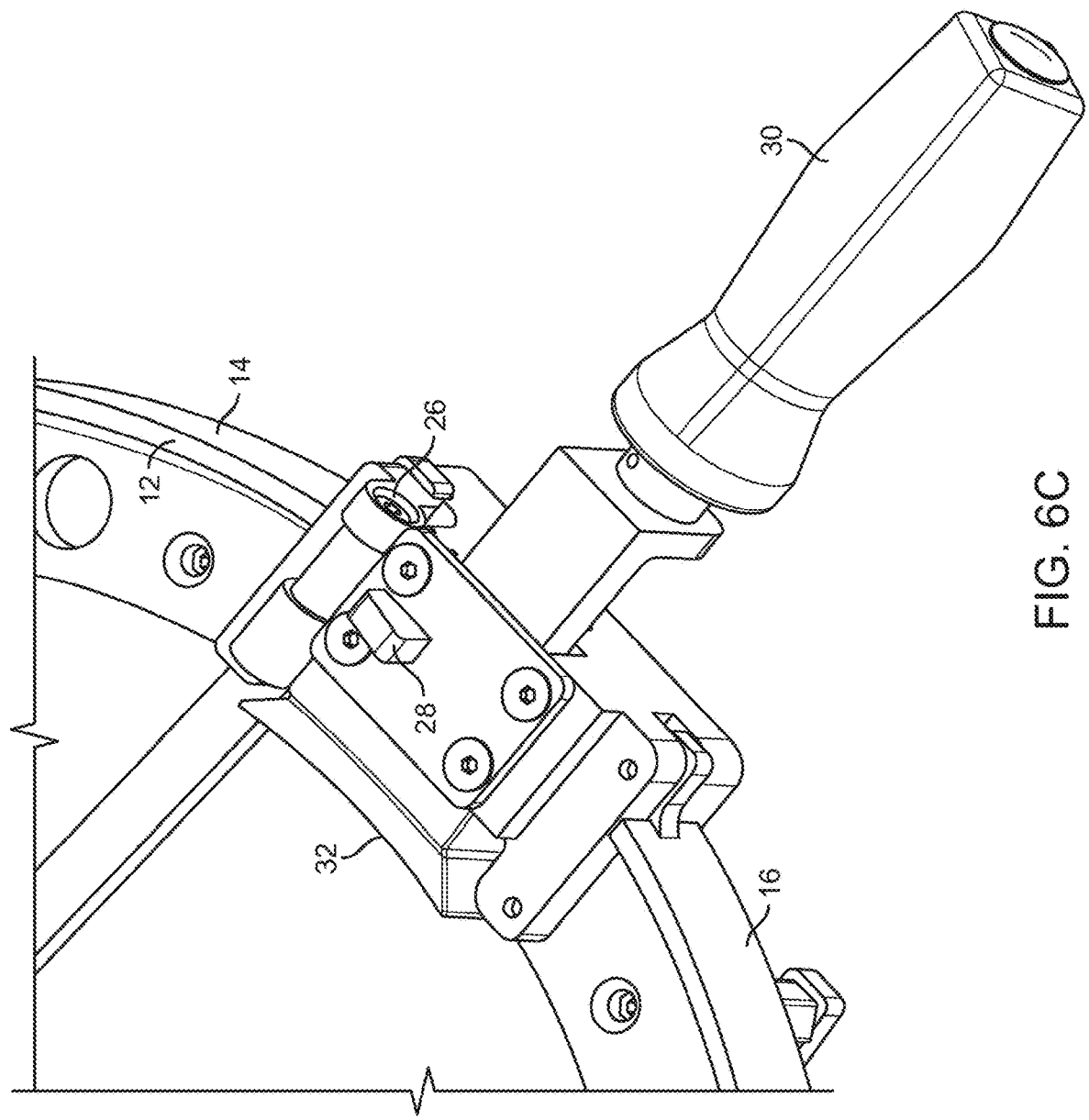

IMAGE BASED POSITIONING AND GUIDANCE SYSTEM AND METHODS OF USE

CROSS-REFERENCE TO RELATED APPLICATIONS

This application is a National Phase filing of PCT/US2018/056431 filed Oct. 18, 2018 entitled "Imager-Based Positioning and Guidance System and Methods of Use" and claims the benefit of U.S. Provisional Patent Application Ser. No. 62/575,113, filed Oct. 20, 2017, entitled "Imager-Based Positioning and Guidance System and Methods of Use" the disclosure of which is hereby incorporated by reference in its entirety for all purposes.

BACKGROUND

In many procedures, including medical procedures, imagers, such as electromagnetic-based image intensifiers may be employed to localize or isolate points or planes of interest. The resultant generated images may be used to place one or more objects near or adjacent the point(s) or plane(s) of interest. It is desirable to be able to employ the imager to actively aid in the placement of the object(s). To accurately and precisely position or re-position a guidance system, including image intensifiers, guidance system positioners that allow for incremental positioning of at least one adjustable axis of the guidance system are used.

Correct positioning of instruments and/or implants, including those used in a surgical procedure with respect to patient anatomy, is often an important factor in achieving a successful outcome. Imaging systems allow visualization of an area to assist in placement of various devices. However, images produced by C-Arm X-ray examination systems can suffer from distortion and prolonged imaging may expose the patient to additional unnecessary radiation, for example. Similar systems are difficult to use and often lack the accuracy and/or precision that may be required particularly during intricate procedures including, but not limited to, spinal surgery.

SUMMARY

Described herein are devices, systems, and methods for incrementally positioning at least one adjustable axis of a guidance system where the guidance system may be an image based guidance system.

In an implementation, described is a method of coaxially aligning a bushing axis of a surgical navigation device with a central beam axis of a portable imaging device. The method comprises reversibly attaching an annular ring of the surgical navigation device to an image intensifier receiver of the portable imaging device. The annular support ring is attached to an image intensifier object positioner. At least two connecting elements interposed between one or more attachment features of the image intensifier object positioner and the annular support ring are adjusted to suspend a guide bushing between an emitter of the imaging device and the image intensifier receiver. The position of the bushing axis and the central beam axis is checked. An orientation of the bushing axis of the guide bushing is optionally altered by adjusting a length of at least two connecting elements to coaxially align the bushing axis with the central beam axis of the portable imaging device.

The portable imaging device can be a radiation-based imaging device including a fluoroscope, X-ray machine, or C-Arm. The at least two connecting elements can be threaded elements. Adjusting the at least two connecting elements can include a linear translational adjustment. At least a portion of the guide bushing can be radiolucent and/or removable from the surgical navigation device.

In an implementation, described is a device to coaxially align a guide bushing of a detachable surgical navigation device with a central beam axis of a portable imaging device. The device comprises an annular ring of the detachable surgical navigation device configured to be attached to an image intensifier receiver of the portable imaging device. The annular support ring is configured to be attached to an image intensifier object positioner. The device also comprises at least two connecting elements interposed between one or more attachment features of the image intensifier object positioner and the annular support ring. At least two connecting elements are configured to suspend a guide bushing between an emitter of the imaging device and the image intensifier receiver. An orientation of the bushing axis of the guide bushing is altered by adjusting a length of at least two connecting elements to coaxially align the bushing axis with the central beam axis of the portable imaging device.

The at least two connecting elements can be threaded connecting elements configured for linear translational adjustment. The guide bushing can be movable both proximate to and distal to the image intensifier receiver of the portable imaging device. The detachable surgical navigation device can be circumferentially moveable about an axis of the guide bushing. The portable imaging device can be a radiation-based imaging device including a fluoroscope, X-ray machine, or C-Arm, for example.

In an implementation, described is a method of associating at least one sensor with a rotatable element of a portable imaging device. The imaging device has a central beam axis and the method comprises providing the portable imaging device. The at least one senor is attached to the rotatable element of the portable imaging device. The at least one sensor is configured to sense and transmit data. At least one sensor is connected to a computing device. The rotatable element is moved in an arcuate motion relative to a gravity line. Data, including an orientation of the rotatable element relative to the gravity line, is transmitted (as sensed by at least one sensor) to the computing device. The computing device has a viewable display and/or a graphical user interface.

At least one sensor can be an inclinometer and/or a directional accelerometer. The rotating element can be a C-Arm and the portable imaging device is a fluoroscopy machine. The C-Arm can include a portable image intensifier with the at least one sensor attached thereto and configured to measure an angle of tilt of the C-Arm with respect to gravity. The orientation of the rotatable element can include measured angles of slope or tilt from the at least one sensor. The orientation of the rotatable element relative to the gravity line can include a first orthogonal plane and a second orthogonal plane. Each of the first and second orthogonal planes substantially correspond to a sagittal plane and an axial plane of a patient so that when the rotatable element is rotated about the patient, a relative orientation of the central beam axis within the first and second orthogonal planes can be determined relative to the patient. Attaching at least one sensor to the rotatable element of the portable imaging device provides remote reporting of arcuate movements of the rotatable element relative to a gravity line in at least one orthogonal plane. The at least one sensor can include at least one MEMS device and a Bluetooth™ connection to wirelessly connect to the viewable display and/or the graphical user interface of the computing device.

In an implementation, described is a method of redirecting a flexible elongate member along a non-linear pathway and through a bore of a linear support sleeve. The support sleeve is held by a surgical guide bushing positioned coaxially within a central beam axis of a portable imaging device. The method comprises providing the elongate member having an initial delivery axis and altering the initial delivery axis of the elongate member to a secondary delivery axis when the elongate member is positioned within the bore of the support sleeve. The elongate member is positioned within a patient substantially along the central beam axis of an image intensifier between the patient and a receiver element of the portable imaging device.

The elongate member can be a guide pin or a needle. The difference between the initial delivery axis and the secondary delivery axis of the elongate member can be between 45 degrees and 120 degrees. More specifically, the difference can be about 90 degrees. The portable imaging device can be a radiation-based imaging device including a fluoroscope, X-ray machine, or C-Arm. The method can further comprise coupling a guide element to the linear support sleeve. A bore of the guide element can be coaxially aligned with the bore of the linear support sleeve. A removable redirection support can be optionally mated with the guide element. The linear support sleeve can be at least partially radiopaque and the redirection support can be at least partially radiolucent. Furthermore, at least a portion of the non-linear pathway can be a radiolucent ceramic material.

In some variations, one or more of the following can optionally be included in any feasible combination in the above methods, devices, and systems. More details of the devices, systems, and method are set forth in the accompanying drawings and the description below. Other features and advantages will be apparent from the description and figures.

BRIEF DESCRIPTION OF THE DRAWINGS

These and other aspects, features and advantages of various implementations will now be described in detail with reference to the following drawings. Generally speaking, the figures are not to scale in absolute terms or comparatively but are intended to be illustrative. Also, relative placement of features and elements may be modified for the purpose of illustrative clarity.

FIG. 1A is a diagram of a guidance system including at least one electronic positioning device and an imager based object positioner system according to various implementations;

FIG. 1B is a diagram of a segment of guidance system including at least one electronic positioning device according to various implementations;

FIG. 3F is a partial exploded back view of a boom electronic positioning device according to various implementations;

FIG. 4A is a back view of a chassis based electronic positioning device according to various implementations;

FIG. 4B is a side view of a chassis based electronic positioning device according to various implementations;

FIG. 4C is a top view of a chassis based electronic positioning device according to various implementations;

FIG. 6C is a top, partial view of a moveable clamp apparatus of the imager based object positioner system shown in FIG. 6A.

It should be appreciated that the drawings herein are exemplary only and are not meant to be to scale.

DETAILED DESCRIPTION

The present disclosure relates generally an apparatus, systems, and methods for guiding the placement of an object to a desired location based on images generated by an image intensifier, including all forms of X-ray, in which the X-ray beam source is mechanically linked to an X-ray beam receptor, including a C-Arm fluoroscope or other type of imaging system in which a radiation beam is being generated for surgical guidance purposes.

As used in this disclosure, except where the context requires otherwise, the term "comprise" and variations of the term, such as "comprising," "comprises" and "comprised" are not intended to exclude other additives, components, integers or steps.

As used in this disclosure, except where the context requires otherwise, the method steps disclosed and shown are not intended to be limiting nor are they intended to indicate that each step is essential to the method or that each step must occur in the order disclosed but instead are exemplary steps only.

All dimensions specified in this disclosure are by way of example only and are not intended to be limiting, except where the context requires otherwise. Further, the proportions shown in these figures are not necessarily to scale. As will be understood by those with skill in the art with reference to this disclosure, the actual dimensions and proportions of any device or part of a device disclosed in this disclosure will be determined by its intended use.

Figure 1C:
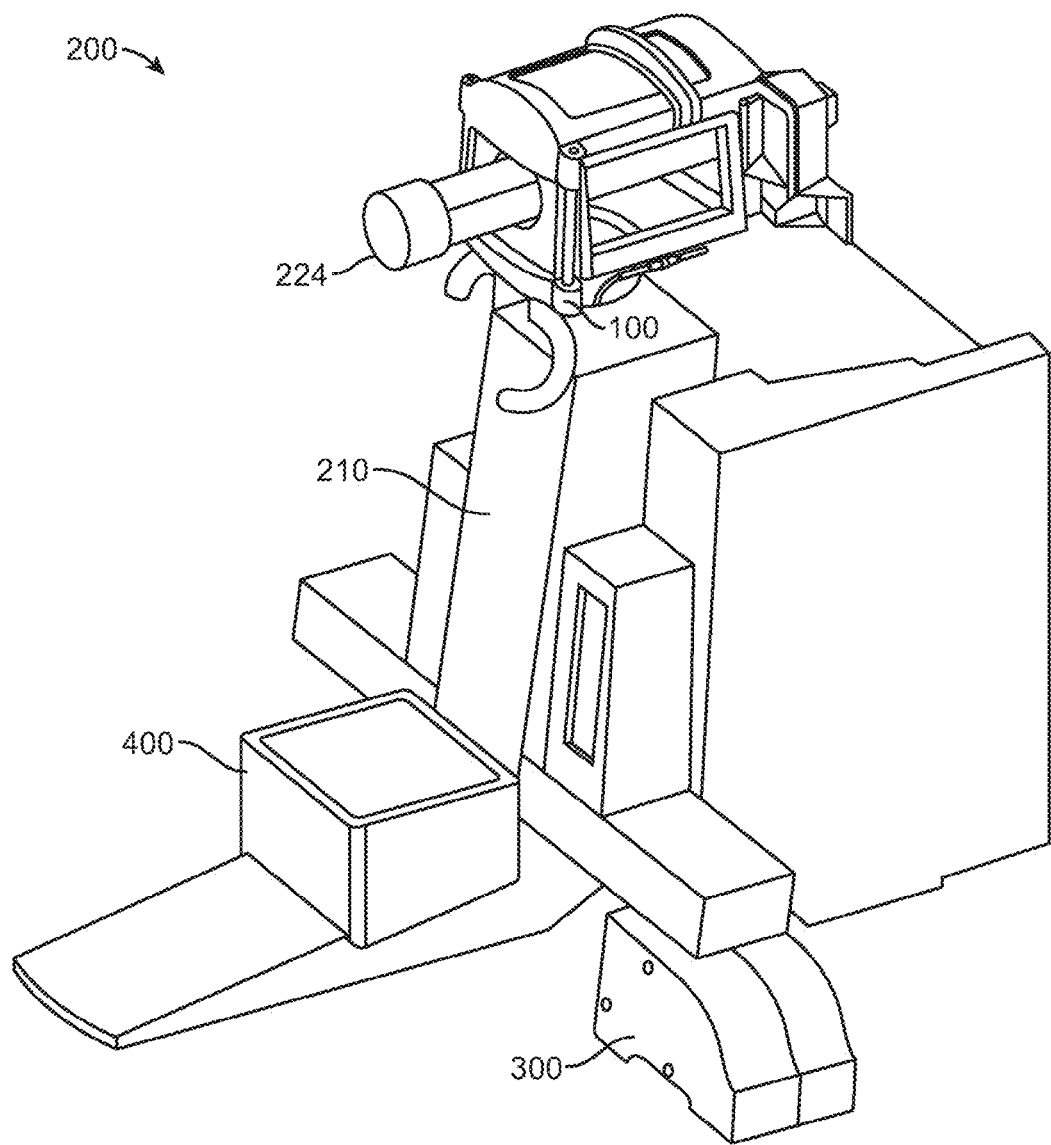
FIG. 1C is a diagram of a segment of guidance system including at least one electronic positioning device according to various implementations.
Figure 1D:
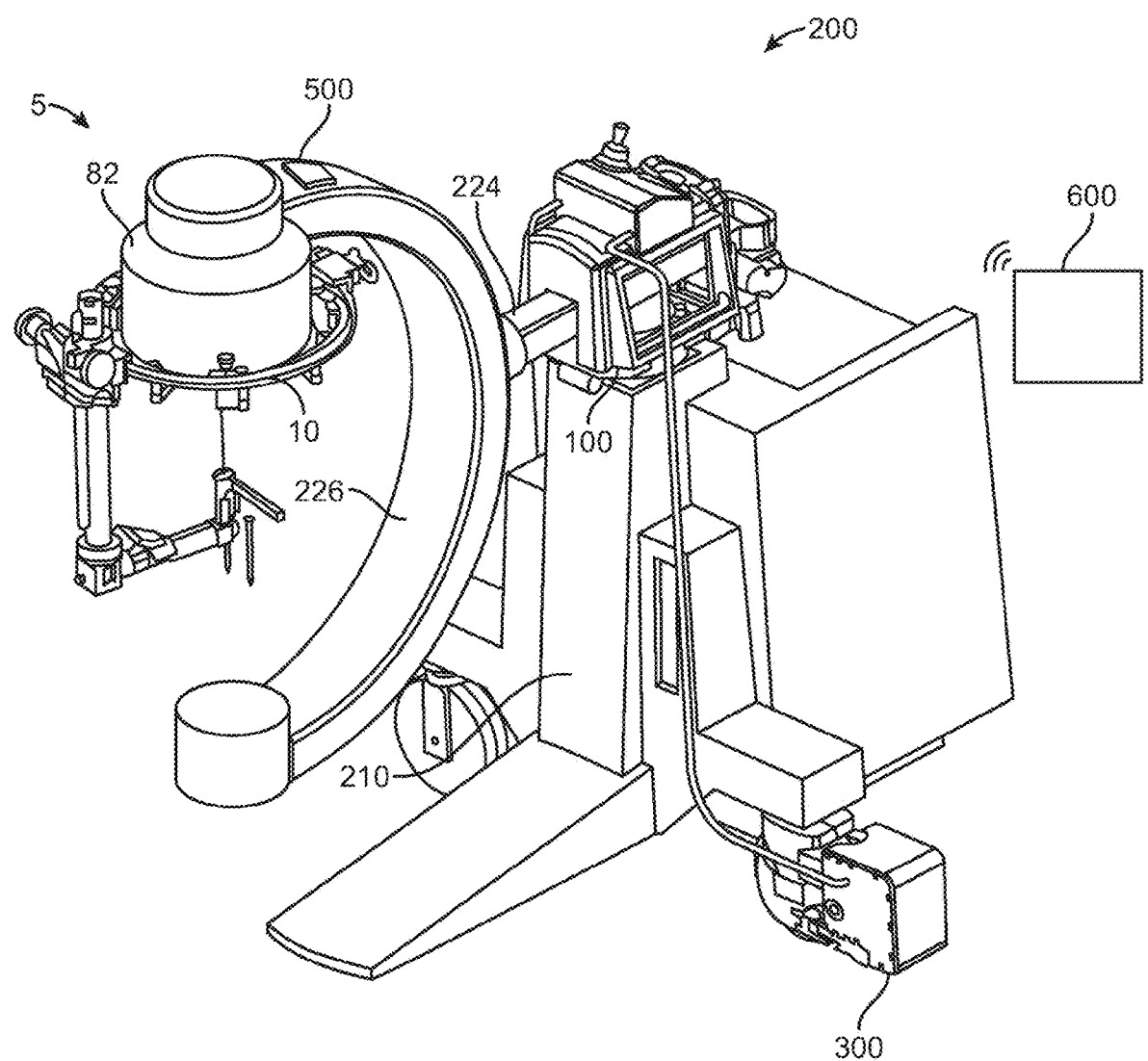
FIG. 1D is a perspective view of a guidance system including at least one electronic positioning device and an imager based object positioner system according to various implementations.
Figure 1E:
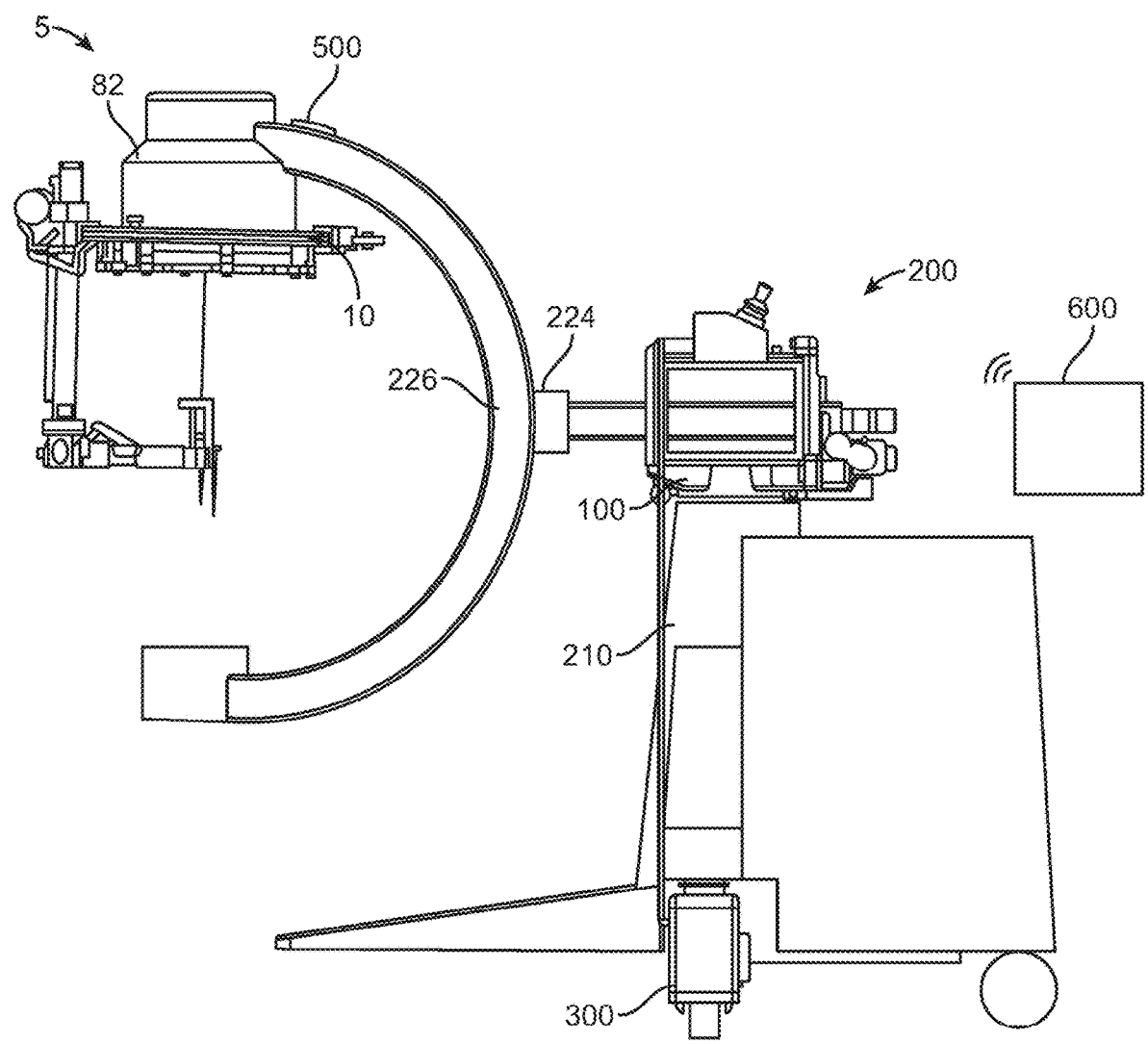
FIG. 1E is a side view of the system of FIG. 1D.

Now with respect to the figures, FIG. 1A is a top view of block diagram of a system 5 that can include one or more of a guidance system 200 including at least one electronic positioning device 100, 300 according to various implementations and an imager based object positioner system 10 according to various implementations. In an implementation, the guidance system 200 can be an image based guidance system. The image based guidance system 200 can include a radiation-based system including a fluoroscope, X-ray machine, or C-Arm 226. As shown in FIGS. 1B-1E, an electronic positioning device 100 can be coupled to a guidance system 200 boom 224. As also shown in FIGS. 1B-1E, an electronic positioning device 300 can be coupled to a guidance system 200 chassis 210. The guidance system 200 can also include a power system 400 having one or more batteries that may supply power to the electronic positioning device 100 or 300. In an implementation, the electronic positioning device 300 can be rotatably coupled to the guidance system chassis 210. The electronic positioning device 100 can be rotatably coupled to the guidance system 200 via a boom 224 base or pedestal 220. The system 5 can include one or more sensors 500 configured to aid in measuring angles of slope or tilt of one or more components of the image based guidance system 200. In some implementations, the C-Arm 226 can include one or more inclinometers configured to measure angles of tilt of the C-Arm 226 with respect to gravity. As will be discussed in more detail below, the one or more inclinometers can be included to provide data related to orientation in at least one and preferably at least two planes. The data from the sensors 500 can be transmitted (either wired or wirelessly via a transmitter) to a computing device 600 having a graphical user interface, as will be discussed in more detail below.

Electronic Positioning Devices

Figure 2A:
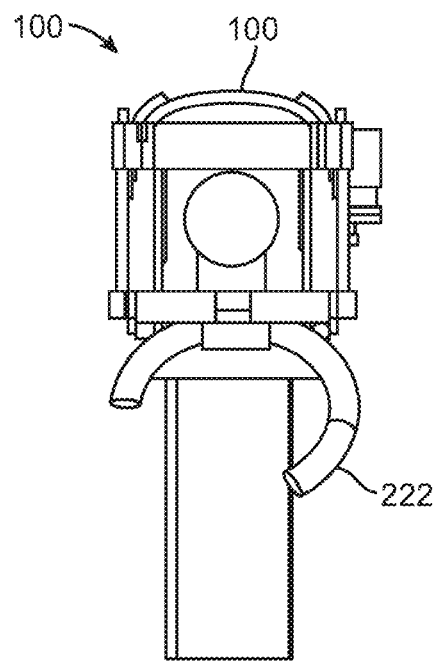
FIG. 2A is a back view of a boom electronic positioning device according to various implementations.
Figure 2B:
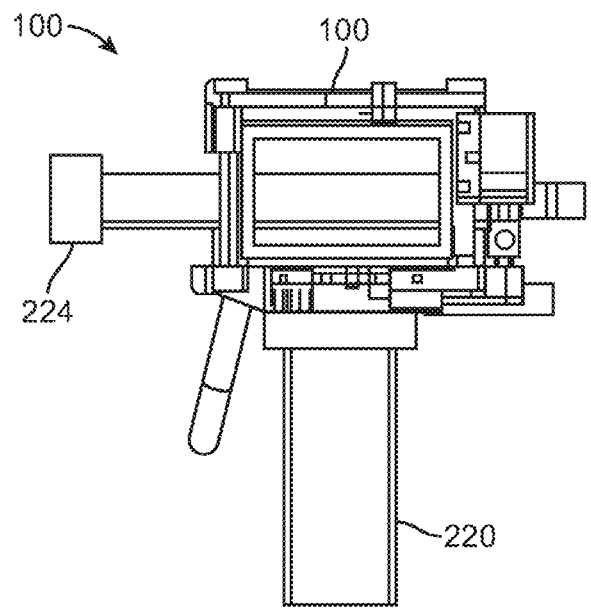
FIG. 2B is a side view of a boom electronic positioning device according to various implementations.
Figure 2C:
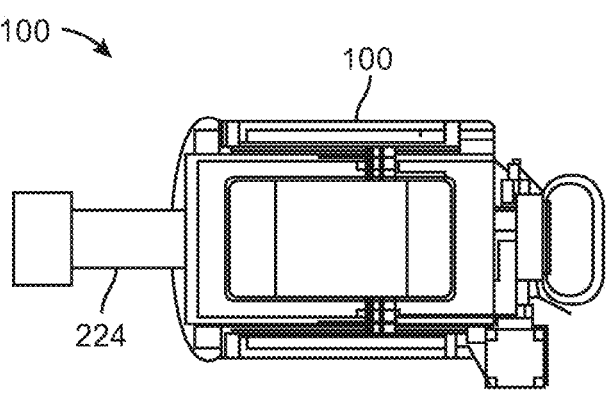
FIG. 2C is a top view of a boom electronic positioning device according to various implementations.
Figure 2D:
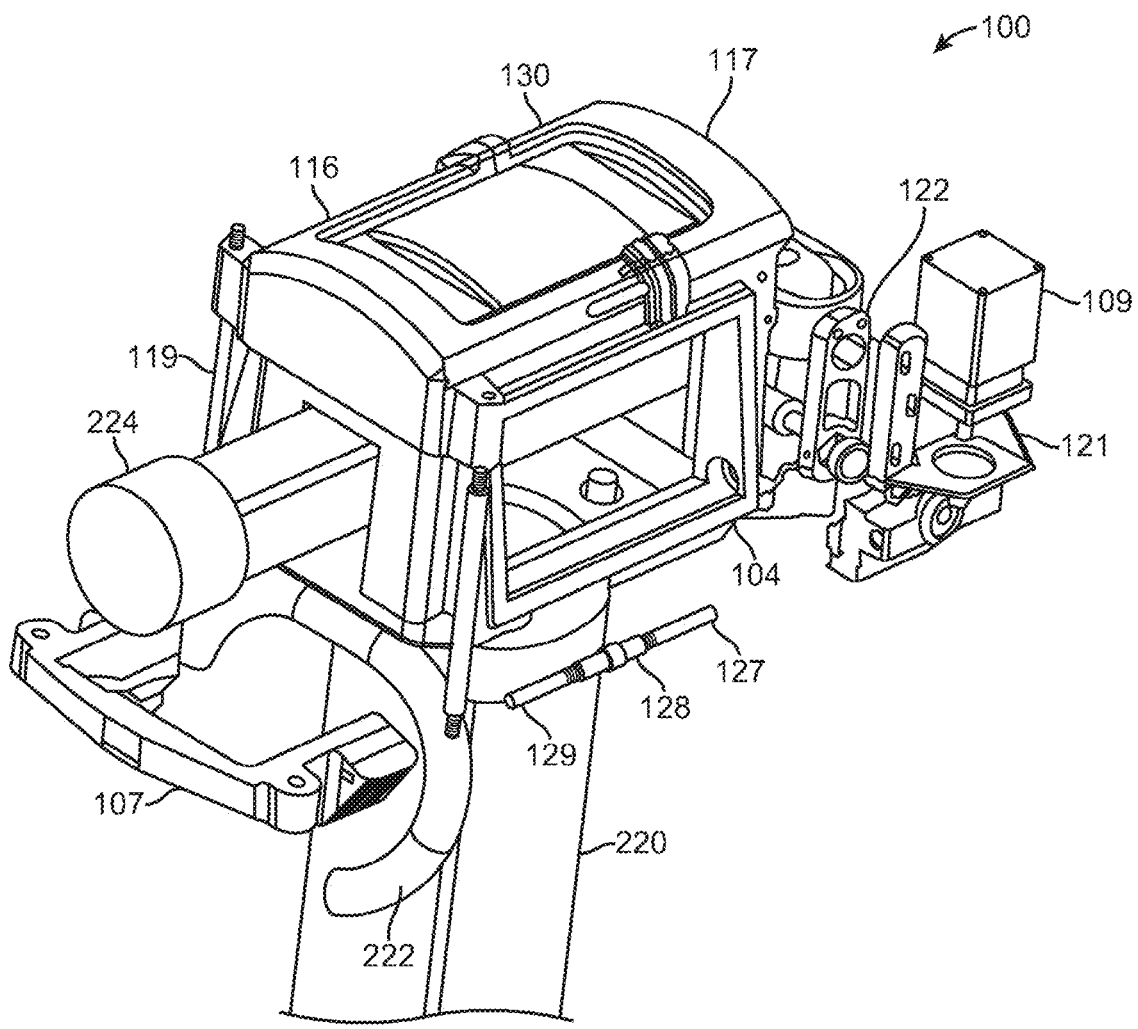
FIG. 2D is an isometric front side, partially exploded view of a boom electronic positioning device according to various implementations.
Figure 2E:
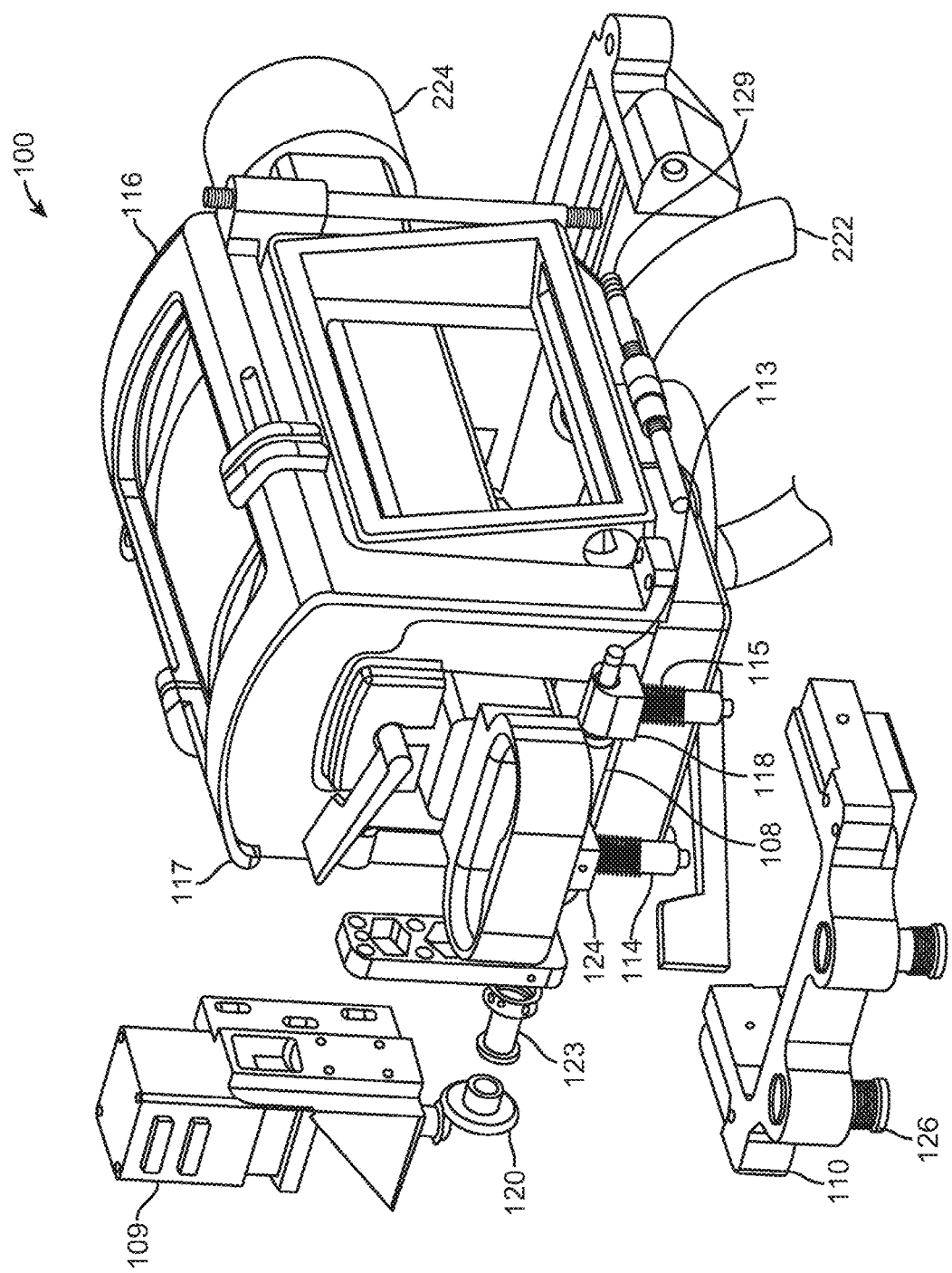
FIG. 2E is an isometric back side, partially exploded view of a boom electronic positioning device according to various implementations.
Figure 3A:
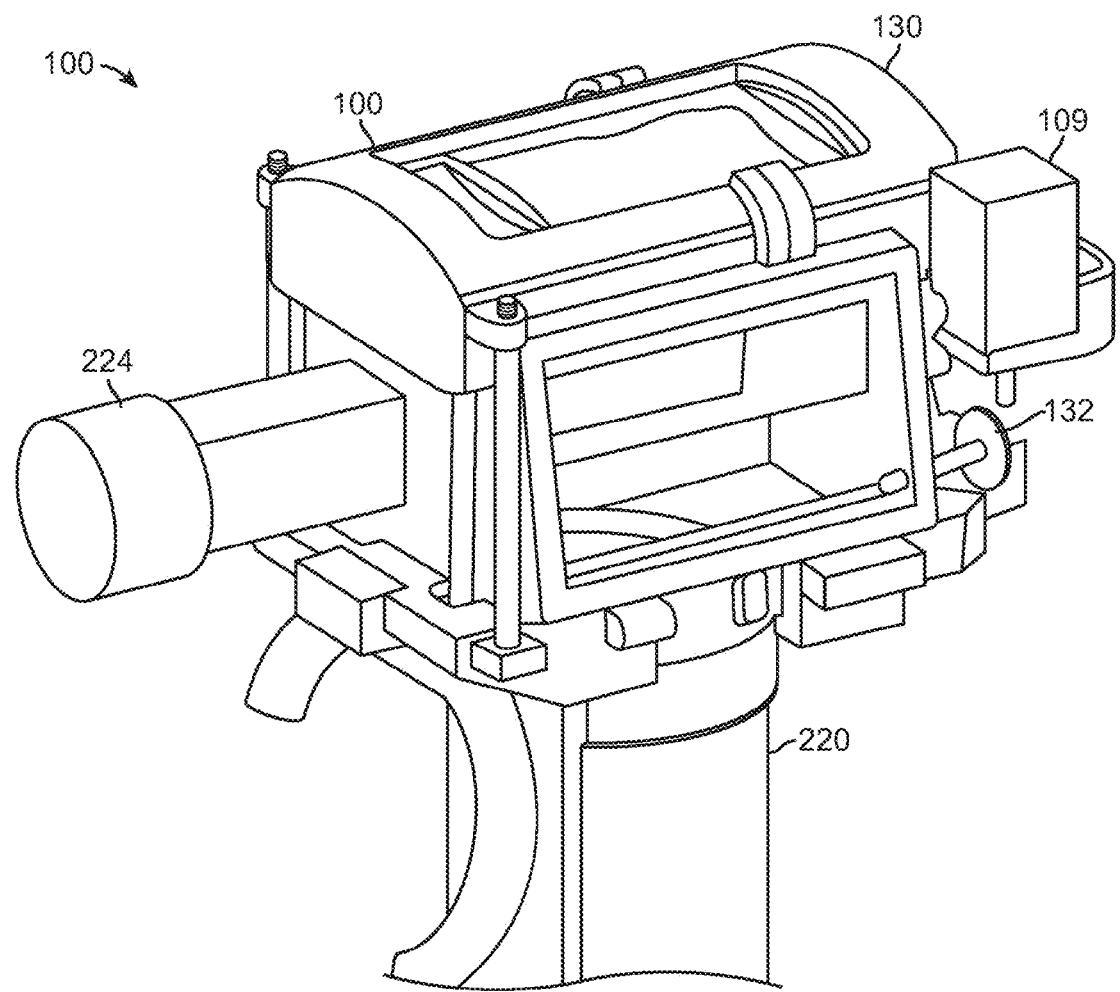
FIG. 3A is an isometric side view of a boom electronic positioning device according to various implementations.
Figure 3B:
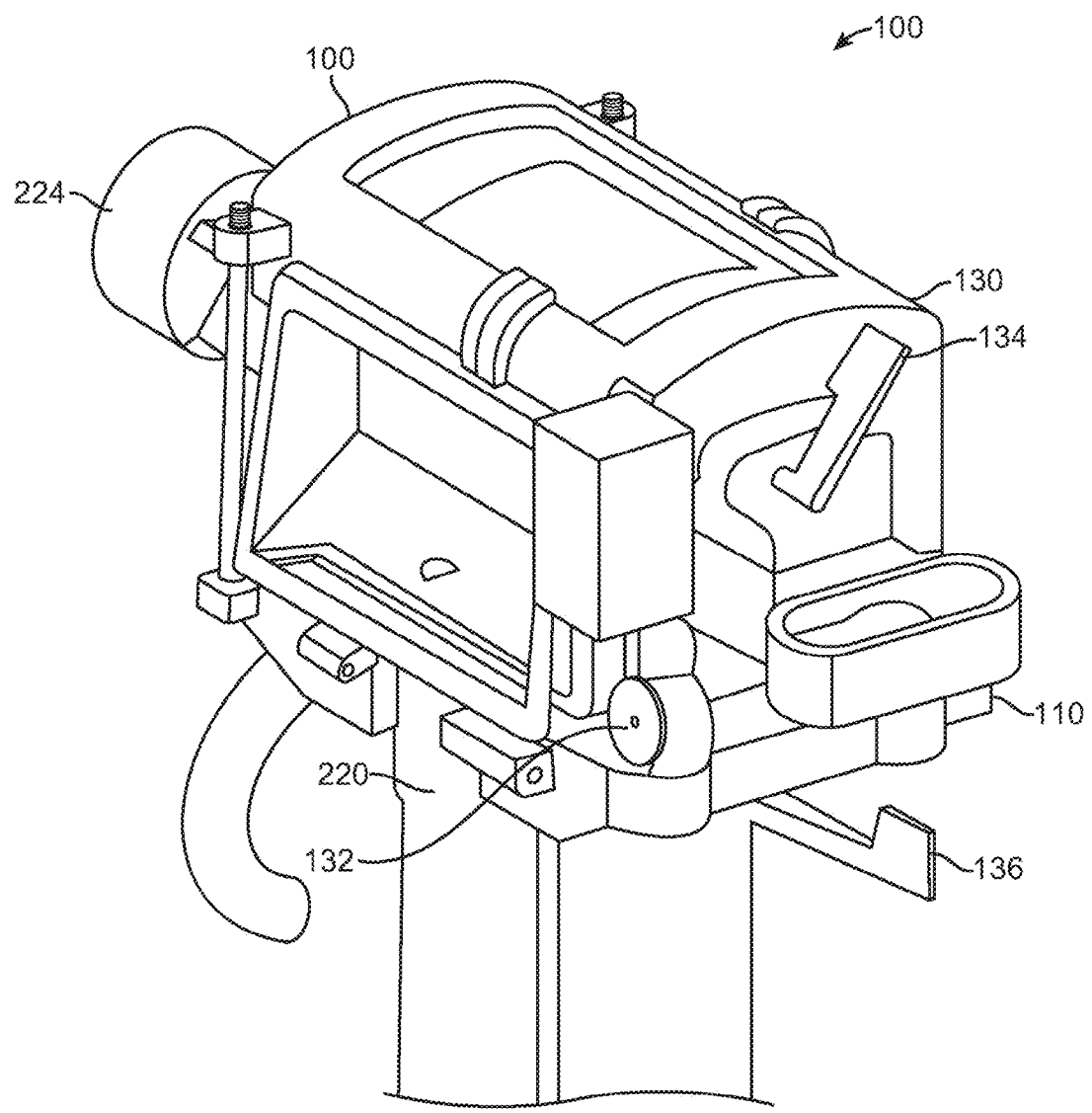
FIG. 3B is an isometric back view of a boom electronic positioning device according to various implementations.
Figure 3C:
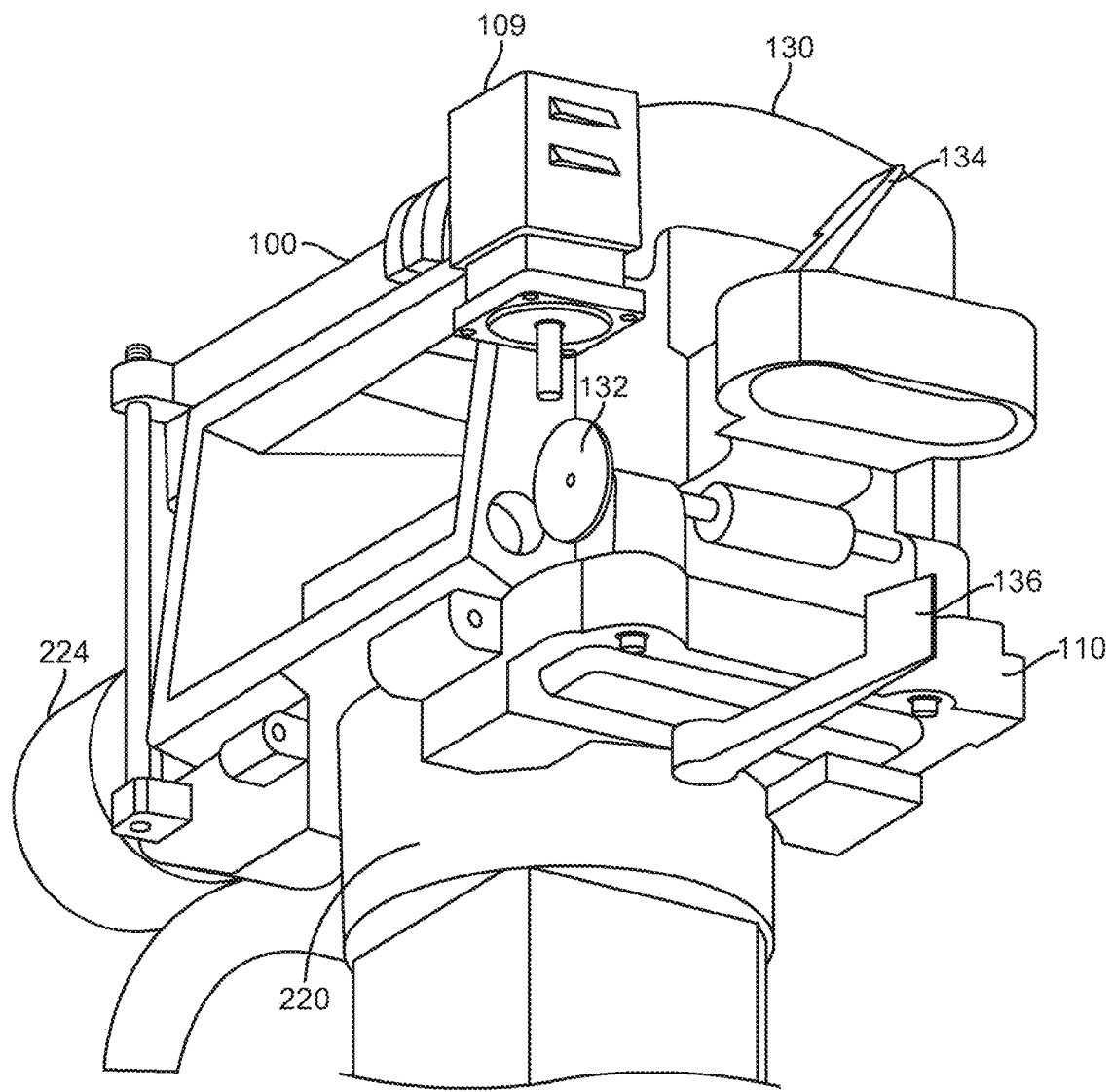
FIG. 3C is an isometric lower back view of a boom electronic positioning device according to various implementations.
Figure 3D:
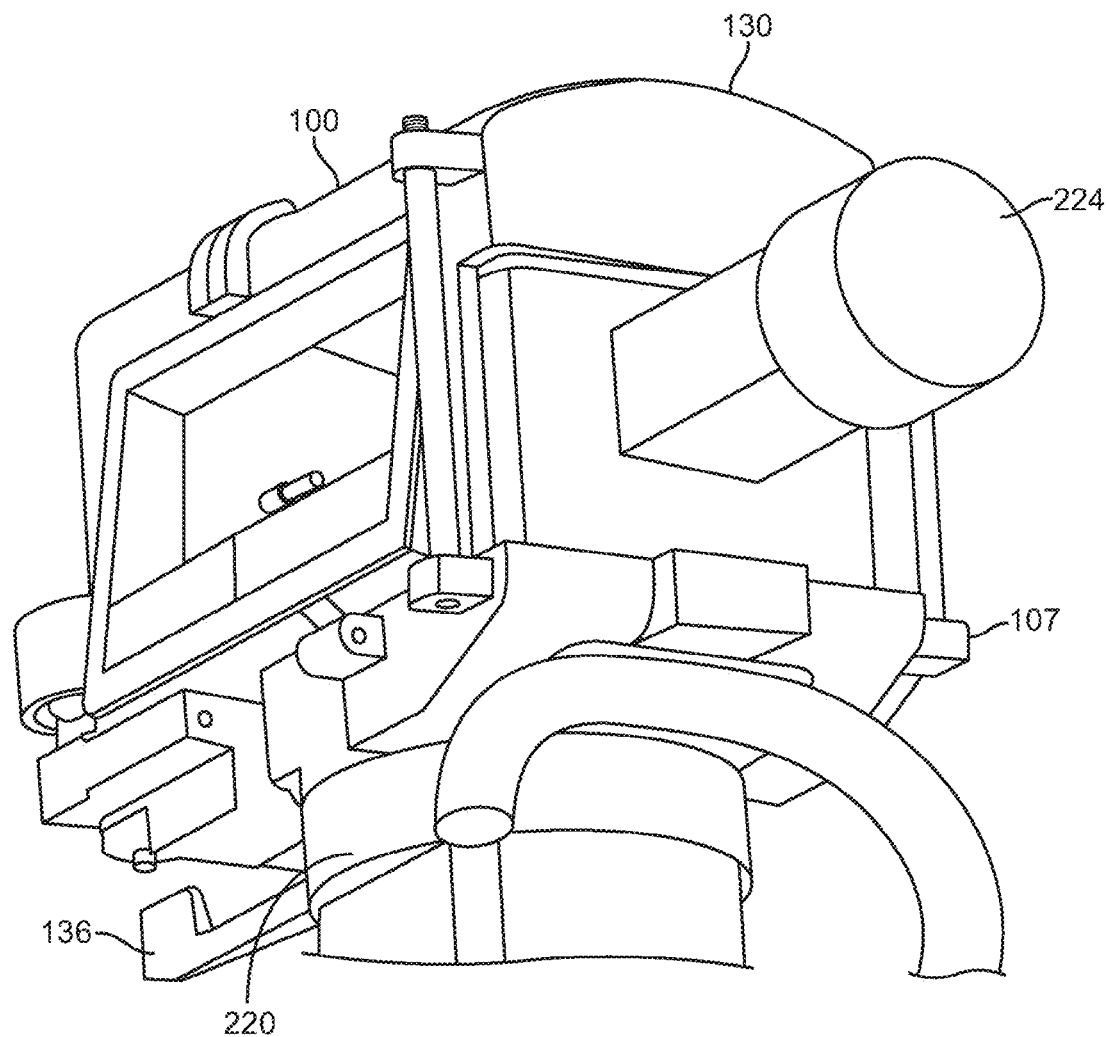
FIG. 3D is an isometric lower front view of a boom electronic positioning device according to various implementations.
Figure 3E:
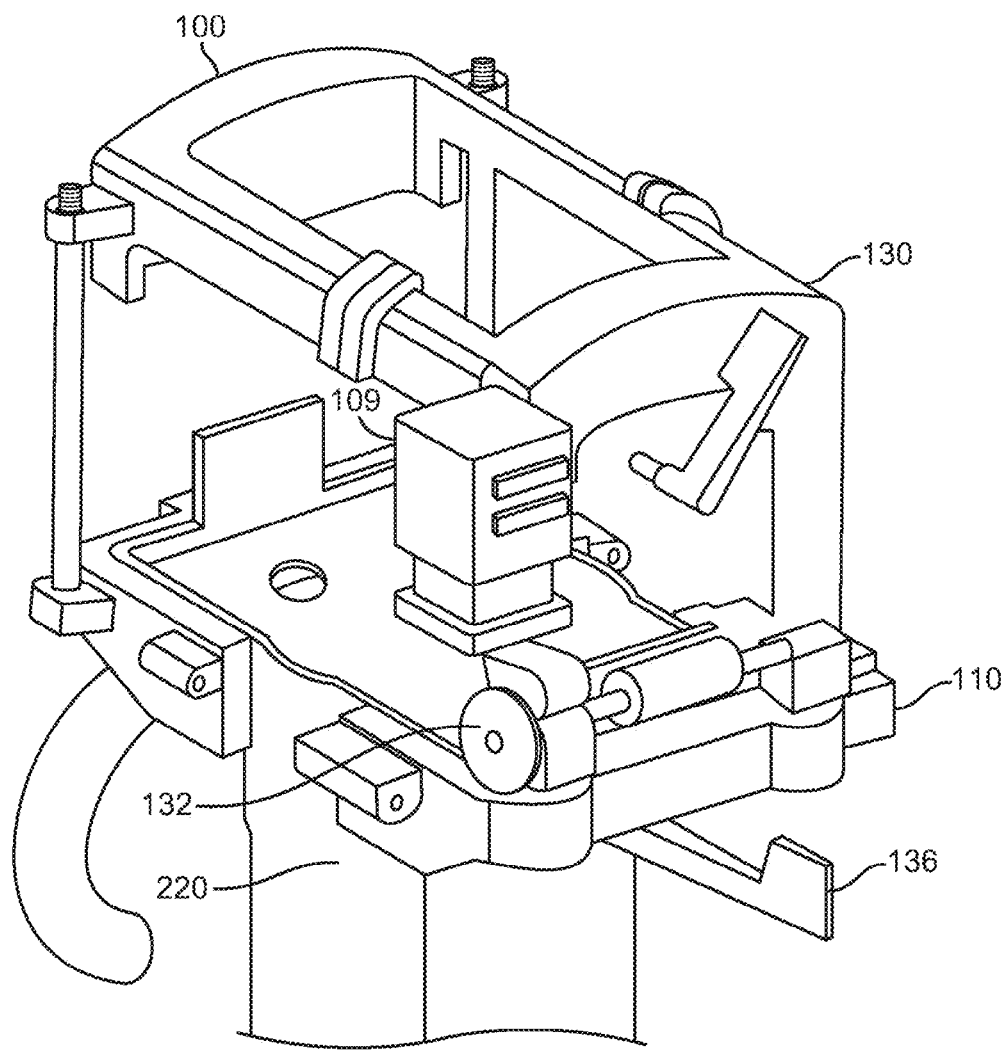
FIG. 3E is a partial isometric back view of a boom electronic positioning device according to various implementations.
Figure 3G:
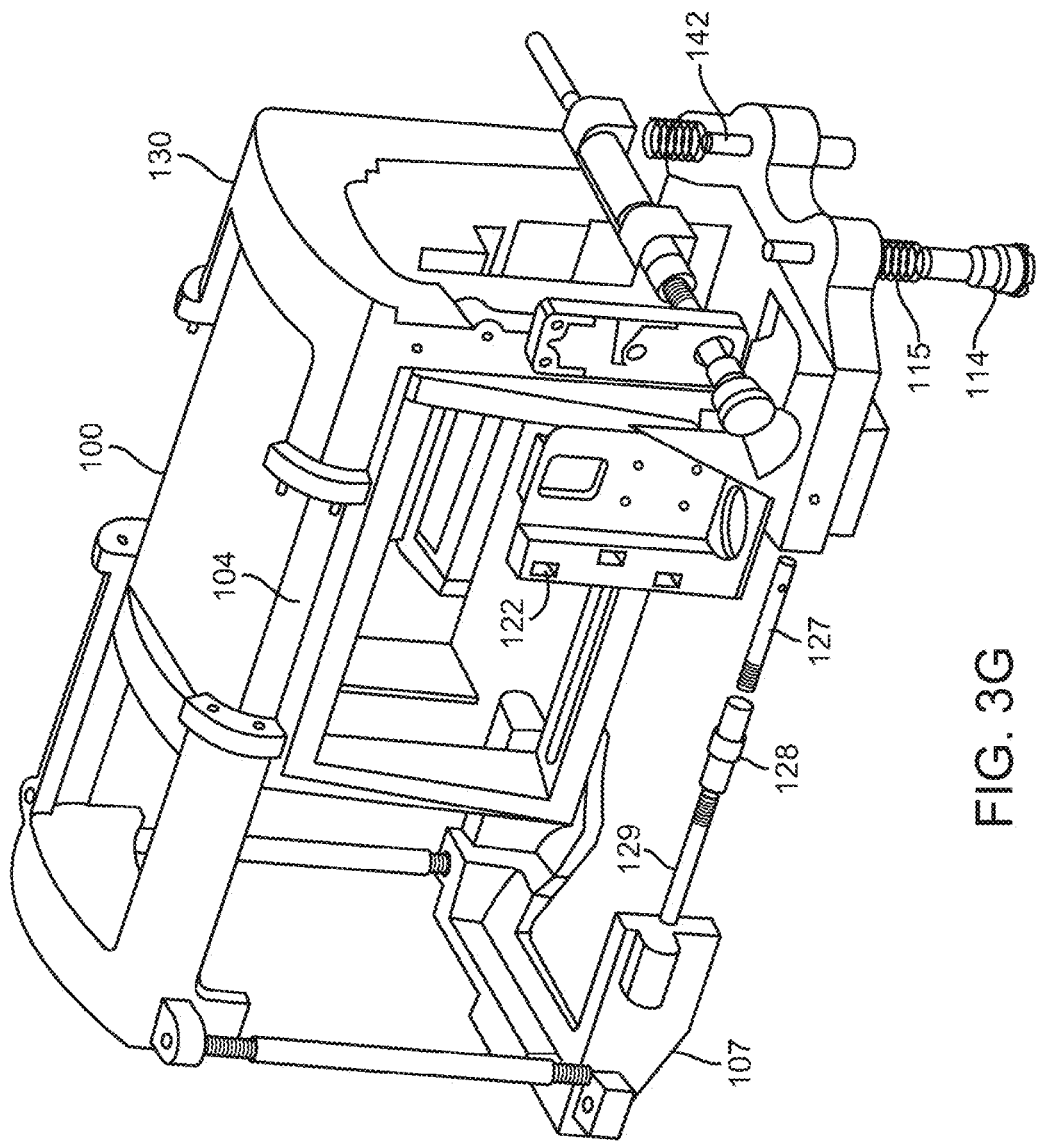
FIG. 3G is an exploded side view of a boom electronic positioning device according to various implementations.
Figure 3H:
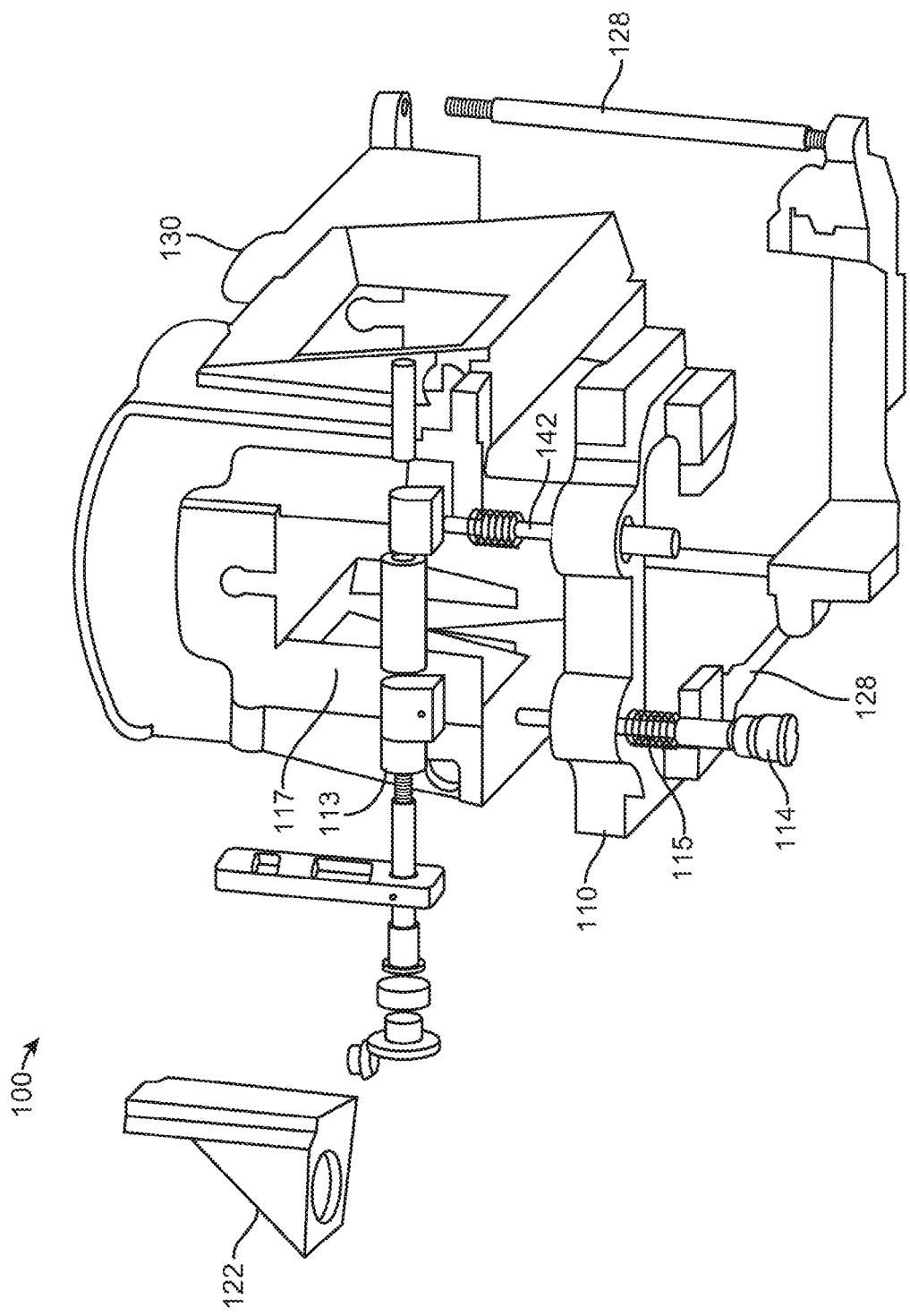
FIG. 3H is an exploded rear view of a boom electronic positioning device according to various implementations.
Figure 3I:
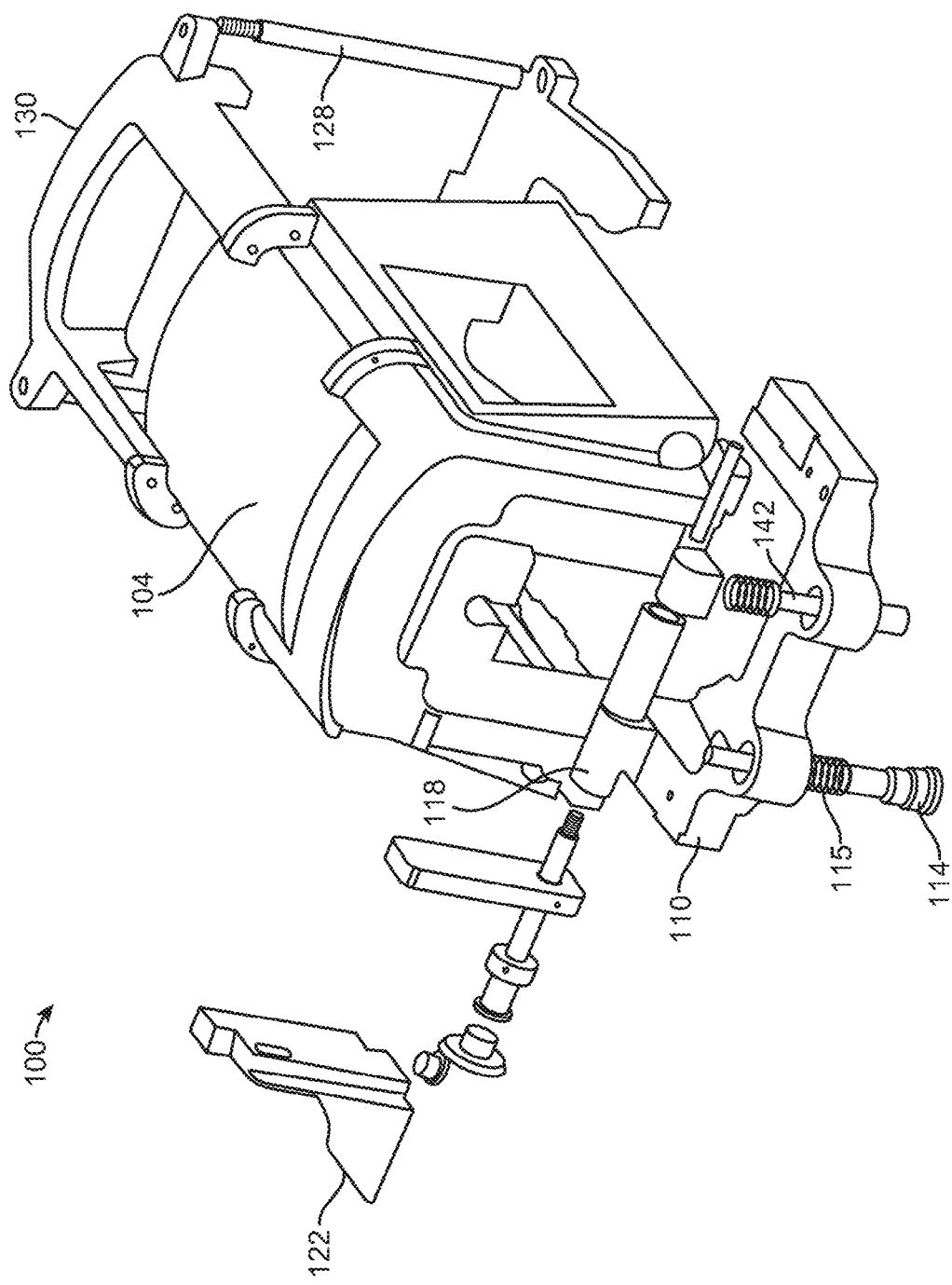
FIG. 3I is an exploded rear, top view of a boom electronic positioning device according to various implementations.

FIGS. 2A to 3I are diagrams of the electronic positioning device 100 couplable to a guidance system boom 224. FIG. 2A is a back view, FIG. 2B is a side view, FIG. 2C is a top view, FIG. 2D is an isometric front side, partially exploded view, FIG. 2E is an isometric back side, partially exploded view, FIG. 3A is an isometric side view, FIG. 3B is an isometric back view, FIG. 3C is an isometric lower back view, FIG. 3D is an isometric lower front view, FIG. 3E is a partial isometric back view, FIG. 3F is a partial exploded back view, FIG. 3G is an exploded side view, FIG. 3H is an exploded rear view, and FIG. 3I is an exploded rear, top view of a boom electronic positioning device 100 according to various implementations.

As shown in these figures, the boom-couplable electronic positioning device 100 can include a main housing or chassis 130 that couples a motor-driven boom roller 109 to the boom 224. The positioning device 100 can include an internal housing 104, boom clamp 107, motor mount 121, standoff clamp 119, upper front clamp 116, superior distal boom clamp 117, arm bearing support 122, turnbuckle 128 having a right shaft 127 and left shaft 129, posterior arm roller 113, roller arm 118, linear ball bearings 114, journal fittings 124, Teflon® bearings 123, gear bevel 120, aft boom clamp 110, boom journal 126, spring 115, motor gear 132, boom locking arm 134, base locking arm 136, and shaft 142. In an implementation, the boom locking arm 134 can securely engage the boom 224. The base locking arm 136 can lock the pedestal or boom base 220. The boom 224 can be adjustable along its axis and lockable via the boom lock lever or boom locking arm 134. The boom 224 can be rotatable on a pedestal/base 220 where the pedestal/base 220 can be lockable via a pedestal locking lever or base locking arm 136. The positioning system 100 may include an upper chassis 116 and a lower chassis 107 coupled together via one or more adjustable connecting rods 128.

A motor 109 may be coupled to the drive gear 132 where the motor 109 and drive gear 132 can be coupled to the chassis 104. The drive gear 132 may be coupled to a roller 108 that engages a section of the boom 224. The roller 108 can be coupled to the lower chassis 107 via extensions 142, springs 115, and bolts 114. In an implementation, the motor 109 can be a DC motor including a Parker™ IBE320 Servo DC motor. The gear 132 can be a 2 to 1 two bevel gear. The roller 108 can be a polyurethane roller. In an implementation the motor 109, gear 132, and roller 108 are placed opposite the operation field of the guidance system 200.

In an implementation the chassis 130, 107, 110 can include four clamping posts 128, 119. The lower chassis can include two segments 107, 110 coupled together via connectors 128 such as turn buckle draw bars. The upper chassis 130 can be coupled to the lower chassis via connectors 119 such as standoffs. In an implementation, emergency stop controls can be placed on opposite sides of the chassis 130, 107, 110. In an implementation the roller 108 can coupled to the gear 132 via a shaft 142 coupled to the extensions 118 and blocks 113. In an implementation, the blocks can include bronze and other linear bearings 114.

Figure 4D:
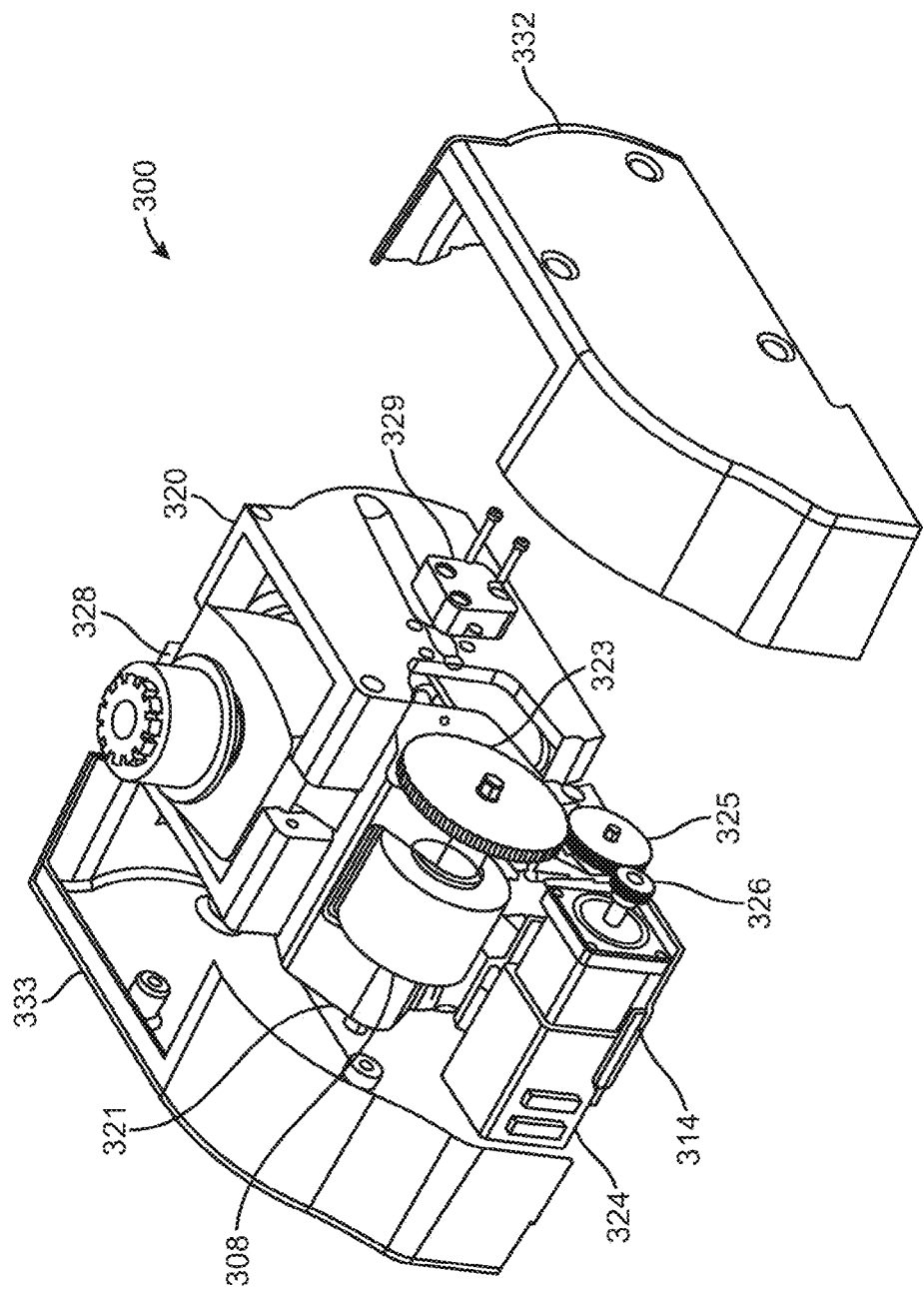
FIG. 4D is an exploded side view of a chassis based electronic positioning device according to various implementations.
Figure 4E:
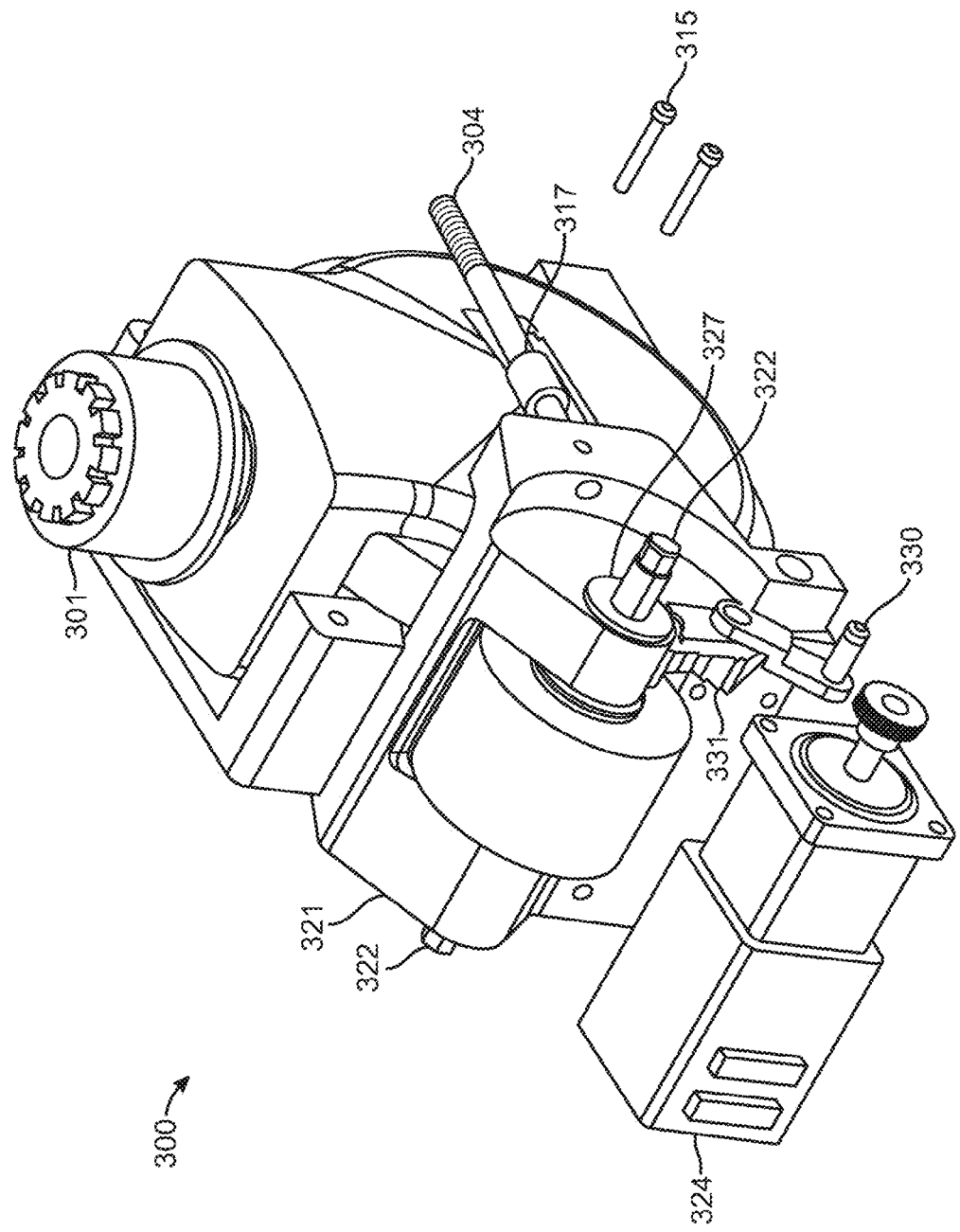
FIG. 4E is another exploded side view of a chassis based electronic positioning device according to various implementations.

FIGS. 4A to 4E are diagrams of an electronic positioning device 300 that can coupled to a rotatable chassis wheel 340 of a guidance system 200 chassis 210. The wheel 340 can be coupled to the guidance system via a caster 301. In an implementation, the wheel 340 can be part of the device 300. FIG. 4A is a back view, FIG. 4B is a side view, FIG. 4C is a top view, FIG. 4D is an exploded side view, and FIG. 4E is another exploded side view of the chassis based electronic positioning device 300 according to various implementations. The chassis based electronic positioning device 300 can include a left cover 333, right cover 332, caster wheel 301, wheel 340, left clam shell 320, right clam shell 328, block housing 329, drive 323, idler gear 325, driver gear 326, motor mount 314, DC motor 324, roller 308, gear head 321, roller shaft 322, cam follower 331, idler arm 330, flange 327, screws 315, linear ball bearings 317, and guide shaft 304.

In an implementation, the motor 324 can be a DC motor including a Parker™ IBE320 Servo DC motor. The drive gear 323 can be a 2 to 1 two bevel gear. The roller 308 can be a polyurethane roller. The electronic positioning device 100, 300 can be compatible with the commonly utilized image intensifier devices, including the GE/OEC model 9800 image intensifier. The devices 100, 300 can provide simple, controlled, and intuitive movement of the image intensifier along at least two axes, for example. In an implementation the axes can be orthogonal or perpendicular such as representing an X and a Y axis.

Again with respect to FIG. 1A, the electronic positioning devices 100, 300 can be coupled to a controller 230 having a user interface including a plurality of inputs 232 and outputs. The controller 230 can be coupled to a device 100, 300 via one or more wires 234 or via a wireless protocol. The controller 230 can enable a user to operate the devices 100, 300 from up to at least 10 meters from the system 200. The controller 230 inputs 232 may enable a user to translate or move the boom 224 or chassis 210 in micro and macro increments. In an implementation, the devices 100, 300 can move the boom 224 or chassis 210 1 mm upon each controller 230 activation. The boom 224 can have at least 3 cm of excursion in either direction along its axis (at least 6 cm total). The devices 100, 300 may also be operated by a foot switch 236 where the foot switch can override the controller 230 in an implementation.

The foot switch 236 and controller 230 can be hermetically sealed or have sterilely accessible controls. When not active each device 100, 300 can disengage (the boom 224 or wheel 340) to allow unrestricted movement of the system 200. When active each device 100, 300 can engage (the boom 224 or wheel 340) to prevent movement of the system 200. Each device 100, 300 can allow varied rates of movement, e.g. as a device 100, 300 is activated for a predetermined time interval the movement rate can linearly increase.

Imager Based Object Positioner System

Figure 5A:
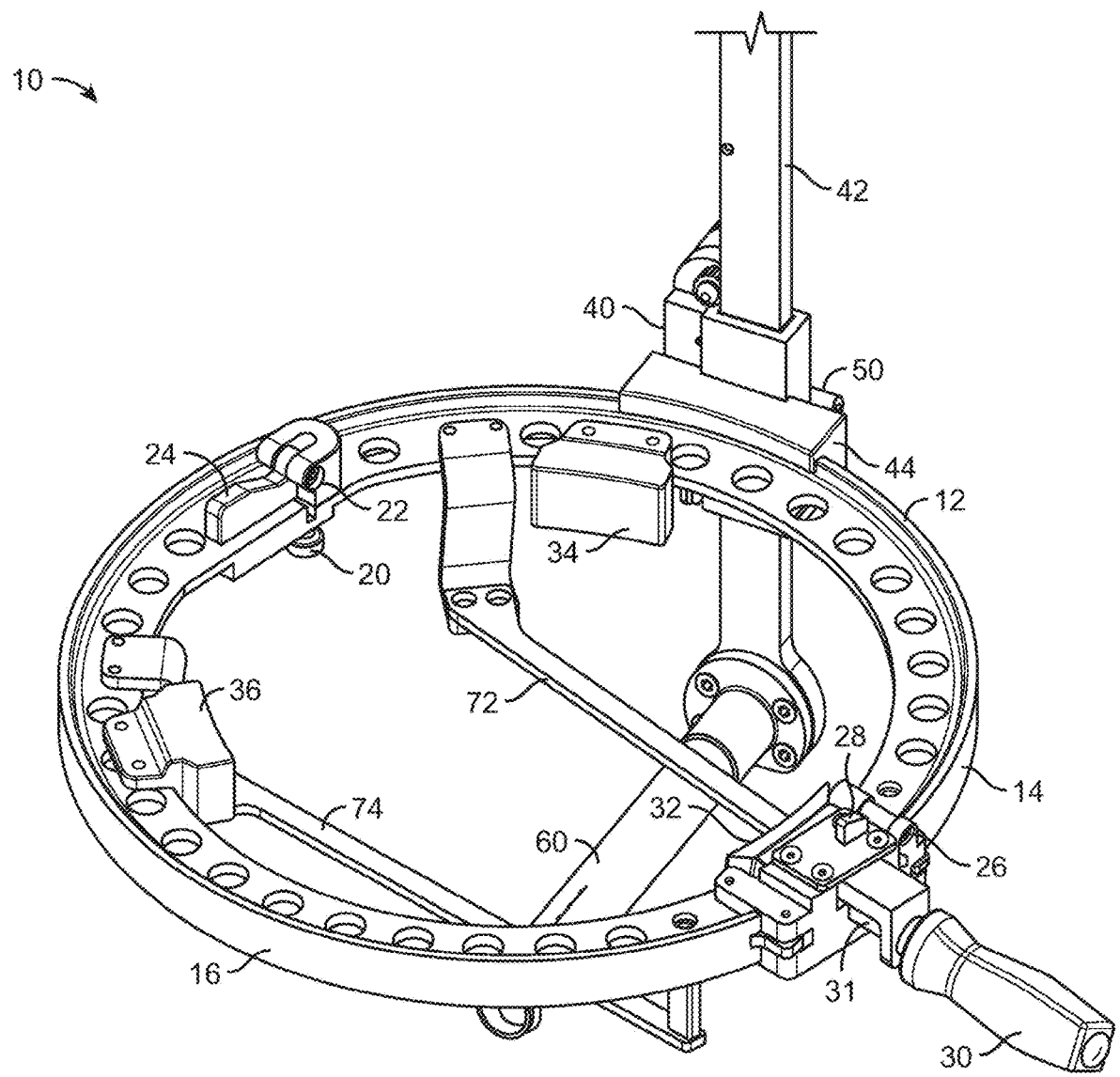
FIG. 5A is an isometric view of an imager based object positioner system.
Figure 5B:
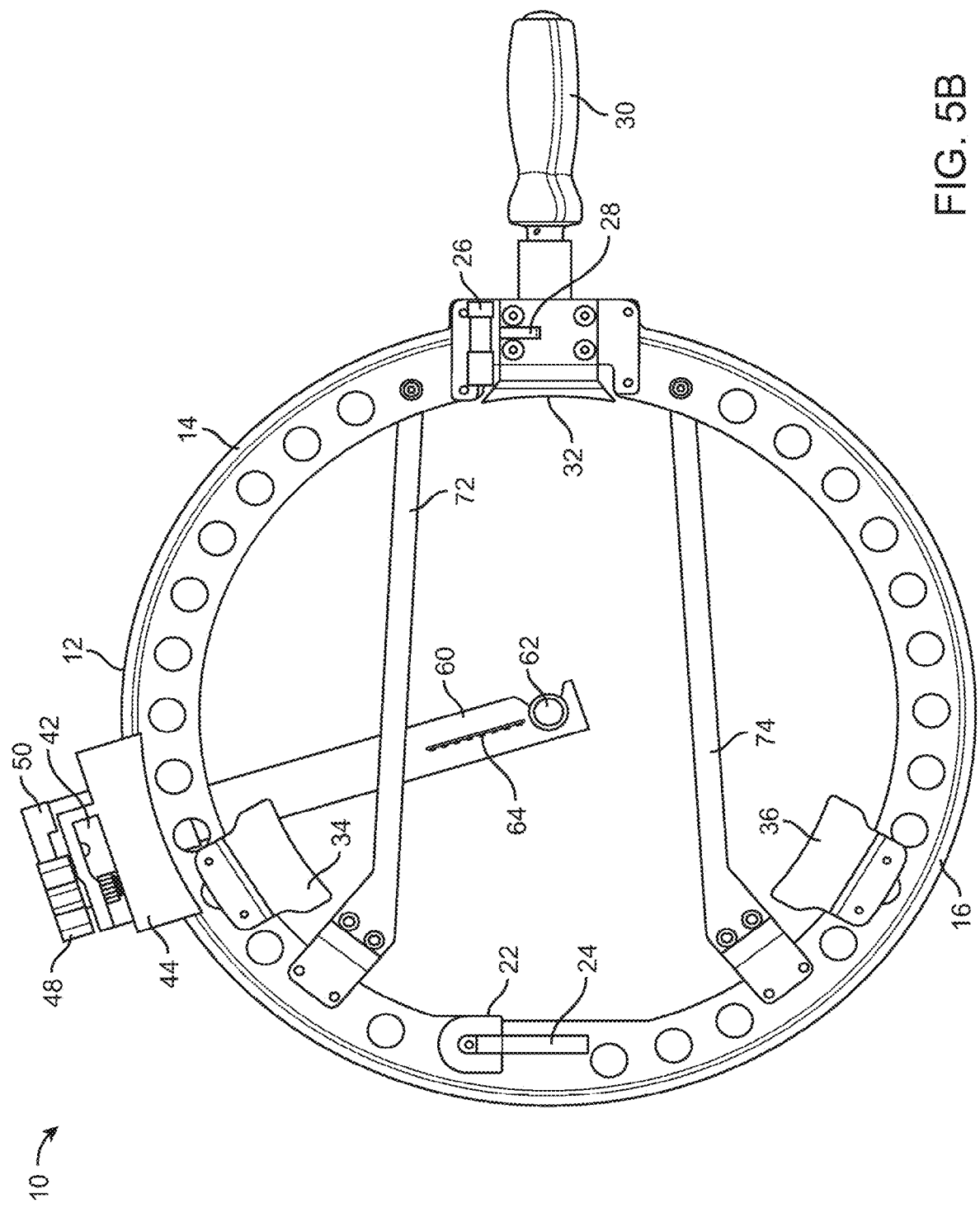
FIG. 5B is a top view of the imager based object positioner system shown in FIG. 5A.
Figure 5C:
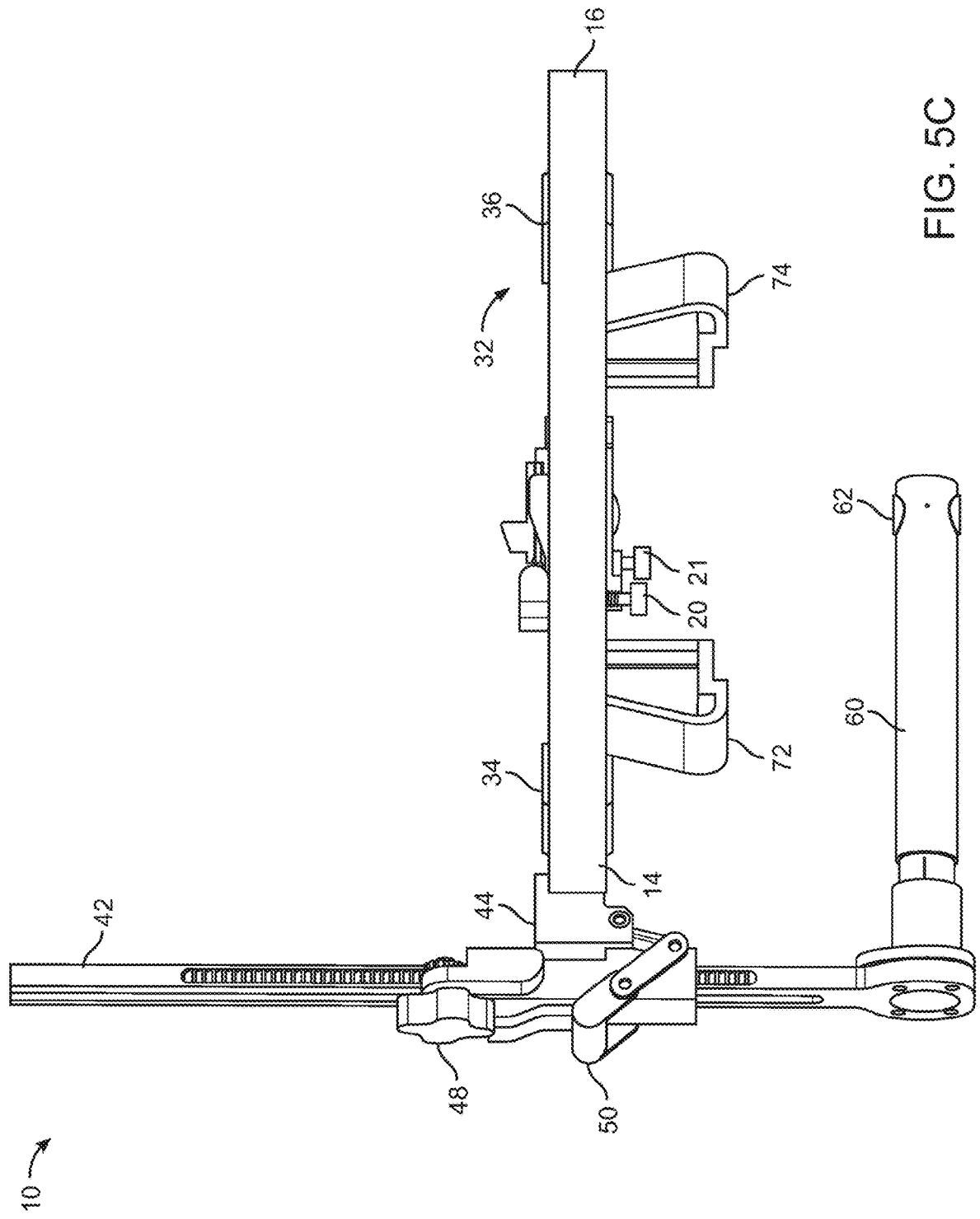
FIG. 5C is a side view of the imager based object positioner system shown in FIG. 5A.

FIG. 5A is an isometric view, FIG. 5B is a top view, and FIG. 5C is a side view of an imager based object positioner system 10. The imager based object positioner system 10 can include a first rail section 14, a second rail section 16, a moveable clamp 32, immoveable camps 34, 36, a vertical offset mechanism 40, and placement/stabilizer bars 72, 74. The first rail section 14 can be coupled to the second rail section 16 via two releasable hinges 22, 26. A handle 30 can be coupled to the moveable clamp 32 and screw 31. Three clamps 32, 34, 36 can be used to engage a transmitter 82 of an imager 80. The imager 80 can be an imager intensifier system including an image intensifier or receiver supported by a C-Arm 226 in a mobile digital fluoroscope.

The releasable hinge 22 can include a release mechanism 20 and limiter 24 and the releasable hinge 26 can include a release mechanism 21 and limiter 28. The vertical offset mechanism or apparatus 40 can include a releasable car 44, vertically translatable arm 42, car release assembly 50, and guide boom 60. The car 44 can releasably engage the circular rail 12 formed by the two rail sections 14, 16. The car 44 can be move along the rail 12 when the car release assembly 50 is disengaged. The boom 60 can be coupled to a distal end of the arm 42 and can include an object mounting bushing/guide bushing 62.

Figure 6A:
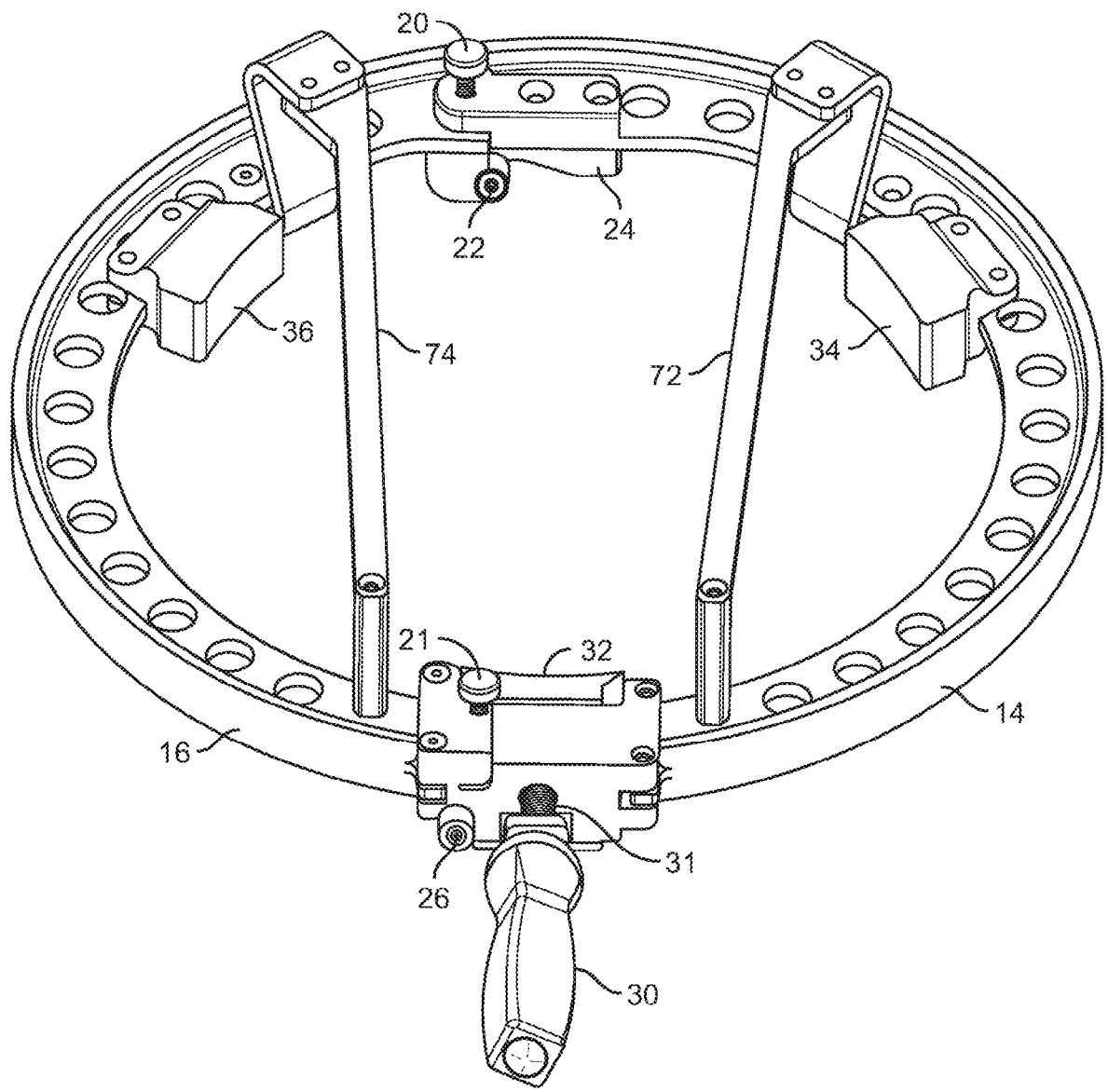
FIG. 6A is a bottom view of an imager based object positioner system.
Figure 6B:
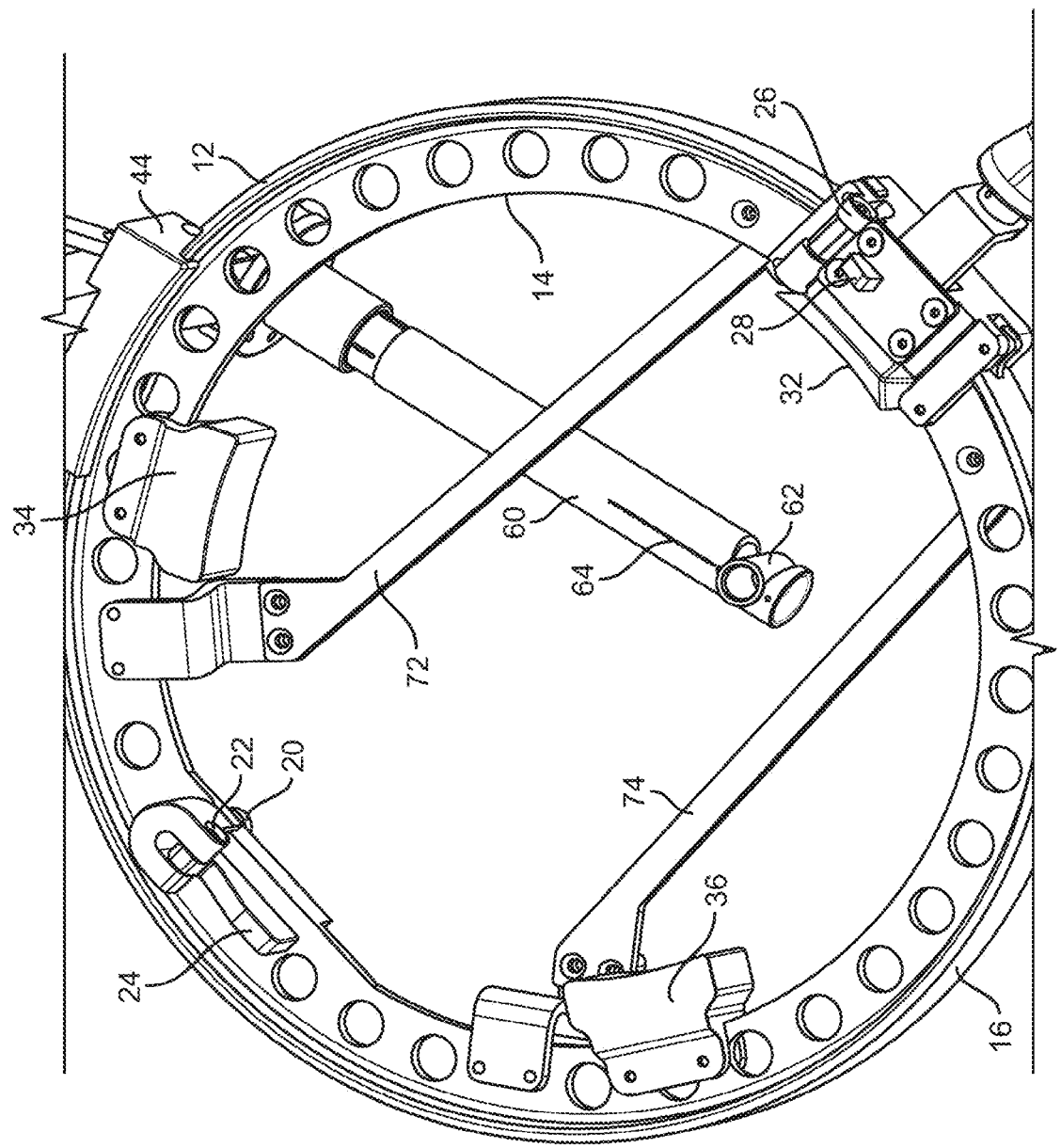
FIG. 6B is a top, partial view of the foldable portion of the imager based object positioner system shown in FIG. 6A.

FIG. 6A is a bottom view of the imager based object positioner system 10 shown in FIG. 5A with the vertical offset mechanism 40 removed. FIG. 6B is a top, partial view of the imager based object positioner system 10 shown in FIG. 6A. FIG. 6C is a top, partial view of a moveable clamp mechanism 32 of the imager based object positioner system shown in FIG. 6A. In an implementation the system 10 can be placed over an imager transmitter 82 and the handle 30 engaged to cause the clamp 32 to apply force in conjunction with clamps 34, 36 against the imager transmitter to releasably hold the positioner system 10 to the imager transmitter 80 or receiver. In an implementation, the clamps are about 120 degrees apart from adjacent clamps. In an implementation, the handle 30 can include a torque limiter to prevent possible damage to the imager. In another implementation the position system 10 can include two or more clamps 32, 34, 36 to engage an imager.

Figure 7A:
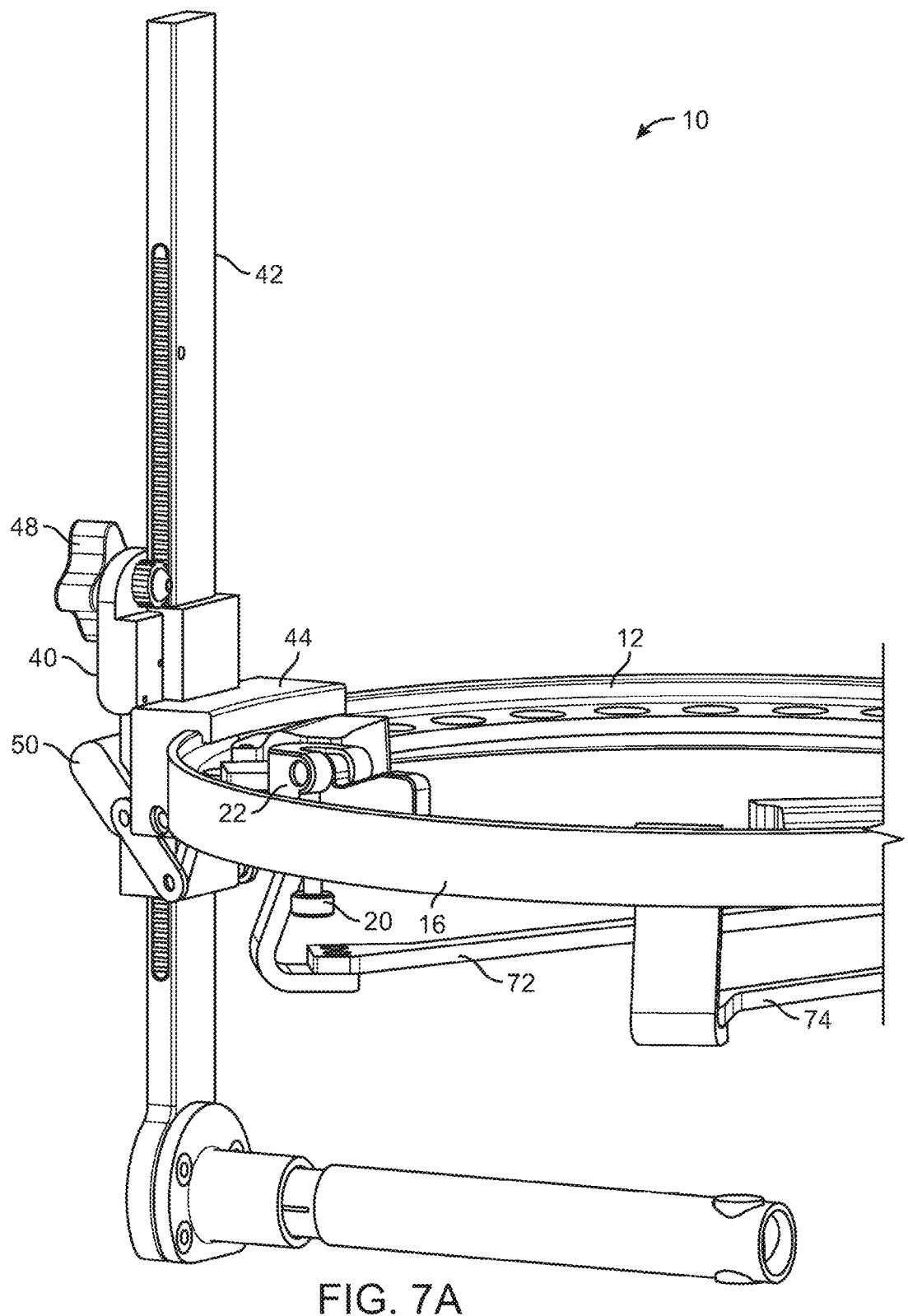
FIG. 7A is a side, partial view of the imager based object positioner system shown in FIG. 5A showing a vertical offset system configuration.
Figure 7B:
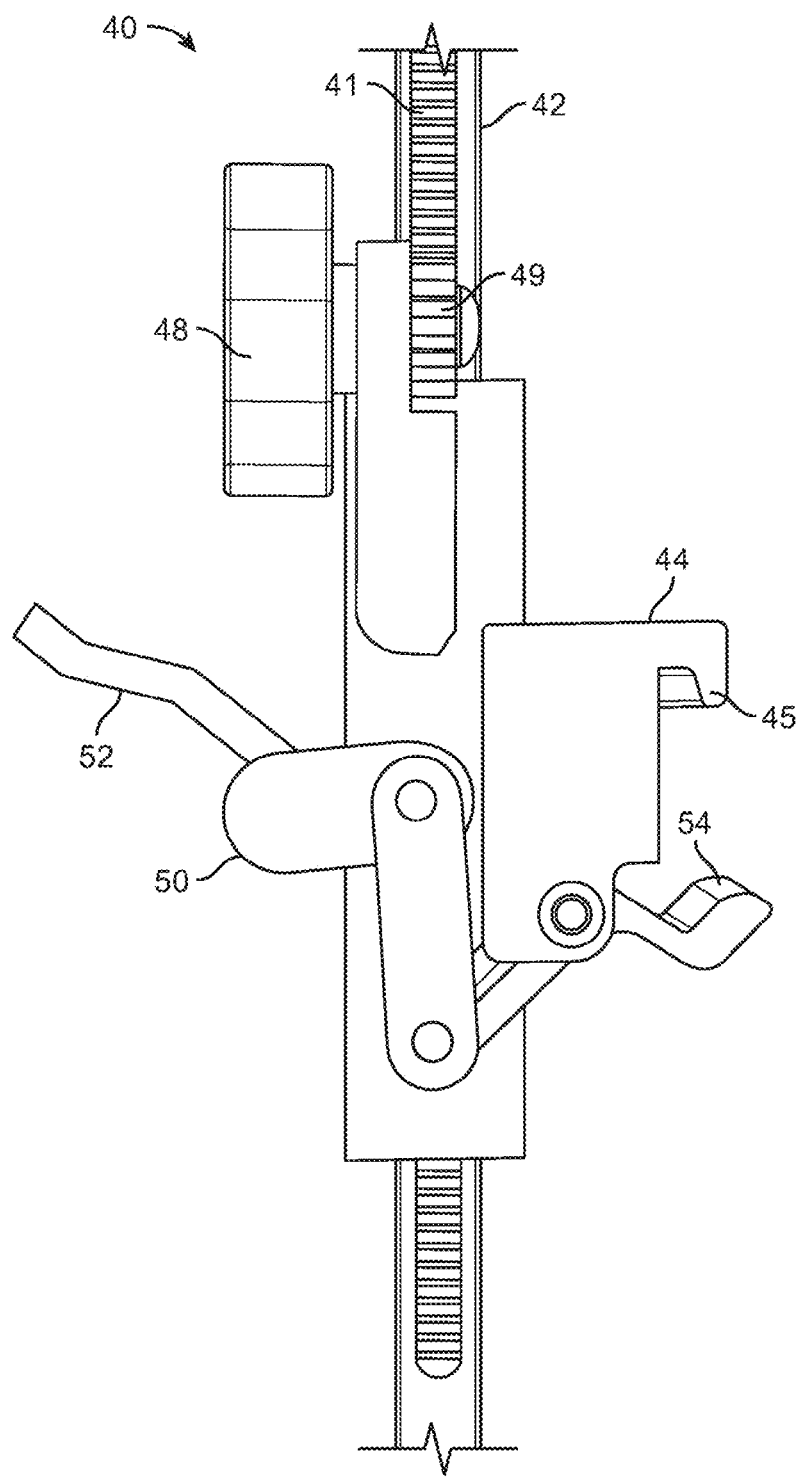
FIG. 7B is a side view of a releasable car system of the vertical offset system shown in FIG. 7A.
Figure 7C:
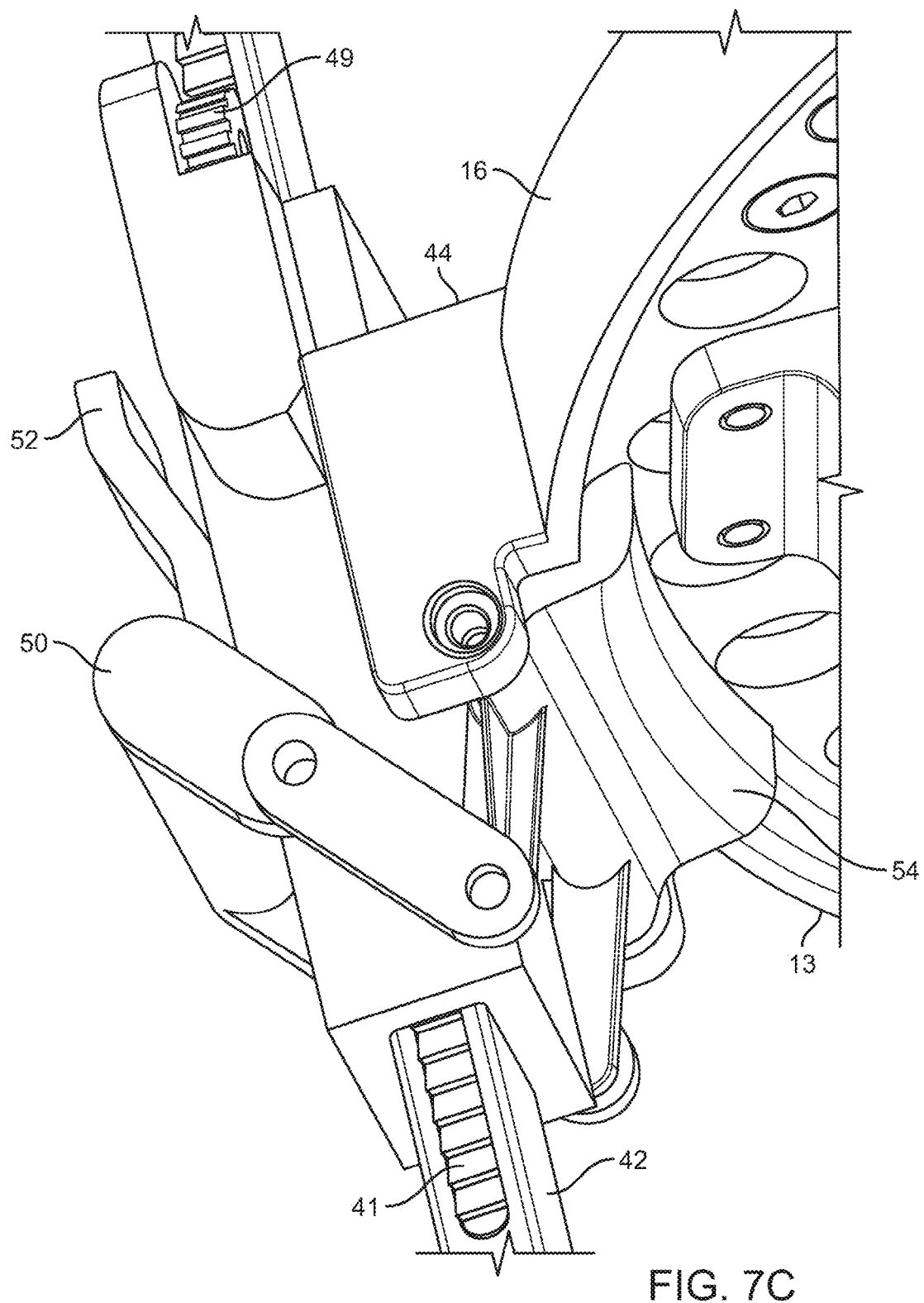
FIG. 7C is an isometric view of the releasable car system of the vertical offset system shown attached to a rail of the foldable section of the imager based object positioner system.

FIG. 7A is a side, partial view of the imager based object positioner system 10 shown in FIG. 5A showing a vertical offset system 40 configuration. FIG. 7B is a side view of a releasable car system 44 of the vertical offset system 40 shown in FIG. 7A. FIG. 7C is an isometric view of the releasable car system 44 of the vertical offset system 40 shown attached to a rail 12 of a foldable section 14 of the imager based object positioner system 10. In an implementation, the car system 44 can include a top rail engagement lip 45, lower track engagement lip 54, car release assembly 50, and release assembly lever 52. In this implementation, the lever 52 can be used to releasably engage the lower rail 13 via the lower track engagement lip 54 and the upper rail 12 via the upper track engagement lip 45.

Figure 7D:
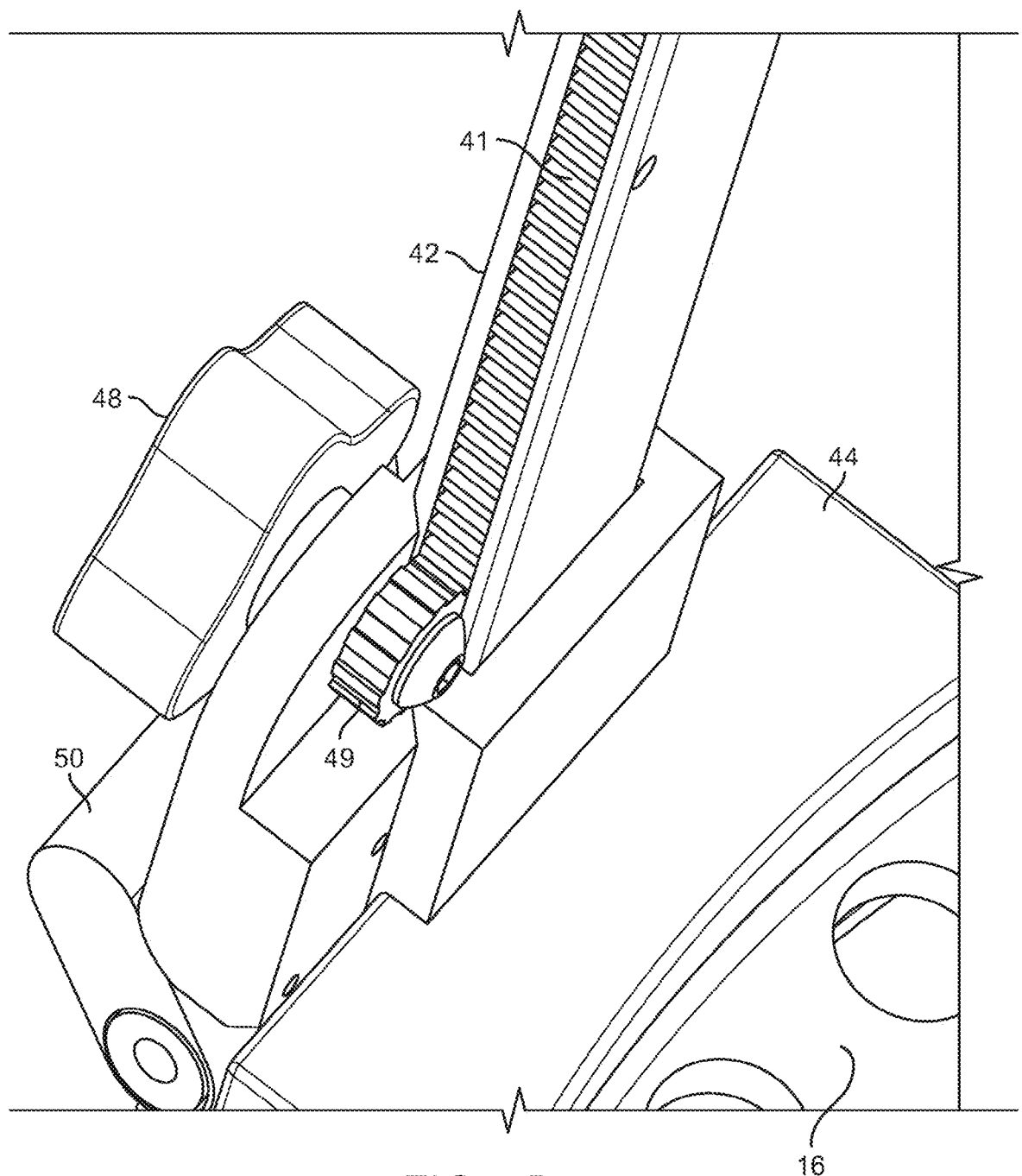
FIG. 7D is an isometric, top view of a vertical level adjustment mechanism of the vertical offset system shown attached to a rail of the foldable section of the imager based object positioner system.

FIG. 7D is an isometric, top view of a vertical level adjustment mechanism 48 of the vertical offset system shown attached to a rail 12 of the foldable section 14 of the imager based object positioner system 10. The adjustment mechanism 48 can be coupled to a gear 49. The gear 49 can be engaged to the vertical arm 42 via the track 41.

Figure 8A:
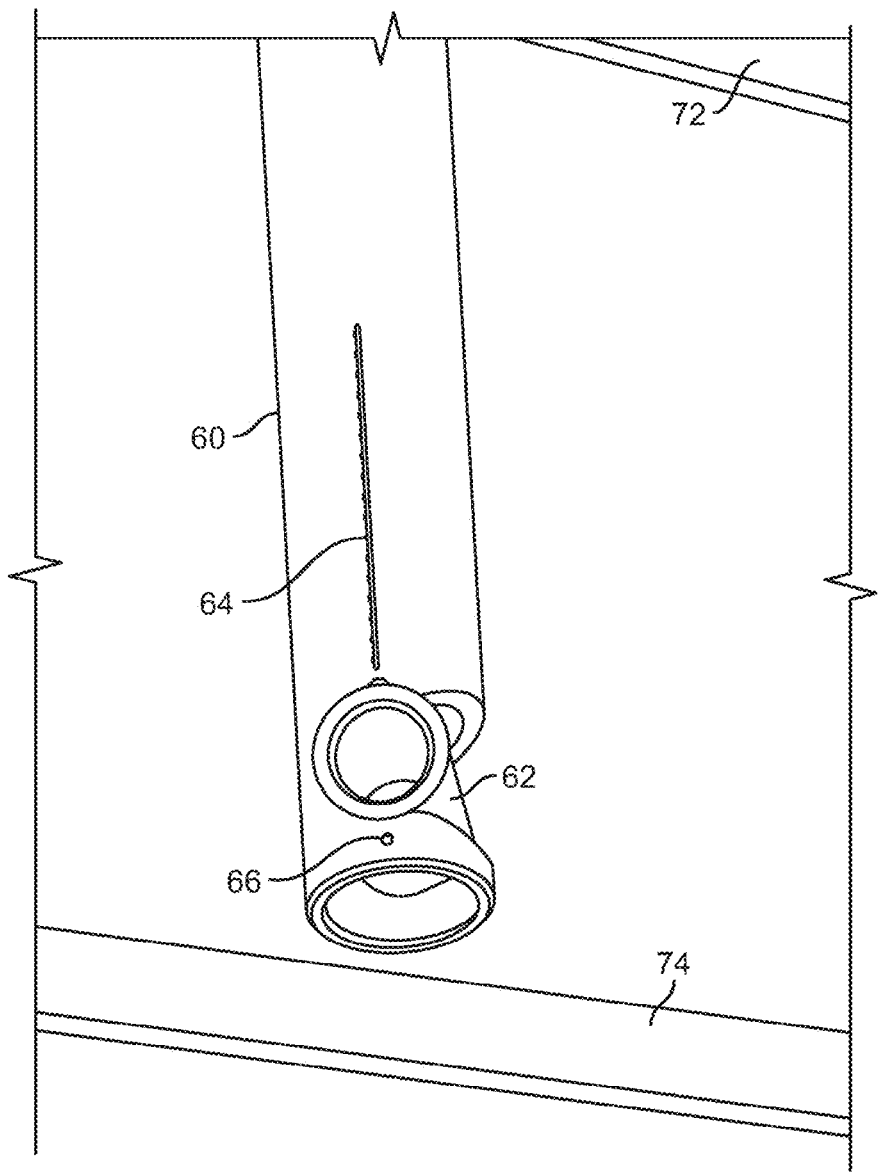
FIG. 8A is a top view of a guide boom of the vertical offset system of the imager based object positioner system shown in FIG. 5A.

FIG. 8A is a top view of a guide boom 60 of the vertical offset system 40 of the imager based object positioner system 10 shown in FIG. 5A. In an implementation, the boom can be translucent to the energy generated by the imager to which the system 10 can be attached. In an implementation the boom can include one or more markers 66, 64 that can be opaque to the energy generated by the imager to which the system 10 can be attached. The boom 60 also can include an object coupling bushing 62. In an implementation bushing 62 can also be opaque to the energy generated by the imager to which the system 10 can be attached.

Figure 8B:
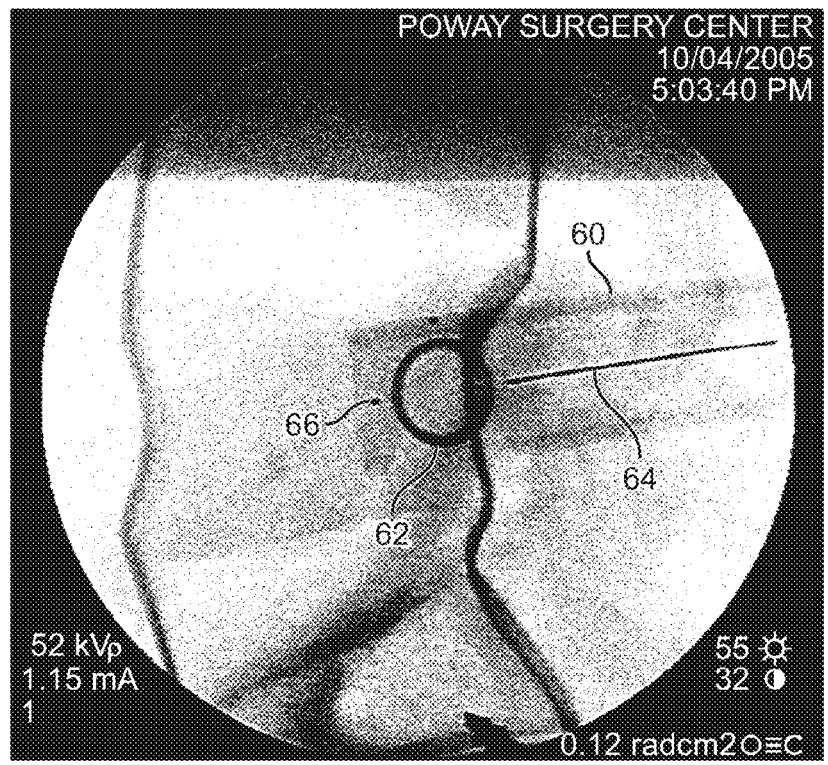
FIG. 8B is a picture of an image generated by an imager of the boom shown in FIG. 8A adjacent to bony anatomy.
Figure 8C:
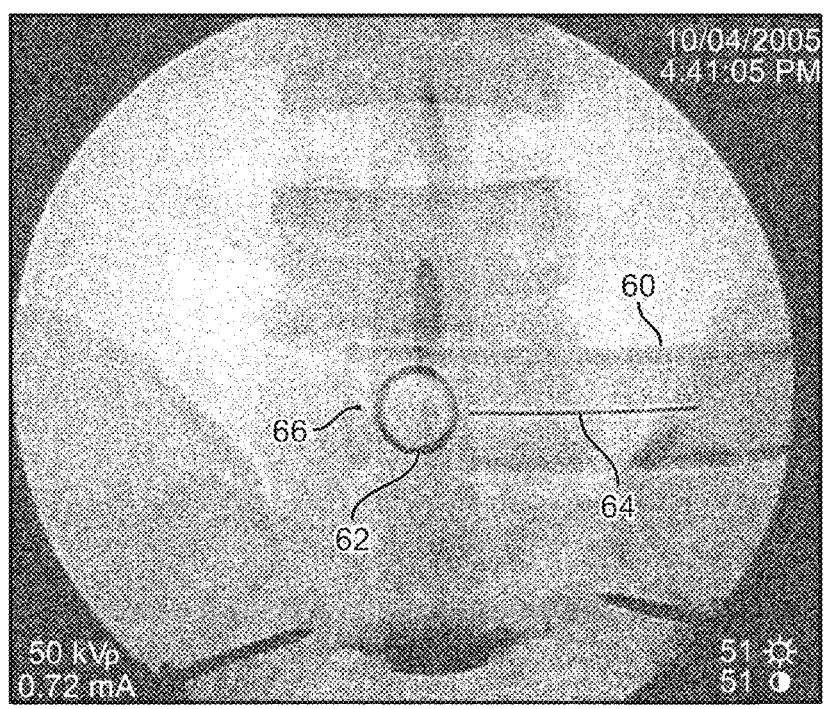
FIG. 8C is a picture of another image generated by an imager of the boom shown in FIG. 8A adjacent to bony anatomy.

FIGS. 8B and 8C are pictures of images generated by an imager including the boom shown in FIG. 8A adjacent to bony anatomy. As shown in these figures, the marks 64, 66 and bushing 62 can absorb energy generated by an imager enabling their identification in images generated by the imager. The markers 62, 64, 66 can be used to align the bushing with a desired line or plane of approach to desired target. An object can be coupled to the bushing 62 to enable precise placement of the object along the desired line or plane established by the imager while the system 10 remains coupled to the imager.

Figure 9:
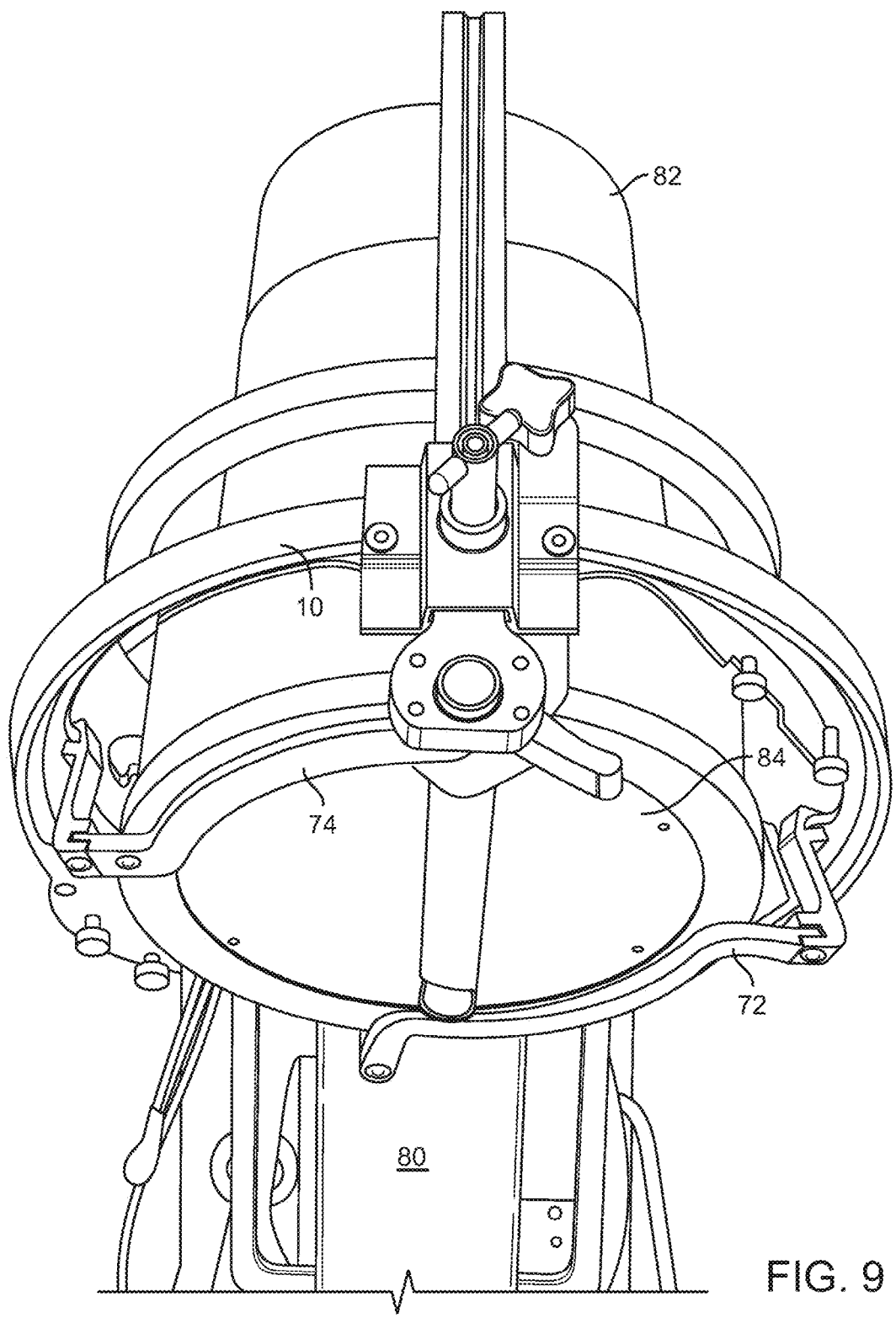
FIG. 9 is an implementation of an imager based object positioner system shown in FIG. 5A mounted on an imager.

FIG. 9 is a picture of an imager based object positioner system 10 shown in FIG. 5A mounted on an imager 80. The imager 80 can include a transmitter 82 with distal end 84, wherein the transmitter 82 can be supported by a mechanical linkage such as a "C-Arm". In this example, the imager 80 can be a mobile digital fluoroscope. In this implementation, the positioner system 10 can be coupled to the transmitter's 82 distal end 84. As also shown in FIG. 9 the placement bar/stabilizer bars 72, 74 engage the imager 80 transmitter's 82 distal end while not blocking energy transmission. In this implementation, the system 10 can include three clamps 32, 34, 36 that, in combination with the stabilization bars 72, 74 securely holds the positioner system 10 to the imager 80 transmitter 82. As shown in FIGS. 8B and 8C and can be seen in FIG. 9, in an implementation only the boom 60 can be positioned in imager's energy field preventing distortion or artifacts in the image generated by an imager coupled to the system 10.

FIGS. 10A-10F illustrate an interrelated implementation of an imager based object positioner system 10. The imager based object positioner system 10 can include a circular upper rail 12, a circular lower rail 13 coupled to the upper rail 12, and a vertical offset mechanism 40. The lower rail 13 can be coupled to the upper rail 12 by a plurality of connectors 17. Each of the upper and lower rails 12, 13 can be sized to receive a transmitter 82 of an imager 80 such that they encircle the transmitter 82. The upper rail 12 can include a clamp 32 configured to be moved radially inward towards the transmitter 82 and radially outward away from the transmitter 82 such that the clamp 32 can be reversibly pressed against the transmitter 82. The upper rail 12 can also include clamps 34, 36 that are positioned at locations away from the clamp 32 around the circumference of the upper rail 12. The three clamps 32, 34, 36 can be used in conjunction to engage the transmitter 82 of an imager 80. The system 10 can be placed over an imager transmitter 82. The handle 30 can be engaged to cause the clamp 32 to apply force in conjunction with clamps 34, 36 against the imager transmitter 82 to releasably hold the positioner system 10 to the imager transmitter 80 or receiver. When clamp 32 is moved radially inward against the transmitter 82, clamps 34, 36 act as bearing surfaces such that the imager based object positioner system 10 can be placed into clamped engagement with the transmitter 82. The clamps 32, 34, 36 can be about 120 degrees apart around the circumference of the upper rail 12.

Clamps 34, 36 can be adjustable to change the relative position of the imager based object positioner system 10 even after clamping by clamp 32. Clamps 34, 36 can each include an adjuster knob 18 in threaded engagement with the clamps 34, 36 via a threaded pin 19. The threaded pin 19 extends through a first bore 23 in the upper rail 12 and into a second bore 25 in the corresponding clamp 34, 36 (see FIG. 10D). The first and second bores 23, 25 can be threaded to adjustably engage with their respective threaded pin 19. As the knob(s) 18 on the pins 19 are rotated, the threaded pin 19 can advance (or withdraw from depending on direction of rotation) into bores 23, 25 bringing the upper rail 12 into tighter (or looser) engagement with the respective clamps 34, 36 thereby changing the plane of the upper rail 12. A user can thereby adjust the plane of the rail 12 relative to the plane of the image intensifier 80. An image intensifier 80 can have a central axis between the transmitter 82 and receiver. The plane of the rail 12 can be substantially coaxially aligned with the plane of the transmitter 82 by making fine adjustments using the knobs 18. The system can thereby allow a user to calibrate the guidance provided by the imager based object positioner system 10 to the central axis of the image intensifier 80.

Again with respect to FIGS. 10A-10F, the vertical offset mechanism 40 can include a releasable car 44, vertically translatable arm 42, car release assembly 50, and guide boom 60. The car 44 can be release-ably engage the upper rail 12. The car 44 can move along the rail 12 when the car release assembly 50 is disengaged. The car system 44 can include an upper engagement lip 45, a lower engagement lip 54, car release assembly 50, and release assembly lever 52. The lever 52 can be used to release-ably engage a lower surface of the upper rail 12 via the engagement lip 54 and the upper surface of the rail 12 via the engagement lip 45.

Figure 10A:
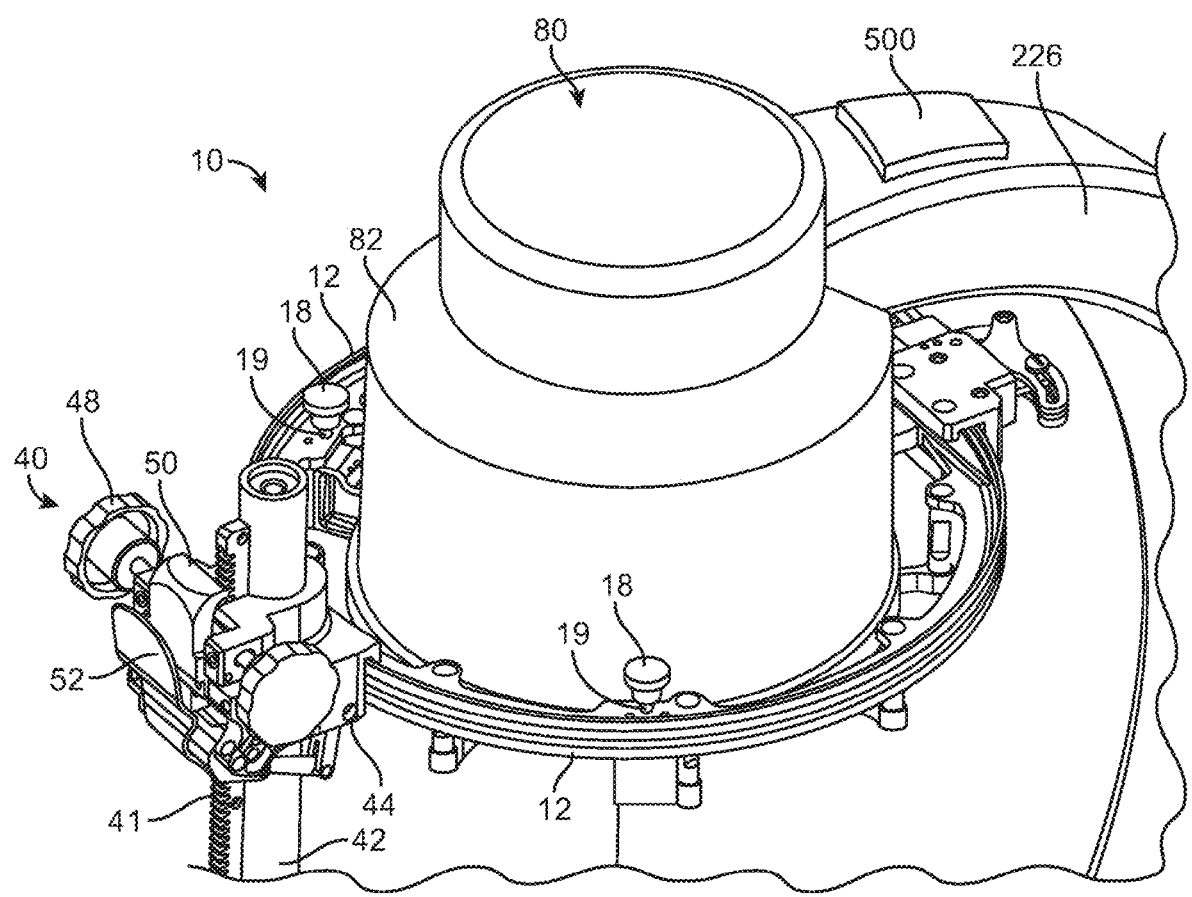
FIG. 10A is another implementation of an imager based object positioner system shown in FIG. 1D.
Figure 10B:
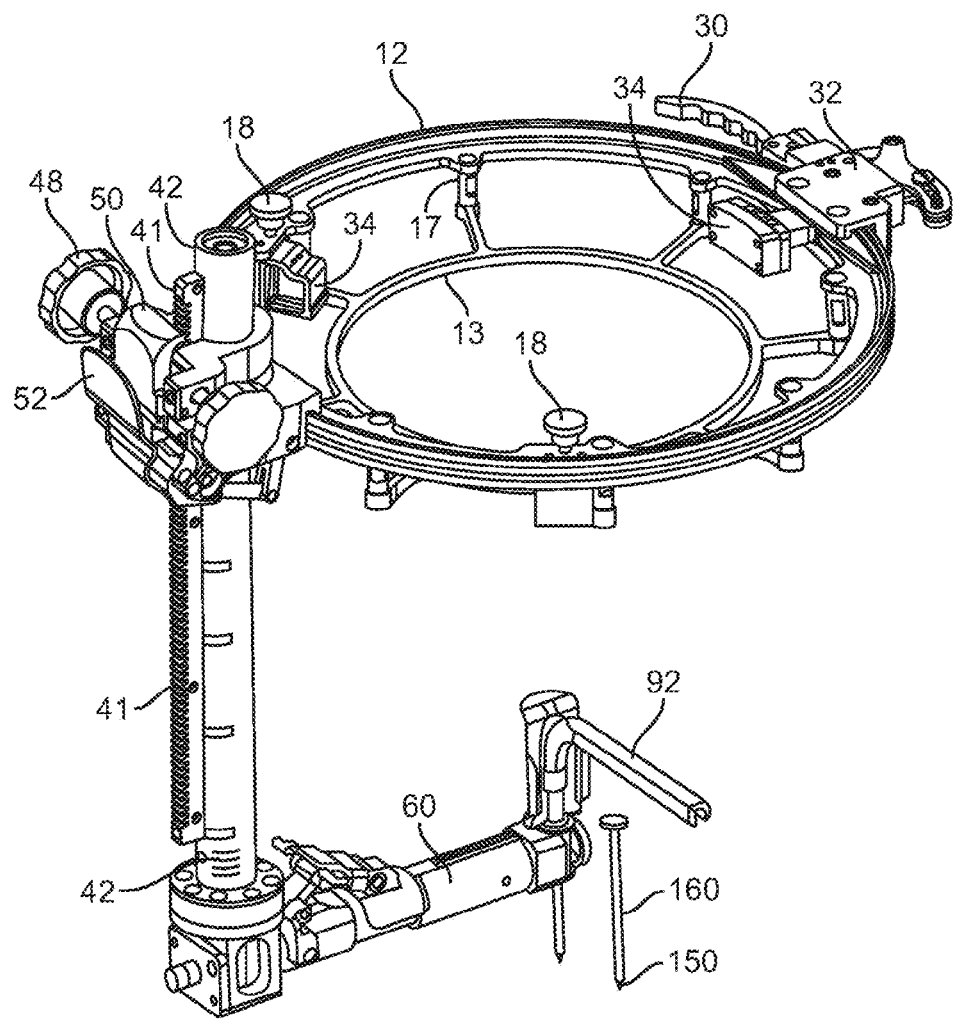
FIG. 10B is a view of the imager based object positioner of FIG. 10A.
Figure 10C:
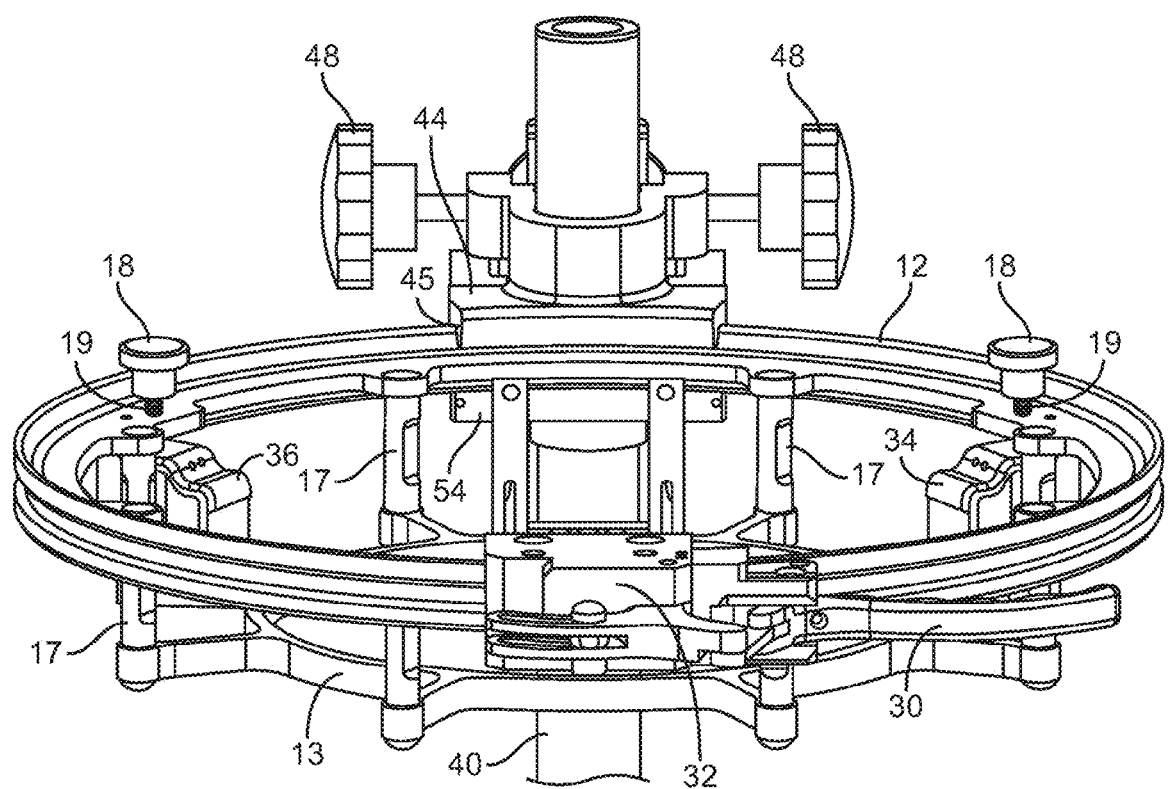
FIGS. 10C-10F are detail views of the imager based object positioner of FIG. 10B.
Figure 10D:
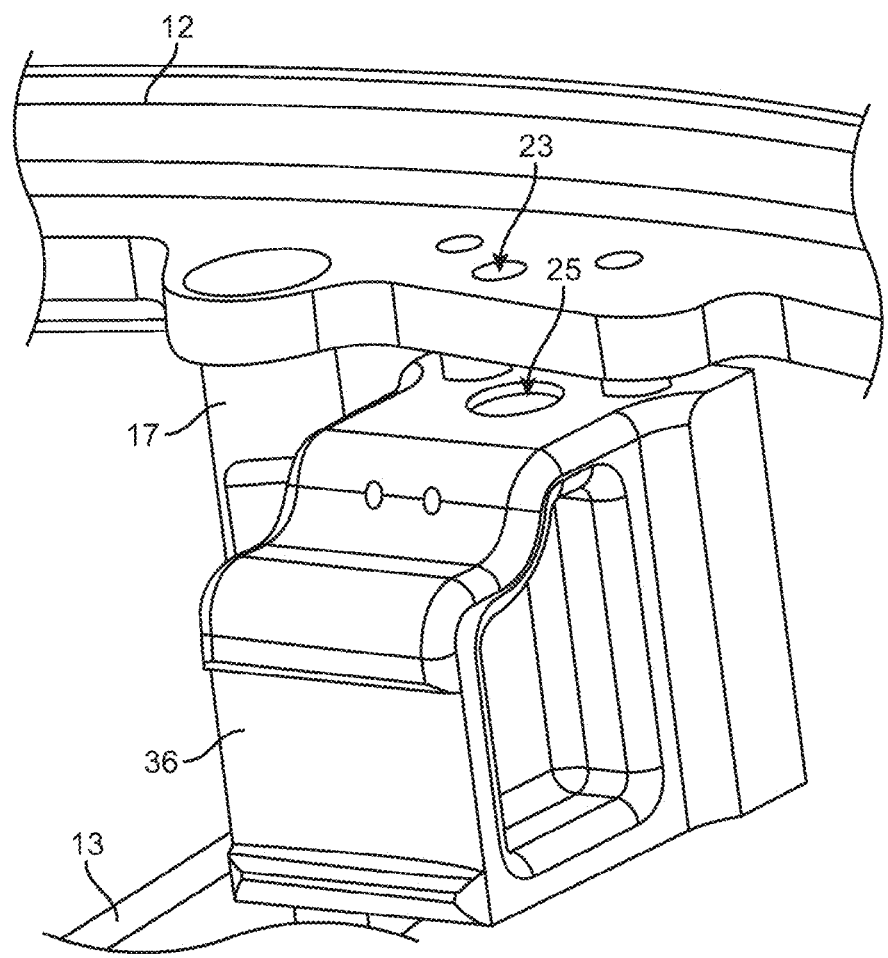
Figure 10E:
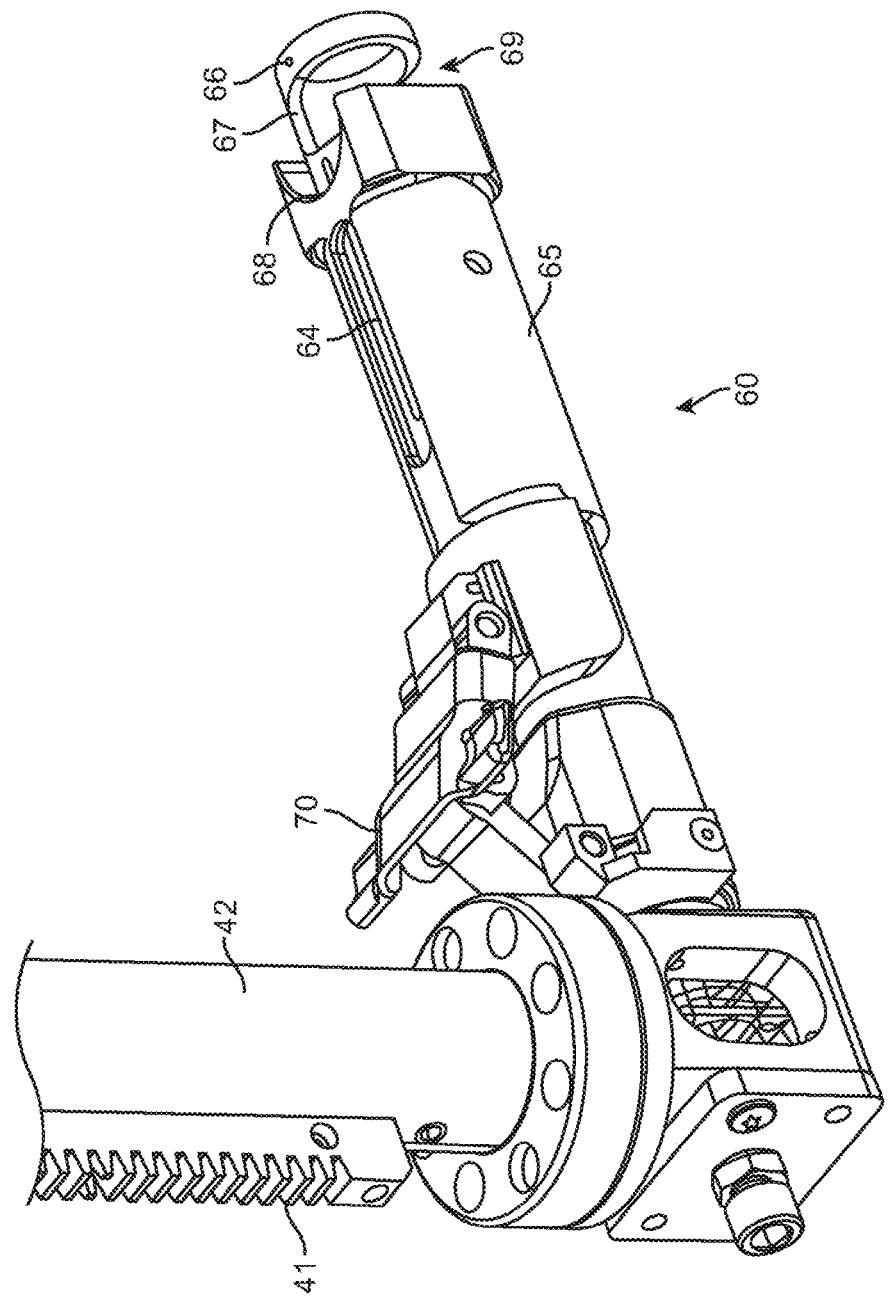
Figure 10F:
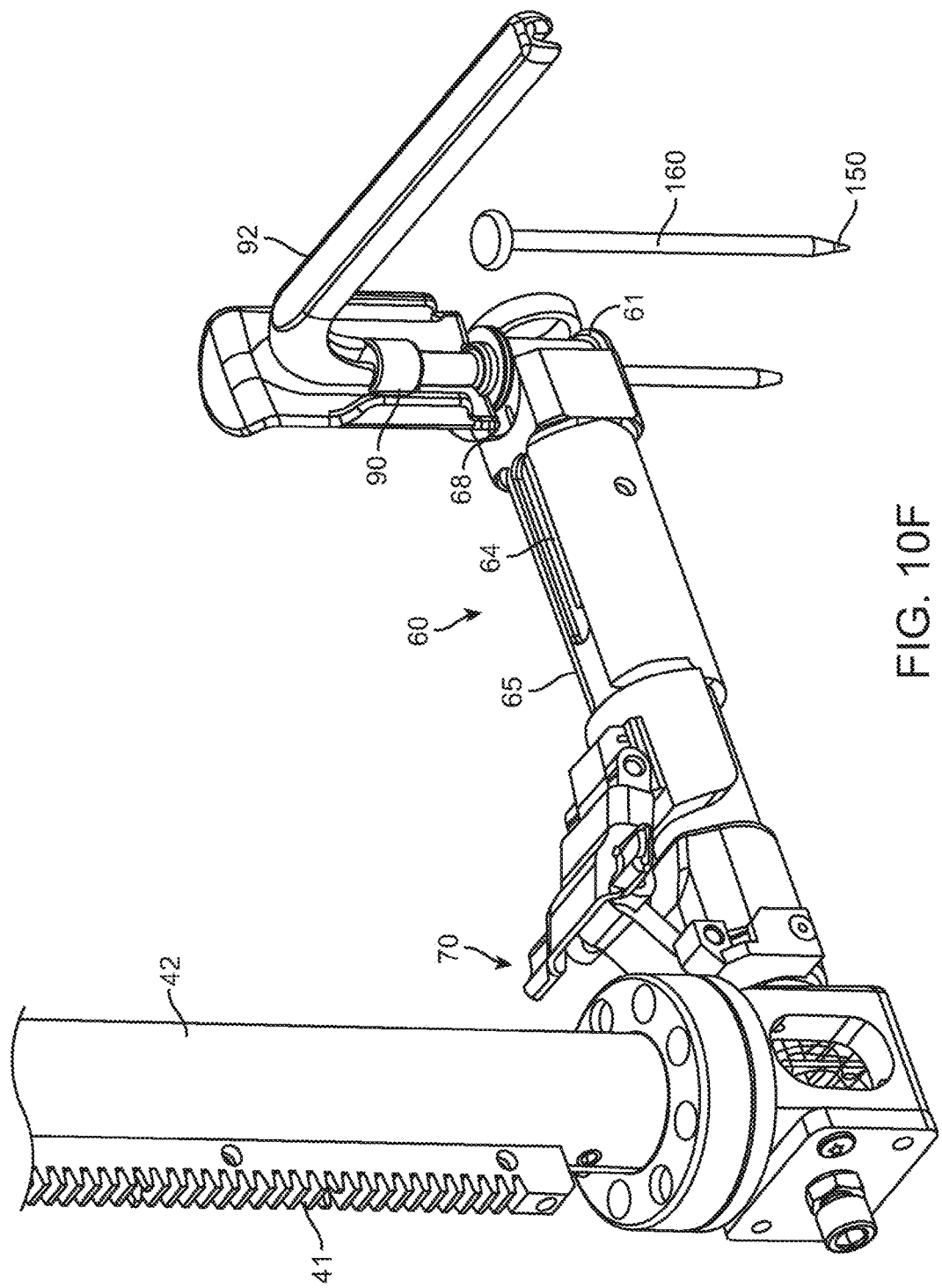

As best shown in FIG. 10E, a guide boom 60 can be coupled to a distal end of the arm 42 of the vertical offset system 50. The boom 60 can be translucent to the energy generated by the imager to which the system 10 can be attached. The boom 60 can include one or more radiopaque markers 64, 66. A distal end region of the boom 60 can include an object coupling bushing 62. The bushing 62 can be cylindrical and may also be radiopaque. The markers 64, 66 in combination with the bushing 62 can be used to align the bushing 62 with a desired line or plane of approach to the desired target. An object may be coupled to the bushing 62 to allow precise placement of the object along the desired line or plane established by the imager while the system 10 is coupled to the imager.

The bushing 62 can be in a fixed arrangement near an end of the boom 60 as shown in FIG. 8A. Alternatively, the system 10 can include a bushing 62 formed by a removable support sleeve 61 configured to be placed in reversibly clamped arrangement with a distal end region 63 of the boom 60. As best shown in in FIG. 10E and also FIG. 10F, the boom 60 can include an outer member 65 movable relative to an inner member 67. The outer member 65 can be bi-directionally movable such that it can be advanced distally and withdrawn proximally relative to the inner member 67. The inner member 67 can have a slot 69 near its distal end that can receive the removable support sleeve 61 therethrough. The support sleeve 61 can be engaged within the slot 69 by advancing distally the outer member 65 using a clamping element 70. For example, the clamping element 70 can be urged in a downward direction, which thereby moves the outer member 65 distally causing a clamping surface 68 at a distal end of the outer member 65 to capture the support sleeve 61 within the slot 69.

Figure 11A:
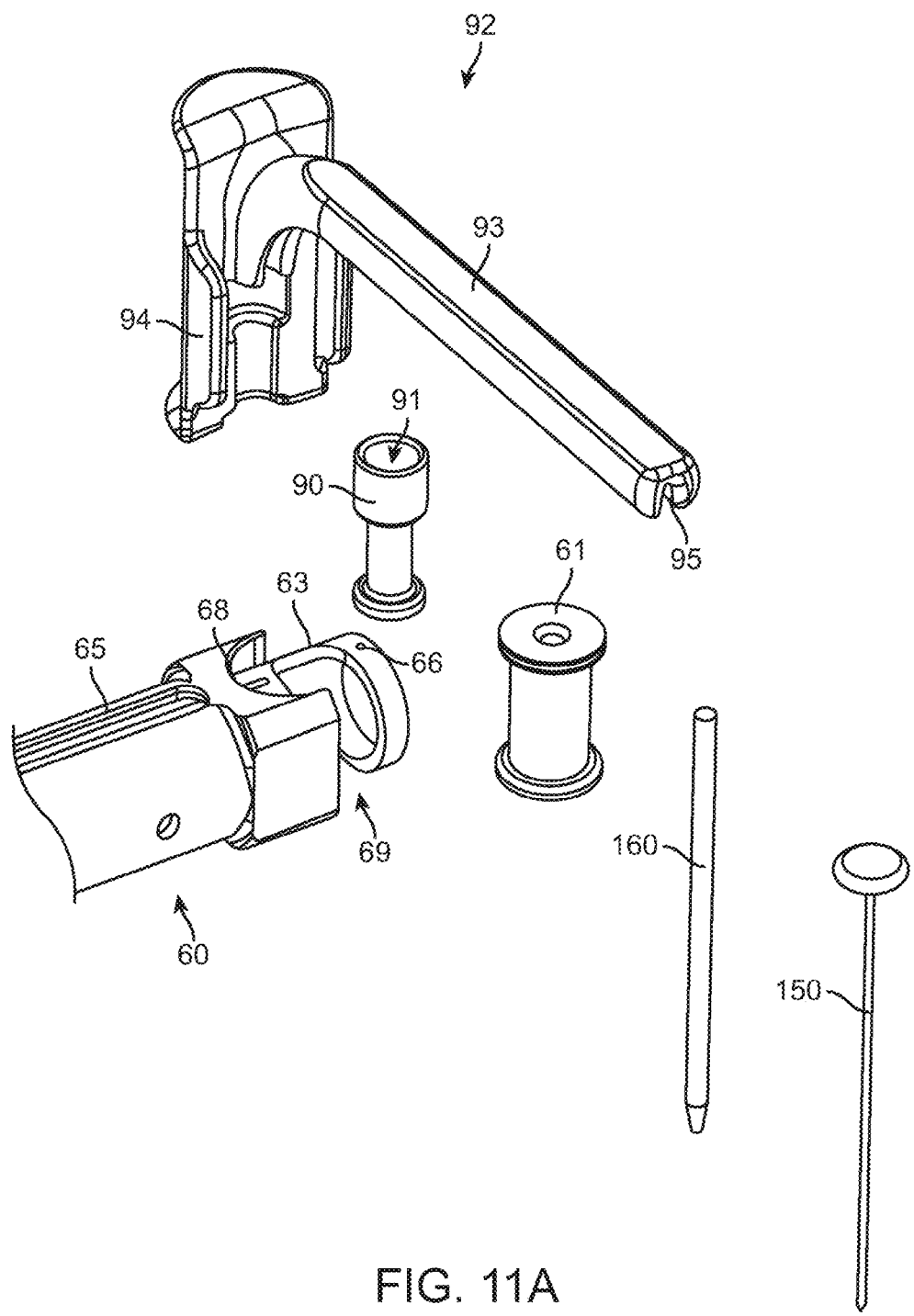
FIG. 11A is an exploded view of a redirection support and removable guide element for coupling with a boom of the imager based object positioner of FIG. 10A.
Figure 11C:
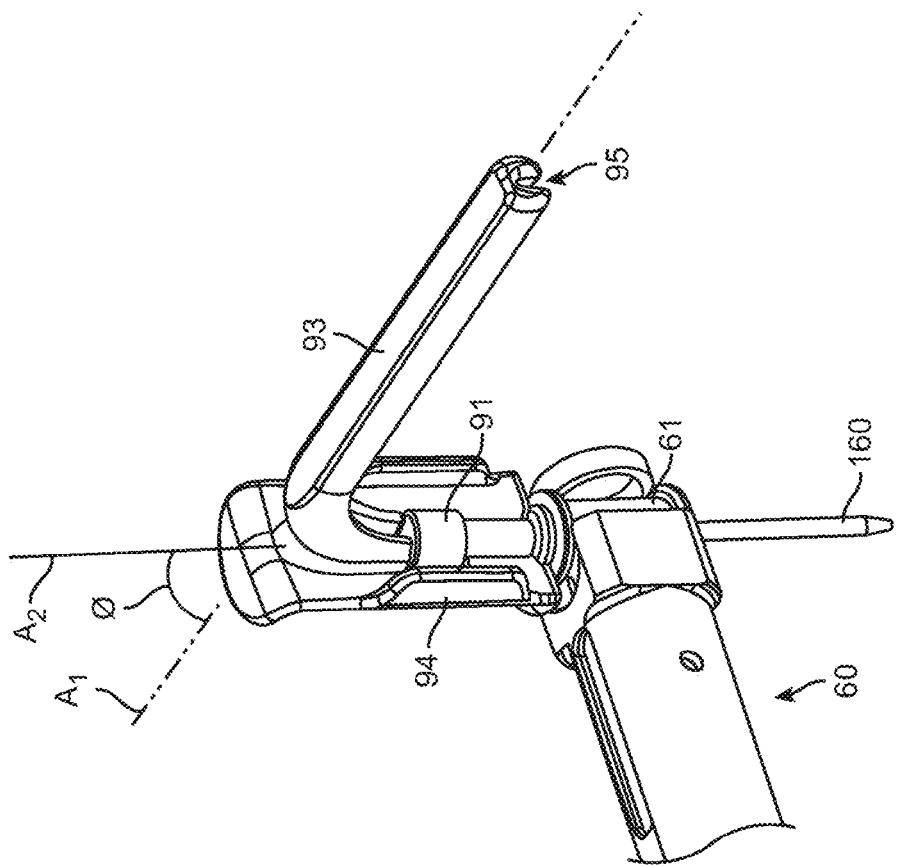
FIG. 11C is an assembled view of the removable guide element and redirection support positioned with a boom of the imager based object positioner of FIG. 10A.
Figure 11B:
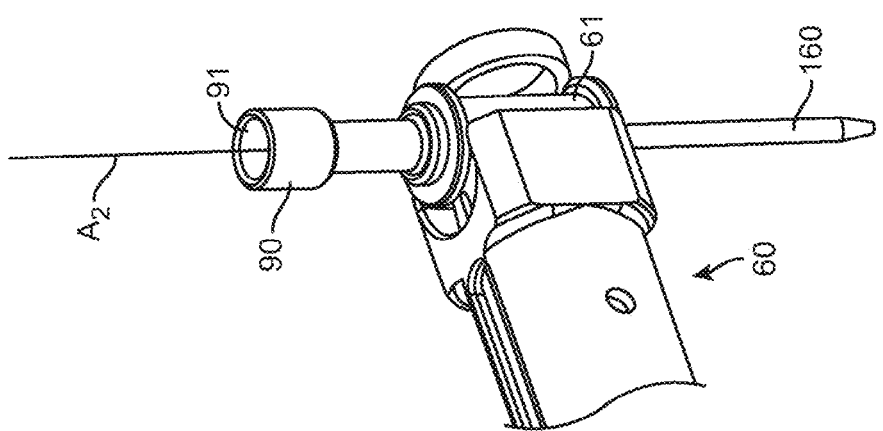
FIG. 11B is a partially assembled view of the removable guide element coupled with a boom of the imager based object positioner of FIG. 10A.

As shown in FIGS. 11A-11C, the system 10 can be used with a removable guide element 90 and a redirection support 92. The removable guide element 90 can couple to an upper end of the support sleeve 61 clamped within slot 69 of the boom 60. The guide element 90 can have a bore extending from an upper end 91 to a lower end such that upon coupling the guide element 90 to the support sleeve 61, the bore of the guide element 90 can be aligned coaxially with the bore of the support sleeve 61. The upper end 91 of the guide element 90 can have a funnel shape such that it can be used to direct objects towards into bore, for example, if the object is advanced along a nonlinear path at an angle to a longitudinal axis of the guide element 90. The redirection support 92 can be a removable element configured to mate with a region of the guide element 90 during or prior to advancement into an object through the guide element. The redirection support 92 can include an upper arm 93 and a lower arm 94. The lower arm 94 of the redirection support 92 can include a region shaped to mate with an upper end 91 of the removable guide element 90 (FIG. 11A). The redirection support 92 can mate such that it is mechanically coupled to the upper end 91 or the redirection support 92 can be held in place by a user as the object is advanced. The upper arm 93 can include a u-shaped channel forming a receiver surface 95 in its lower surface. The upper arm 93 can bend or curve at an angle into the lower arm 94 such that the receiver surface 95 formed on the lower surface of the upper arm 93 can be continuous with the receiver surface 95 of the lower arm 94. The redirection support 92 can direct the object into the funnel shaped surface of the upper end 91 of the guide element 90 towards the bore extending through the guide element 90 and the support sleeve 61. Thus, the redirection support 92 can have a curvilinear shape such that it helps to redirect the object along an arcuate path towards the bore. The receiver surface 95 of the upper arm 93 can be sized and shaped to receive an object advanced along a first axis $A_1$ or orientation to a second axis $A_2$ or orientation. FIG. 11C illustrates the axes $A_1$ and $A_2$ as orthogonal to one another but it should be appreciated that other angles are considered herein. An angle $\theta$ between the two axes $A_1$ and $A_2$ of orientation can be greater than 45 degrees and less than 120 degrees. In some implementations, the support 92 can redirect an object an angle $\theta$ of about 90 degrees such that the upper and lower arms 93, 94 and their respective receiver surfaces 95 are arranged substantially 90 degrees to one another. In some implementations, the object advanced into the bore can be a flexible drill/guide pin 150. The redirection support 92 avoids the need for complicated and specialized right angle pin drivers and allows standard pin drivers to be used to advance the flexible guide pin 150. Generally, the redirection support 92 can redirect the flexible drill/pin and subsequently a blunt guide pin, from an axis that is orthogonal or nearly orthogonal to the axis that the pin ultimately assumes within the pin support sleeve and the patient. The angle can be orthogonal to (i.e. 90 degrees to) or another angle that can be between 45 and 120 degrees. The pin 150 can be a flexible nitinol material or other material commonly known to those of ordinary skill in the art.

Figure 12:
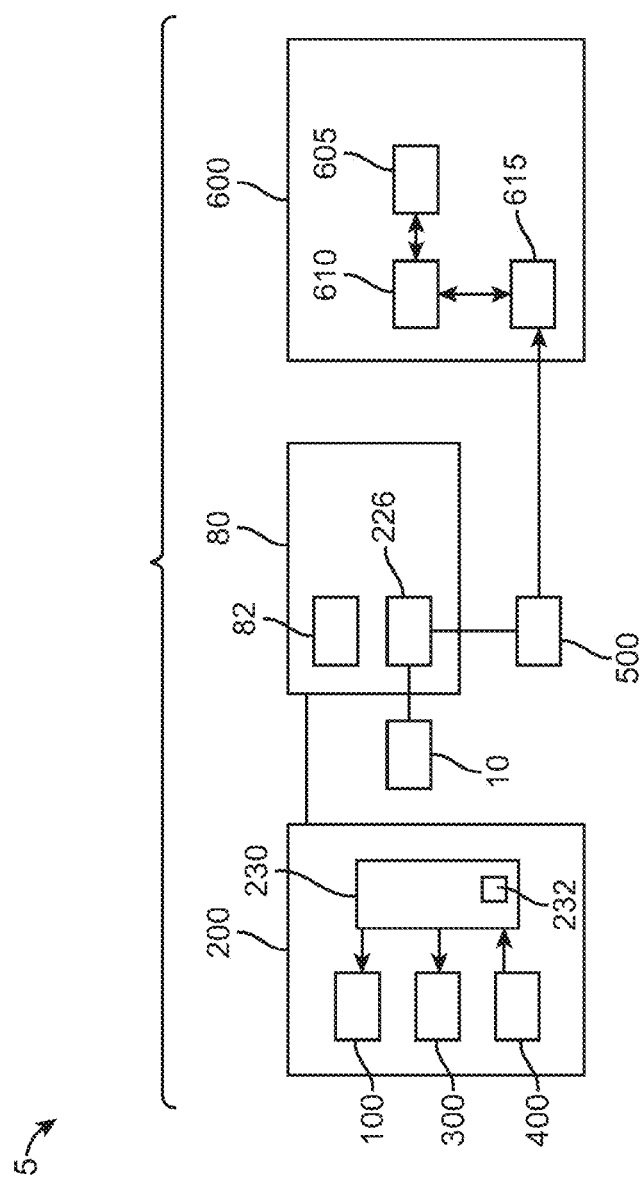
FIG. 12 is a block diagram of an implementation of a system as described herein.

FIG. 12 is a block diagram showing an implementation of the system 5 including a guidance system 200 having one or more electronic positioning devices 100, 300 which can be configured to move an imager 80 having an imager based object positioner system 10 attached thereto. As mentioned above, the system 5 can include one or more sensors 500 configured to provide information regarding orientation of one or more of the components. The sensors 500 can measure angles of slope or tilt of one or more of the components of the image based guidance system 200. In an implementation, the one or more sensors 500 can include an inclinometer, such as a dual axis MEMS inclinometer configured to provide orientation data in at least one and preferably at least two planes. The sensor 500 can be attached to the portable image intensifier such as on the C-Arm 226 so as to measure angles of tilt of the C-Arm 226 with respect to gravity. The sensor 500 can provide real-time inclination angle values along at least one orientation of the central axis of the image intensifier relative to the gravity line, the central axis can be defined by a line connecting the x-ray emitter and the receiver element. The real-time inclination angle values relative to a gravity line can be in two orthogonal planes. For example, the real-time inclination angle values can provide information regarding the lateral tilt and the lordotic tilt of the C-Arm 226 during a procedure.

Still with respect to FIG. 12, the information collected in real-time by the one or more sensors 500 can be communicated to an external computing device 600 having a communication module 615. The communication module 615 of the external computing device 600 can include a wired communication port such as a RS22 connection, a USB connection, a FireWire connection (or similar version of a standard IEEE 1394 high performance serial bus), proprietary connections, or any other suitable type of hard-wired connection configured to receive and/or send information to the external computing device 600. The communication module 615 of the external computing device 600 can alternatively or additionally include a wireless communication port such that information can be fed between the one or more sensors 500 and the external computing device 600 via a wireless link, for example to display information in real-time on the external computing device 600. The wireless connection can use any suitable wireless system, such as Bluetooth®, Wi-Fi, radio frequency, Zigbee (or other IEEE 802.15.4-based specification or communication protocols), infrared or cellular phone systems, and can also employ coding or authentication to verify the origin of the information received. The wireless connection can also be any of a variety of proprietary wireless connection protocols. The external computing device 600 can also control one or more components of the system 5 such that the communication between the system 5 and the external computing device 600 can be an authentic two-way communication.

Figure 13:
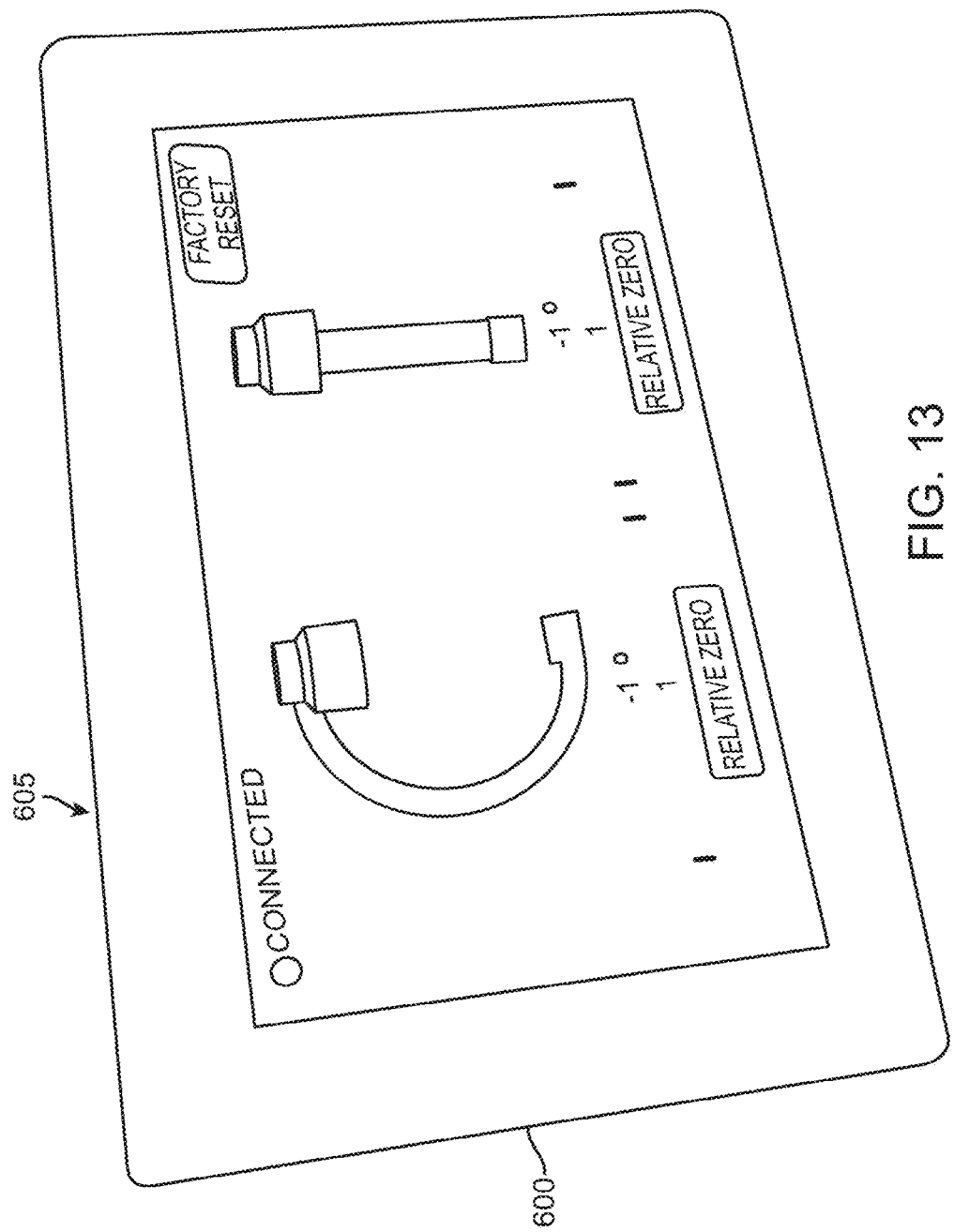
FIG. 13 is a screen shot of a user interface displaying angles of an image intensifier according to an implementation.

The external computing device 600 with which the one or more sensors 500 communicates can vary including, but not limited to, a desktop computer, laptop computer, tablet computer, smartphone or other device capable of displaying information and receiving user input. The user interface 605 of the external computing device 600 can display information regarding the use of the system 5, particularly the one or more sensors 500, relayed in real-time and provided to a user instantaneously during use of the system 5. The user interface 605 of the external computing device 600 can also include one or more inputs such as a touchscreen or other inputs including buttons, keys, touchpads, or the like such that a user can interact with the processor to perform certain actions related to the programming of the instrument 10. The user interface 605 can receive manual input from a user and may include at least one actuator, trigger, pushbutton, keypad, touchscreen, or other input. The user interface 605 may include at least one light, screen, display or other visual indicator to provide instructions and/or information to the user, such as the angle of the C-Arm 226 in at least one plane. FIG. 13 illustrates a screen shot of a user interface 605 displaying angles of the C-Arm 226 in a first plane showing lateral angle and in a second plane shoring lordotic angle. The data can be displayed graphically such as an image of the C-Arm 226 itself showing rotation around the axis. The data can additionally or alternatively be displayed as a number relative to the axis. It should be appreciated that angle of the C-Arm 226 can be adjusted remotely using the user interface 605 of the external computing device 600 or the user interface 605 of the external computing device 600 display the data and adjustments made on another controller such as controller 230 as described elsewhere herein.

The controller 610 of the external computing device 600 can include at least one processor and a memory device. The external computing device 600 can include at least one processor and a memory device. The memory may be configured for receiving and storing user input data as well as data acquired during use of the system 5 such as from the one or more sensors 500. The memory can be any type of memory capable of storing data and communicating that data to one or more other components of the device, such as the processor. The memory can be one or more of a Flash memory, SRAM, ROM, DRAM, RAM, EPROM, dynamic storage, and the like. The memory can be configured to store one or more user-defined profiles relating to the intended use of the system 5. The memory can be configured to store user information, history of use, measurements made, and the like.

Methods of Use

Described herein is a method of using the system 5 to implant a guide pin 150 into first and second pedicle P through a thin walled cannula or trocar 160. The method described below is just one of many ways in which the system 5 can be used and should not be limiting. The system 5 described herein can be used for many surgical techniques where less invasive, percutaneous, or minimally invasive access is desired. As a first step, the one or more inclinometers 500 can be coupled to the C-Arm 226 to transmit data to the computing device 600. The computing device 600 displays the lateral and lordotic angles of the C-Arm 226 are both at 0 such that the transmitter 82 can be positioned directly over the pedicles from a posterior position. Images can be obtained by the image intensifier 80 to visualize the pedicles to assess whether the pedicles are level and equidistant. The operating table or the C-Arm 226 can be rotated until the pedicles appear level and equidistant. Once the alignment of the pedicles is confirmed, the C-Arm 226 can be rotated by the electronic positioning device 100 to achieve a true lateral position. The C-Arm 226 can be rotated using the controller 230 until data provided by the sensors 500 on the user interface 605 of the external computer device 600 show a lateral tilt angle of at least about 88 degrees relative to line of gravity. Another image can be taken by the image intensifier 80 to assess whether the marker 64 on the boom 60 is substantially parallel to the pedicle axis or the axis of the endplate. The lordotic angle can be checked and can be adjusted using the controller 230 until confirmed to be parallel. The C-Arm 226 can be rotated on the convergence angle until the lateral tilt angle sensed can be approximately 25 degrees. The line of the radiopaque marker 64 should intersect the line of the radiopaque marker 66 on the boom 60. The C-Arm 226 can be moved using the micropositioner 300 caudally and/or laterally until the marker 64 on the boom is aligned just lateral to and just exterior to the superior articular process of the target.

Figure 14:
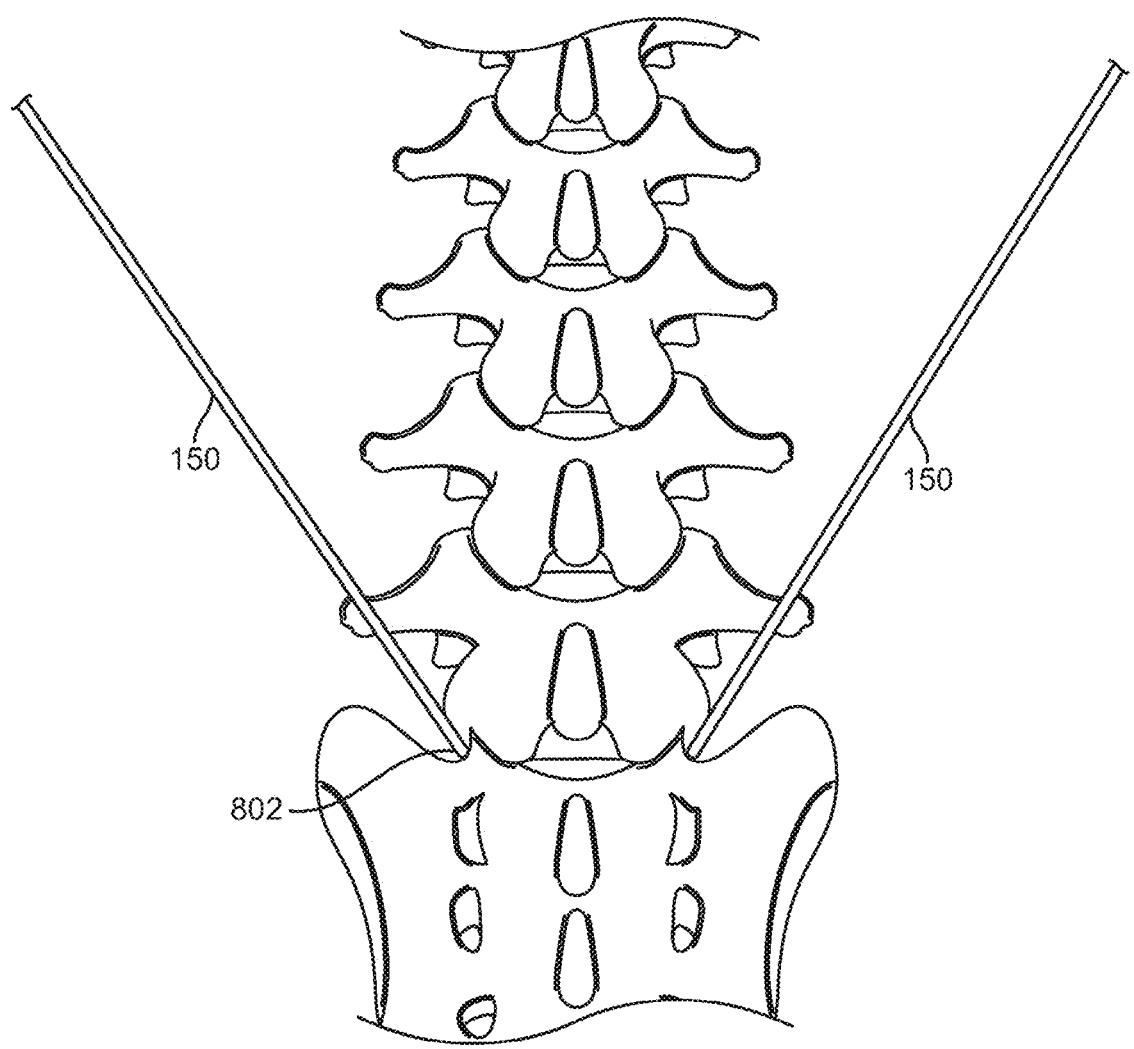
FIG. 14 is an illustration of a pair of guide pins implanted within left and right pedicles from a posterior view.
Figure 15:
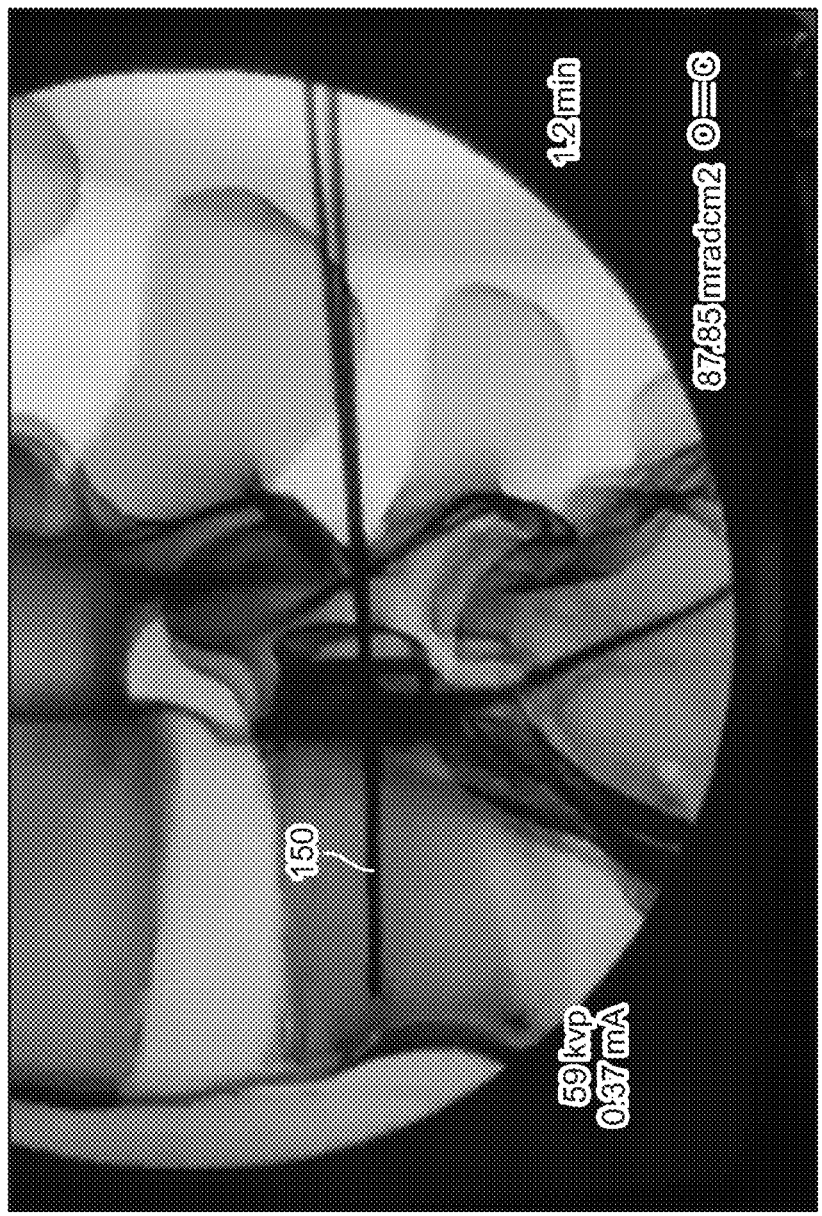
FIG. 15 is an image of a pair of guide pins implanted within left and right pedicles from a lateral view.

A radiopaque support sleeve 61 having a sharp tipped trocar 160 extending through it can be inserted within the slot 69 of the inner member 67 and clamped in place by locking the clamping element 70 thereby urging the clamping surface 68 against the support sleeve 61 capturing it within slot 69. An incision can be made within the soft tissue of the patient. The pin support sleeve 160 having a sharpened trocar tip can be advanced down through the bore of the support sleeve 61 and through the incision until the sharpened tip of the pin support sleeve 160 engages the bone. An image can confirm the position of the support sleeve 61 and the trocar 160 relative to the pedicle wall. The flexible guide pin 150 can be fed down through the shaft of the support sleeve 61 until resistance can be felt. A removable guide element 90 can be coupled to an upper end of the support sleeve 61 to aid in redirecting the flexible guide pin 150 down into the bore of the guide element 90. The redirection support 92 can be used to aid in directing the guide pin 150 into the bore. A standard pin driver can be used to advance the pin 150 a selected distance, such as 25 mm or about 1 inch. The standard pin driver can receive the pin 150 through an opening at a front working end and moved to slide over the pin 150 until the front working end of the standard pin driver is a distance away from the end of the upper arm 93 of the redirection support 92. The standard pin driver can drive the pin 150 this distance until the front working end of the driver abuts the upper arm 93. The standard pin driver can then be activated to remove the pin 150 from the bore. The sharp tip pin 150 can be replaced with a blunt-tipped pin 150 by sliding the blunt-tipped pin 150 into place. The support sleeve 61 and trocar 160 can be removed from the boom 60 by releasing the clamping element 70. Each of the steps described above can be repeated on the opposite side pedicle until both guide pins 150 are in position within the left and right pedicles (see FIGS. 14 and 15). The pair of guide pins 150 are in perfect alignment with each other as well as the plane of the vertebral endplate. Importantly, the guide pins 150 were implanted with high precision in terms of the angle of insertion and within a short period of time with very short exposure time with the image intensifier. In some implementations, both guide pins 150 can be implanted with less than about 20 seconds of imaging, such as up to about 13 seconds of imaging.

Method of Aligning Axes

Figure 16:
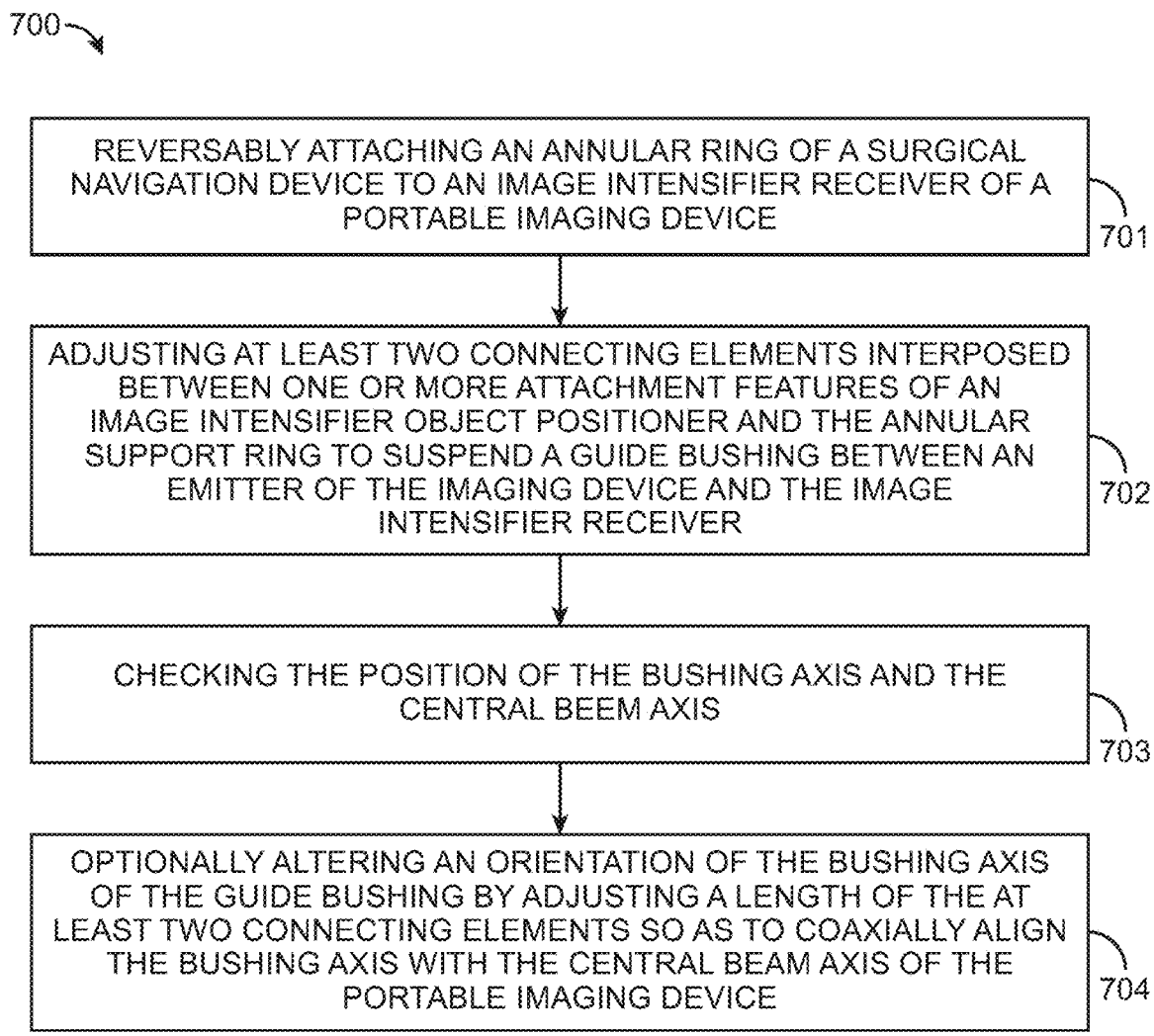
FIG. 16 is a flowchart of a method of coaxially aligning a bushing axis of a surgical navigation device with a central beam axis of a portable imaging device.

Referring to FIG. 16, a method of coaxially aligning a bushing axis of a surgical navigation device with a central beam axis of a portable imaging device 700 is shown. The method includes reversibly attaching an annular ring of the surgical navigation device to an image intensifier receiver of the portable imaging device 701. The annular support ring is attached to an image intensifier object positioner. At least two connecting elements interposed between one or more attachment features of the image intensifier object positioner and the annular support ring are adjusted to suspend a guide bushing between an emitter of the imaging device and the image intensifier receiver 702. The position of the bushing axis and the central beam axis is checked 703. This is done in the unlikely chance that the bushing axis and central axis are already aligned without any additional adjustment to align these axes. An orientation of the bushing axis of the guide bushing is optionally altered by adjusting a length of at least two connecting elements to coaxially align the bushing axis with the central beam axis of the portable imaging device 704.

The portable imaging device illustrated in FIG. 16 can be a radiation-based imaging device including a fluoroscope, X-ray machine, or C-Arm and at least two connecting elements can be threaded elements. Adjusting at least two connecting elements can include a linear translational adjustment. At least a portion of the bushing guide can be radiolucent and/or removable from the surgical navigation device.

Method of Associating Sensor(s) with Imaging Device

Figure 17:
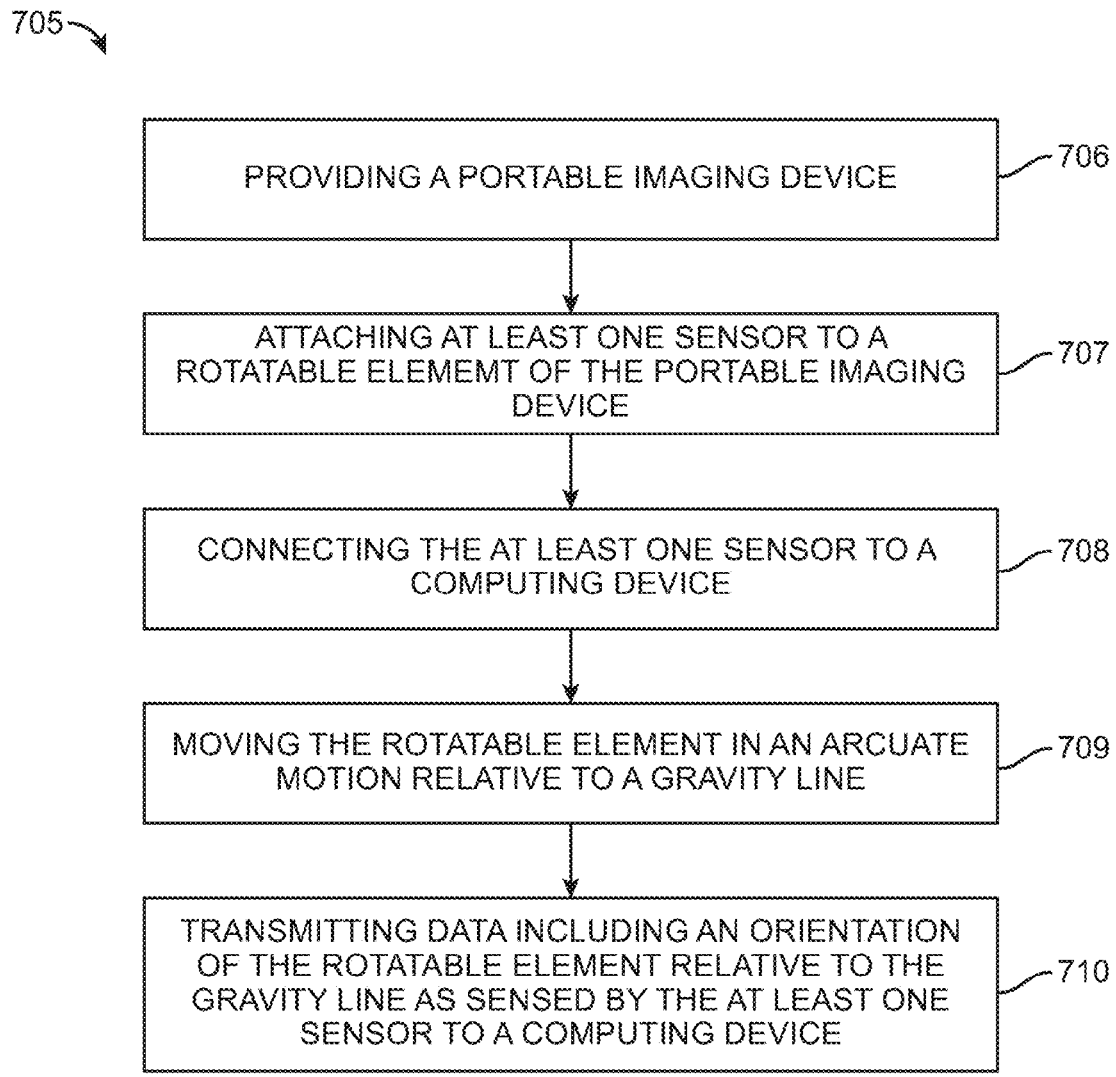
FIG. 17 is a flowchart of a method of associating at least one sensor with a rotatable element of a portable imaging device.

FIG. 17 is a flowchart depicting a method of associating at least one sensor with a rotatable element of a portable imaging device 705. The method includes providing the portable imaging device 706. At least one senor is attached to the rotatable element of the portable imaging device 707. The sensor(s) is/are configured to sense and transmit data. At least one sensor is connected to a computing device 708. The rotatable element is moved in an arcuate motion relative to a gravity line 709. Data, including an orientation of the rotatable element relative to the gravity line, is transmitted (as sensed by at least one sensor) to the computing device 710. The computing device has a viewable display and/or a graphical user interface.

At least one sensor can be an inclinometer and/or a directional accelerometer. The rotating element can be a C-Arm and the portable imaging device is a fluoroscopy machine. The C-Arm can include a portable image intensifier with the at least one sensor attached thereto and configured to measure an angle of tilt of the C-Arm with respect to gravity. The orientation of the rotatable element can include measured angles of slope or tilt from the at least one sensor. The orientation of the rotatable element relative to the gravity line can include a first orthogonal plane and a second orthogonal plane. Each of the first and second orthogonal planes substantially correspond to a sagittal plane and an axial plane of a patient so that when the rotatable element is rotated about the patient, a relative orientation of the central beam axis within the first and second orthogonal planes can be determined relative to the patient. Attaching at least one sensor to the rotatable element of the portable imaging device provides remote reporting of arcuate movements of the rotatable element relative to a gravity line in at least one orthogonal plane. The at least one sensor can include at least one MEMS device and a Bluetooth™ connection to wirelessly connect to the viewable display and/or the graphical user interface of the computing device.

Method of Redirecting an Elongate Member

Figure 18:
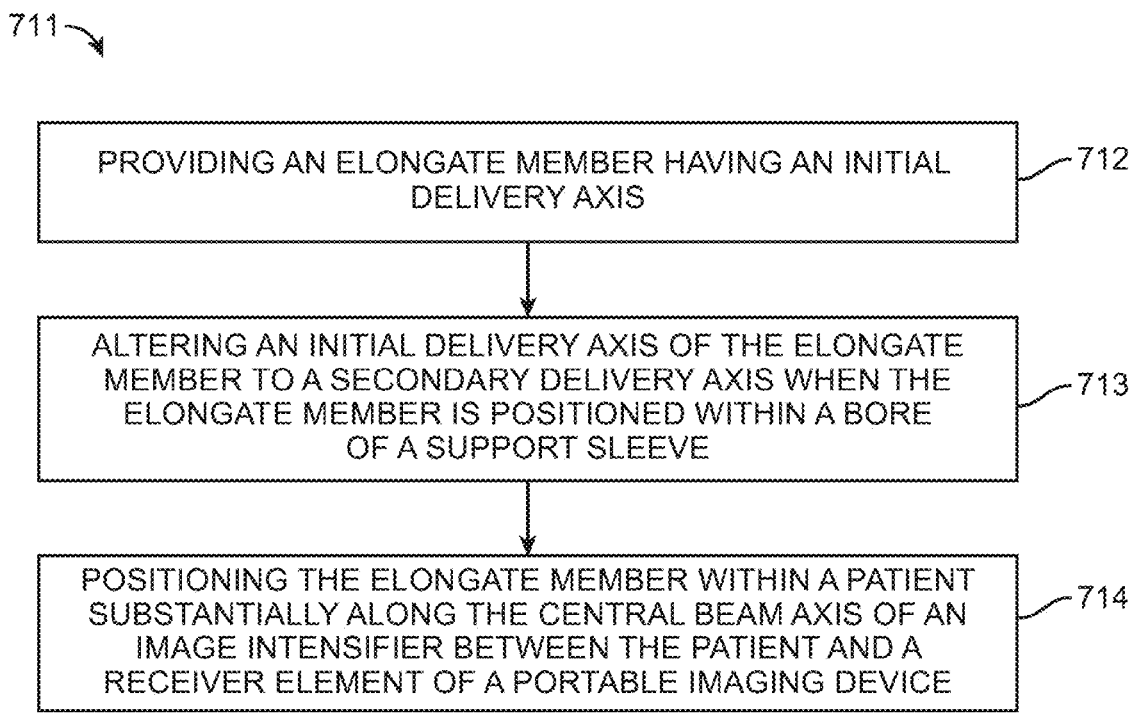
FIG. 18 is a flowchart of a method of redirecting a flexible elongate member along pathways including through a bore of a linear support sleeve configured to be held by a surgical guide bushing positioned coaxially within a central beam axis of a portable imaging device.

FIG. 18 is a flowchart depicting a method of redirecting a flexible elongate member along a non-linear pathway and through a bore of a linear support sleeve 711. The support sleeve is held by a surgical guide bushing positioned coaxially within a central beam axis of a portable imaging device.

The method involves providing the elongate member 712. The elongate member, which can be a guide pin or a needle, for example, has an initial delivery axis 712. Altering the initial delivery axis of the elongate member to a secondary delivery axis occurs when the elongate member is positioned within the bore of the support sleeve 713. The elongate member is positioned within a patient substantially along the central beam axis of an image intensifier between the patient and a receiver element of the portable imaging device 714.

The difference between the initial delivery axis and the secondary delivery axis of the elongate member can be between 45 degrees and 120 degrees. More specifically, the difference can be about 90 degrees. The portable imaging device can be a radiation-based imaging device including a fluoroscope, X-ray machine, or C-Arm. The method can additionally include coupling a guide element to the linear support sleeve. A bore of the guide element can be coaxially aligned with the bore of the linear support sleeve. A removable redirection support can be optionally mated with the guide element. The linear support sleeve can be at least partially radiopaque and the redirection support can be at least partially radiolucent. Furthermore, at least a portion of the non-linear pathway can be a radiolucent ceramic material.

In various implementations, a description is made with reference to the figures. However, certain implementations can be practiced without one or more of these specific details, or in combination with other known methods and configurations. In the description, numerous specific details are set forth, such as specific configurations, dimensions, and processes, in order to provide a thorough understanding of the implementations. In other instances, well-known processes and manufacturing techniques have not been described in particular detain in order to not unnecessarily obscure the description. Reference throughout this specification to "one implementation," "an implementation," or the like, means that a particular feature, structure, configuration, or characteristic described can be included in at least one implementation or implementation. Thus, the appearance of the phrase "one implementation," "an implementation," or the like, in various placed throughout this specification are not necessarily referring to the same implementation or implementations. Furthermore, the particular features, structures, configurations, or characteristics can be combined in any suitable manner in one or more implementations.

The devices and systems described herein can incorporate any of a variety of features. Elements or features of one implementation of a device and system described herein can be incorporated alternatively or in combination with elements or features of another implementation of a device and system described herein as well as the various devices and features described in U.S. Pat. Nos. 7,600,915 and 7,690,844, which are each incorporated by reference herein in their entireties. For the sake of brevity, explicit descriptions of each of those combinations may be omitted although the various combinations are to be considered herein. Provided are some representative descriptions of how the various devices can be used, however, for the sake of brevity explicit descriptions of each method with respect to each type of implant or system being delivered may be omitted.

The use of relative terms throughout the description may denote a relative position or direction or orientation and is not intended to be limiting. For example, "distal" can indicate a first direction away from a reference point. Similarly, "proximal" can indicate a location in a second direction opposite to the first direction. Use of the terms "front," "side," and "back" as well as "anterior," "posterior,"

"caudal," "cephalad", "upward", "downward" and the like or used to establish relative frames of reference, and are not intended to limit the use or orientation of any of the devices described herein in the various implementations.

While this specification contains many specifics, these should not be construed as limitations on the scope of what is claimed or of what may be claimed, but rather as descriptions of features specific to particular implementations. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features can be described above as acting in certain combinations and even initially claimed as such, one or more features from a claimed combination can, in some cases, be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

In the descriptions above and in the claims, phrases such as "at least one of" or "one or more of" may occur followed by a conjunctive list of elements or features. The term "and/or" can also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

What is claimed is:

1. A method of coaxially aligning a bushing axis of a surgical navigation device with a central beam axis of a portable imaging device, the method comprising:

reversibly attaching an annular support ring of the surgical navigation device to an image intensifier receiver of the portable imaging device; wherein the annular support ring is attached to an image intensifier object positioner;

adjusting at least two connecting elements interposed between one or more attachment features of the image intensifier object positioner and the annular support ring to suspend a guide bushing between an emitter of the imaging device and the image intensifier receiver;

checking the position of the bushing axis and the central beam axis; and altering an orientation of the bushing axis of the guide bushing based on the position by adjusting a length of at least one of the at least two connecting elements so as to coaxially align the bushing axis with the central beam axis of the portable imaging device.

2. The method of claim 1, wherein the portable imaging device is a radiation-based imaging device including a fluoroscope, X-ray machine, or C-Arm.

3. The method of claim 1, wherein the at least two connecting elements are threaded elements.

4. The method of claim 1, wherein adjusting the at least two connecting elements includes a linear translational adjustment.

5. The method of claim 1, wherein at least a portion of the bushing guide is radiolucent and/or removable from the surgical navigation device.

6. A device to coaxially align a guide bushing of a detachable surgical navigation device with a central beam axis of a portable imaging device, the device comprises:

an annular support ring of the detachable surgical navigation device configured to be attached to an image intensifier receiver of the portable imaging device, wherein the annular support ring is configured to be attached to an image intensifier object positioner; and at least two connecting elements interposed between one or more attachment features of the image intensifier object positioner and the annular support ring, wherein the at least two connecting elements are configured to suspend a guide bushing between an emitter of the portable imaging device and the image intensifier receiver, wherein an orientation of the bushing axis of the guide bushing is altered by adjusting a length of at least one of the at least two connecting elements to coaxially align the bushing axis with the central beam axis of the portable imaging device.

7. The device of claim 6, wherein the at least two connecting elements are threaded connecting elements configured for linear translational adjustment.

* * * * *